United States Patent
Lu et al.

(10) Patent No.: US 8,785,477 B2
(45) Date of Patent: Jul. 22, 2014

(54) HEXAHYDROPYRROLO[3,4-B]PYRROLE DERIVATIVES, PREPARATION METHODS AND PHARMACEUTICAL USES THEREOF

(71) Applicants: Peng Lu, Pudong Shanghai (CN); Rui Zhang, Pudong Shanghai (CN); Wansong Yu, Pudong Shanghai (CN); Mingjie Zhu, Pudong Shanghai (CN); Yilang Chen, Pudong Shanghai (CN)

(72) Inventors: Peng Lu, Pudong Shanghai (CN); Rui Zhang, Pudong Shanghai (CN); Wansong Yu, Pudong Shanghai (CN); Mingjie Zhu, Pudong Shanghai (CN); Yilang Chen, Pudong Shanghai (CN)

(73) Assignee: Shanghai Sun-Sail Pharmaceutical Science & Technology Co., Ltd. (CN)

( * ) Notice: Subject to any disclaimer, the term of this patent is extended or adjusted under 35 U.S.C. 154(b) by 0 days.

(21) Appl. No.: 13/685,454

(22) Filed: Nov. 26, 2012

(65) Prior Publication Data
US 2013/0178500 A1    Jul. 11, 2013

Related U.S. Application Data

(63) Continuation of application No. PCT/CN2011/070741, filed on Jan. 28, 2011.

(30) Foreign Application Priority Data

May 24, 2010    (CN) .......................... 2010 1 0181149

(51) Int. Cl.
*C07D 487/04*    (2006.01)
(52) U.S. Cl.
USPC ......... 514/338; 514/412; 546/276.7; 548/453
(58) Field of Classification Search
CPC ............................ C07D 487/04; A61K 31/395
USPC ................ 514/338, 412; 546/276.7; 548/453
See application file for complete search history.

(56) References Cited

U.S. PATENT DOCUMENTS

2007/0197563 A1*   8/2007   Schoenafinger et al. .. 514/263.2

FOREIGN PATENT DOCUMENTS

| CN | 101318925 A | 12/2008 |
|----|-------------|---------|
| WO | 2004103276 A2 | 12/2004 |
| WO | 2005116029 A1 | 12/2005 |
| WO | 2006099940 A1 | 9/2006 |
| WO | 2007077508 A2 | 7/2007 |

OTHER PUBLICATIONS

International Search Report & Written Opinion of the International Searching Authority Application No. PCT/CN2011/070741 Completed: Mar. 28, 2011; Mailing Date: May 5, 2011 9 pages.

* cited by examiner

*Primary Examiner* — Savitha Rao
*Assistant Examiner* — Angela Brown-Pettigrew
(74) *Attorney, Agent, or Firm* — St Onge Steward Johnston & Reens LLC

(57) ABSTRACT

Hexahydropyrrolo[3,4-b]pyrrole derivatives, preparation methods and pharmaceutical uses thereof are provided. Specifically, dipeptidyl peptidase IV inhibitors presented by following formula (I) are provided. Such compounds can be used for treating or preventing the diseases associated with dipeptidyl peptidase IV, such as diabetes, obesity and hyperlipemia. The compounds presented by formula (I) and pharmaceutically acceptable salts thereof, a method for preparing a pharmaceutical composition thereof and their uses in the manufacture of medicaments for treating or preventing the disease associated with dipeptidyl peptidase IV are provided.

(I)

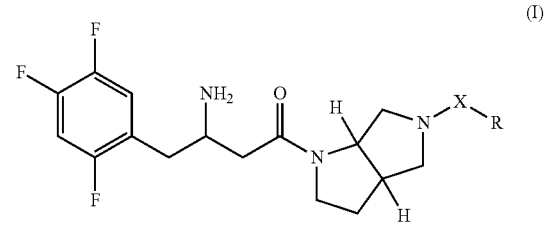

11 Claims, No Drawings

HEXAHYDROPYRROLO[3,4-B]PYRROLE DERIVATIVES, PREPARATION METHODS AND PHARMACEUTICAL USES THEREOF

FIELD OF THE INVENTION

The present invention relates to a new type of hexahydropyrrolo[3,4-b]pyrrole derivatives which are inhibitors of dipeptidyl peptidase IV (DPP-IV). The present invention also relates to the preparation methods of said derivatives and their uses in the treatment and prevention of diseases associated with dipeptidyl peptidase IV such as diabetes (particularly type II diabetes), obesity and hyperlipemia. This invent further relates to the compositions of these derivatives and the uses of said compositions in the treatment or prevention of diseases associated with dipeptidyl peptidase IV.

BACKGROUND OF THE INVENTION

Diabetes mellitus is a type of metabolic disorder of carbohydrates, fat and protein due to lack of insulin or insulin resistance and a group of clinical syndromes mainly characterized by chronic hyperglycemia (blood-fasting glucose concentration>130 mg/dL) and glycosuria. Sustained hyperglycemia would cause the occurrence of many complications, such as retinopathy, renal lesions, nervous system lesions and blood vessel complication, in which cardiovascular complications are especially major cause leading to death or disability of diabetes patients, thus controlling the blood glucose level of patient is very important for delaying or blocking the occurrence of complications.

Diabetes type II is one type of common chronic disease mainly characterized by hyperglycemia which occurs accompanying insulin resistance, relative decrease of insulin secretion inside body and increase of liver glyconeogenesis [Exp. Opin. Ther. Patents, 2003, 13(4):99-51].

At present, the drugs for treating diabetes type II mainly include insulin, biguanide such as metformin, sulfonylurea such as glimepiride, a glycosidase inhibitors such as acarbose, repaglinides such as rosiglitazone. But in addition to limited therapeutic effect, all these drugs poss apparent adverse effects.

So, there exists an urgent need to develop a novel, more effective and safer drug for treating diabetes. Many new treating targets are under study in which the results from pharmaceutical study with dipeptidyl peptidase IV (DPP-IV) as target are particularly excellent [medicinal research Review, 2009, 29(1), 125-195].

Glucagon-like peptide-1 (GLP-1) is secreted by pancreatic islet α cells and intestinal L cells which can glucose-dependently increase the secretion of insulin and enhance the biosynthesis of insulin, so the use of GLP-1 to treat diabetes caused great interests of scientists. In addition to enhancing insulin secretion, GLP-1 also has many physiological functions such as facilitating the proliferation of β cells, preventing apoptosis of β cells, inhibiting the production of glucagon and glycogen, controlling appetite, decreasing the speed of gastrointestinal emptying, protecting nerve cells and the like [Trends Endocrinol Metab, 1999, 10(6):229-235]. GLP-1 is a polypeptide containing 30 amino acids, glucose and fat can simulate its release. These properties of GLP-1 make it an ideal diabetic drug. Continuous i.v. drip of GLP-1 can decrease the blood glucose level of patient, even being effective for patients failed by sulfonylurea therapy, but single subcutaneous injection is ineffective, and continuous subcutaneous injection for 6 weeks would give ideal outcomes. The cause of this phenomenon is that the half life of GLP-1 in vivo is only several minutes and GLP-1 could be rapidly degradated by endogenous dipeptidyl peptidase (DPP-IV) and lose its activity of enhancing insulin secretion by cutting N-terminal dipeptide [Expert Opin. Investing. Drugs, 2004, 13(9): 1091-1102]. DPP-IV generally distributes in body and is major metabolic enzyme of GLP-1 which plays an important role in regulating activity of GLP-1. So, active compounds which can inhibit DPP-I, i.e., DPPIV inhibitors could enhance the effects of GLP-1 (intestinal glucokinin) and is intend to be a novel therapeutic drug for type 2 diabetes.

In addition, DPP-IV inhibitor also has many functions such as facilitating the proliferation of β cells, preventing apoptosis of β cells, inhibiting the production of glucagon and glycogen, suppressing appetite, not increasing body weight, decreasing the speed of gastrointestinal emptying, protecting nerve cells and the like [Trends Endocrinol Metab, 1999, 10(6):229-235]. So, DPP-IV inhibitor also can be used to treat various diseases associated with dipeptidyl peptidase such as obesity and hyperlipemia [Diabetologia, 2007, 50(6): 1148-1155; Regul Pept, 2008, 31(1):108-113].

Existing references and patents disclosed a lot of DPP-IV inhibitors [Current Medicinal Chemistry, 1999, 6, 311-327; Biochemistry 1999, 38, 11597-11603; Expert Opin. Ther. Patents, 2003, 13(4):499-510; Expert Opin. Investing. Drugs, 2005, 15(10):1387-1407]. WO 00/34241 disclosed N-substituted-2-cyanopyrroleidines compounds having DPP-IV inhibiting activity in which adamantine moiety is mon-substituted or simply alkyl-substituted. US 2003/0100563 disclosed β-amino heterocyclic DPP-IV inhibitors for diabetes treatment. WO 03/057666 disclosed cyclopropanated 2-cyanopyrroles DPP-IV inhibitors. US 2004/0171848 disclosed a series of 2-cyanopyrrole compounds containing diphenyl side chain. WO 2005/095381 disclosed a type of 2,4-dioxy-3,4-dihydropyrimidines DPP-IV inhibitors with new structure.

DPP-IV inhibitor Sitagliptin (MK-0431) and Vildagliptin (LAF-237) cameto market in USA and Europe respectively which were used to treat diabetes.

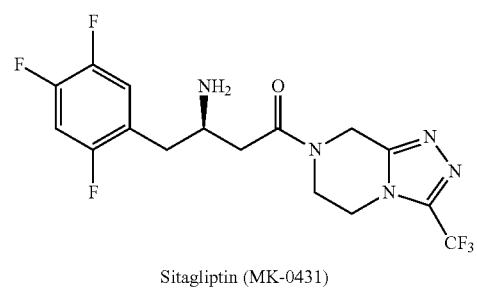

Sitagliptin (MK-0431)

Vildagliptin (LAF-237)

However, among the existing technologies, the inhibiting activity of these compounds against dipeptidyl peptidase is not satisfying and their ability to decrease blood glucose level and $HbAI_c$ is lower than that of metformin [Medicinal Research Review, 2009, 29(1), 125-195]. In view of this, there exists an urgent need in the art to develop an inhibitor of dipeptidyl peptidase with higher activity and selectivity in order to treat various diseases associated with dipeptidyl peptidase (DPP-IV).

SUMMARY OF THE INVENTION

The object of the present invention is to provide a type of novel dipeptidyl peptidase IV (DPP-IV) inhibitors, preparation methods and uses thereof.

In the first aspect of the present invention, a compound of formula (I), or various optical isomers, various crystal forms, pharmaceutically acceptable inorganic or organic salts, hydrates or solvates thereof are provided;

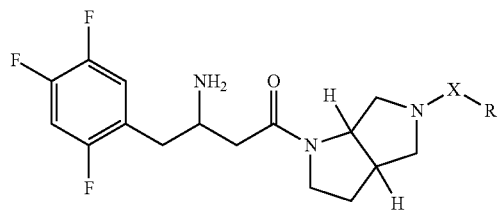

(I)

wherein,
X is selected from the following groups:
(1) —$C_1$-$C_3$ alkylidene;
(2) —C(O)—;
(3) —S(O)$_2$—;
(4) —C(O)O—;
(5) —C(O)NR$^1$—;
R is selected from the following groups:
(1) H;
(2) $C_1$-$C_6$ alkyl, which is unsubstituted or substituted by one to three substituents selected from the following group: fluorine, chlorine or hydroxyl;
(3) $C_3$-$C_6$ cycloalkyl, which is unsubstituted or substituted by one to two substituents selected from the following group: $C_1$-$C_3$ alkyl, fluorine, chlorine, hydroxyl, cyano, C(O)NH$_2$;
(4) Phenyl, which is unsubstituted or substituted by one to three substituents selected from the following group consisting of: $C_1$-$C_3$ alkyl, fluorine, chlorine, cyano, S(O)$_2$R$^2$;
(5) 6-membered heterocycle containing 1-2 atoms independently selected from N atoms, above-mentioned 6-membered heterocycle is unsubstituted or substituted by one to three substituents independently selected from the followings: $C_1$-$C_3$ alkyl, fluorine, chlorine, cyano, S(O)$_2$R$^2$;
Wherein, R$^1$ represents H or $C_1$-$C_3$ alkyl;
R$^2$ is $C_1$-$C_3$ alkyl.

In another preferred example, the present invention provides stereochemically preferred compound of general formula (Ia).

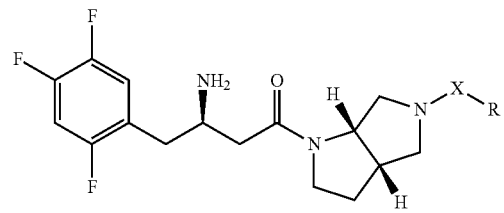

(Ia)

wherein,
X is selected from the following groups:
(1) —$C_1$-$C_3$ alkylidene;
(2) —C(O)—;
(3) —S(O)$_2$—;
(4) —C(O)O—;
(5) —C(O)NR$^1$—;
R is selected from the following groups:
(1) H;
(2) $C_1$-$C_6$ alkyl, which is unsubstituted or substituted by one to three substituents selected from the following group: fluorine, chlorine or hydroxyl;
(3) $C_3$-$C_6$ cycloalkyl, which is unsubstituted or substituted by one to two substituents selected from the following group: $C_1$-$C_3$ alkyl, fluorine, chlorine, hydroxyl, cyano, C(O)NH$_2$;
(4) Phenyl, which is unsubstituted or substituted by one to three substituents selected from the following group: $C_1$-$C_3$ alkyl, fluorine, chlorine, cyano, S(O)$_2$R$^2$;
(5) 6-membered heterocycle containing 1-2 atoms independently selected from N atoms, above-mentioned 6-membered heterocycle is unsubstituted or substituted by one to three substituents selected from the followings: $C_1$-$C_3$ alkyl, fluorine, chlorine, cyano, S(O)$_2$R$^2$;
wherein, R$^1$ represents H or $C_1$-$C_3$ alkyl;
R$^2$ is $C_1$-$C_3$ alkyl.

In another preferred example, the present invention provides salt forms of compounds of general formula (Ia), such as general formula (Ib);

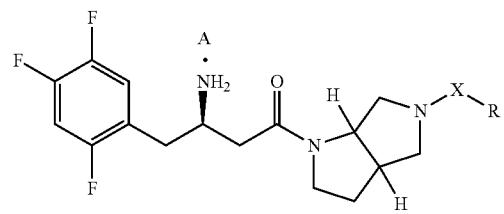

(Ib)

wherein, A is selected from acid radical (part of anions) of hydrochloric acid, hydrobromic acid, hydrofluoric acid, sulfuric acid, nitric acid, phosphoric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, benzenesulfonic acid, aspartic acid, glutamic acid, etc. In another preferred example, said salts are preferably selected from hydrochloric acid, phosphoric acid, methanesulfonic acid, fumaric acid.

The compounds of the prevent invention contain 3 asymmetric carbon atoms, so formula (I) includes single optically active form, single enantiomer, single diastereomer, mixture of diastereomer and mixture of racemates.

In another preferred example, said X is selected from —C(O)—

In another preferred example, said R is selected from: C1-C6 alkyl, which is unsubstituted or substituted by one to three substituents selected from the following group consisting of: fluorine, chlorine or hydroxyl; and C3-C6 cycloalkyl, which is unsubstituted or substituted by one to two substituents selected from the following group: $C_1$-$C_3$ alkyl, fluorine, chlorine, hydroxyl, cyano, $C(O)NH_2$.

In another preferred example, said R1 is H or unsubstituted $C_1$-$C_3$ alkyl.

In another preferred example, said R2 is unsubstituted $C_1$-$C_3$ alkyl.

In another preferred example, said compound is selected from the following group: compounds shown in table 1 or salts thereof.

In the second aspect of the present invention, a pharmaceutical composition is provided, which comprises pharmaceutically acceptable excipients or carriers and above-mentioned compounds of the present invention, or various optical isomers, various crystal forms, pharmaceutically acceptable inorganic or organic salts, hydrates or solvates thereof.

In the third aspect of the present invention, it provides the uses of above-mentioned compounds of the present invention, or various optical isomers, various crystal forms, pharmaceutically acceptable inorganic or organic salts, hydrates or solvates thereof, which can be used for manufacturing of DPP-IV inhibitors.

In the forth aspect of the present invention, it provides the uses of above-mentioned compounds of the present invention, or various optical isomers, various crystal forms, pharmaceutically acceptable inorganic or organic salts, hydrates or solvates thereof, which can be used to for the manufacturing of a medicament for the treatment, prevention and remission of diseases associated with DPP-IV.

In another preferred example, said diseases associated with DPP-IV are selected from diabetes, obesity and hyperlipemia.

In the fifth aspect of the present invention, it provides a method for manufacturing above-mentioned compounds of the present invention, or various optical isomers, various crystal forms, pharmaceutically acceptable salts, hydrates or solvates thereof, wherein, said method includes the following steps:

(a) In the inert solvents, compound of formula (1c) is brought to react with compound of formula (1d) under the condition of peptide coupling to give the compound of formula (1e),

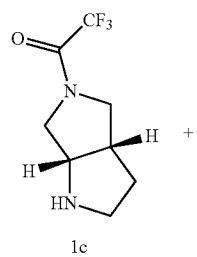

1c

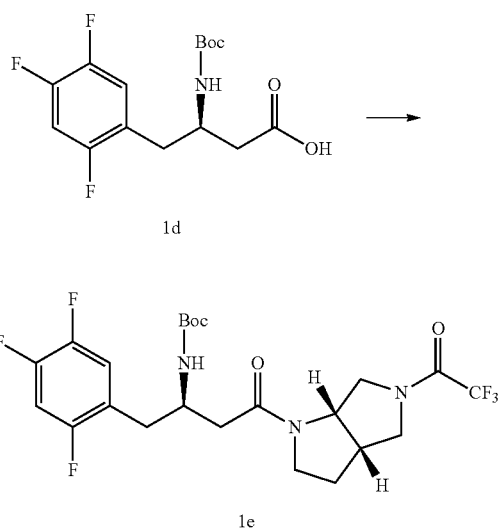

1d

1e (b) In the inert solvents, compound of formula 1e is brought to take off trifluoroacetyl protecting group under basic condition to give compound of formula (1f),

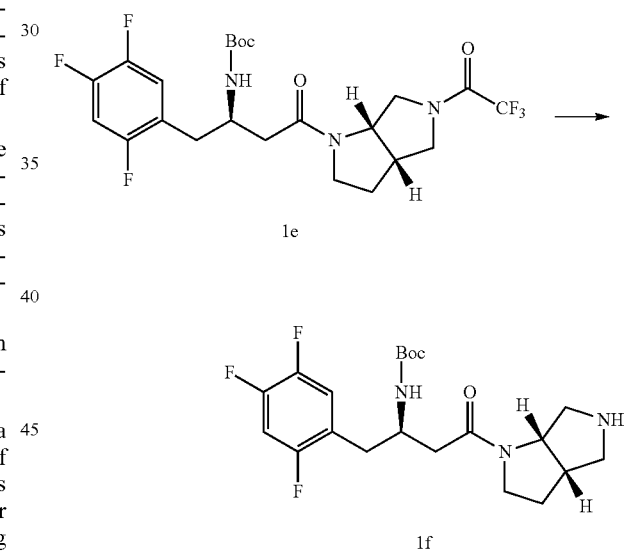

1e

1f (c) In the inert solvents, compound of formula 1f is brought to to give compound of formula (1g) by coupling reaction or acylation reaction,

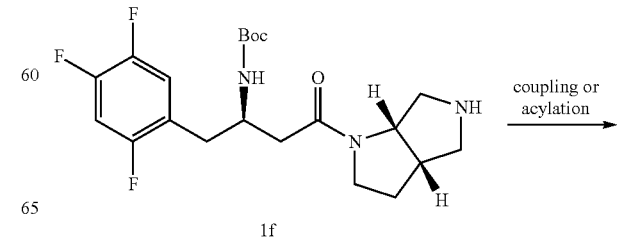

1f

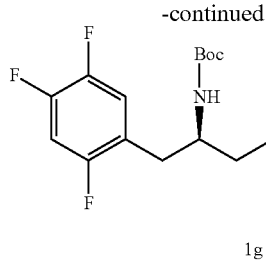

1g (d) In the inert solvents, compound of formula (Ia) is produced by taking off protecting group in the presence of acid;

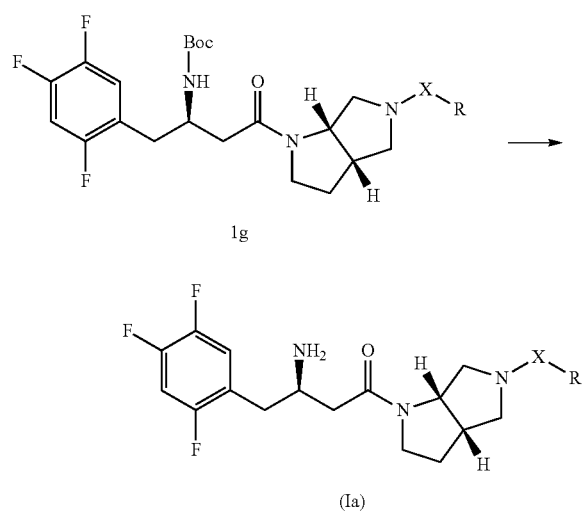

In the above formulas,
X is selected from the following groups:
(1) —$C_1$-$C_3$ alkylidene;
(2) —C(O)—;
(3) —S(O)$_2$—;
(4) —C(O)O—;
(5) —C(O)NR$^1$—;
R is selected from the following groups:
(1) H;
(2) $C_1$-$C_6$ alkyl, which is unsubstituted or substituted by one to three substituents selected from the following group: fluorine, chlorine or hydroxyl;
(3) $C_3$-$C_6$ cycloalkyl, which is unsubstituted or substituted by one to two substituents selected from the following group: $C_1$-$C_3$ alkyl, fluorine, chlorine, hydroxyl, cyano, C(O)NH$_2$;
(4) Phenyl, which is unsubstituted or substituted by one to three substituents selected from the followings: $C_1$-$C_3$ alkyl, fluorine, chlorine, cyano, S(O)$_2$R$^2$;
(5) 6-membered heterocycle containing 1-2 atoms independently selected from N atoms, above-mentioned 6-membered heterocycle is unsubstituted or substituted by one to three substituents selected from the followings: $C_1$-$C_3$ alkyl, fluorine, chlorine, cyano, S(O)$_2$R$^2$;
wherein, R$^1$ represents H or $C_1$-$C_3$ alkyl;
R$^2$ is $C_1$-$C_3$ alkyl.
In another preferred example, said method further includes step (e) which is to make compound of formula (Ia) react with acid HA to give the salt form (Ib) of (Ia):

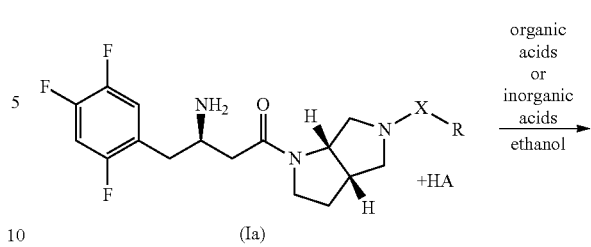

wherein, A represents acid radical of inorganic or organic acid.

In another preferred example, said method includes: in the inert solution and under standard peptide coupling condition, compound of formula 1c is brought to react with compound of formula 1d, and then takes off trifluoroacetyl under basic condition, coupling, takes off Boc protecting group under acidic condition to give compound of formula (Ia), then forms salt with acid to generate formula (Ib).

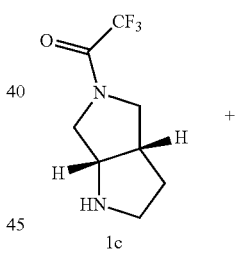

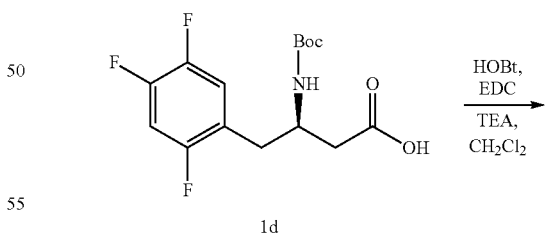

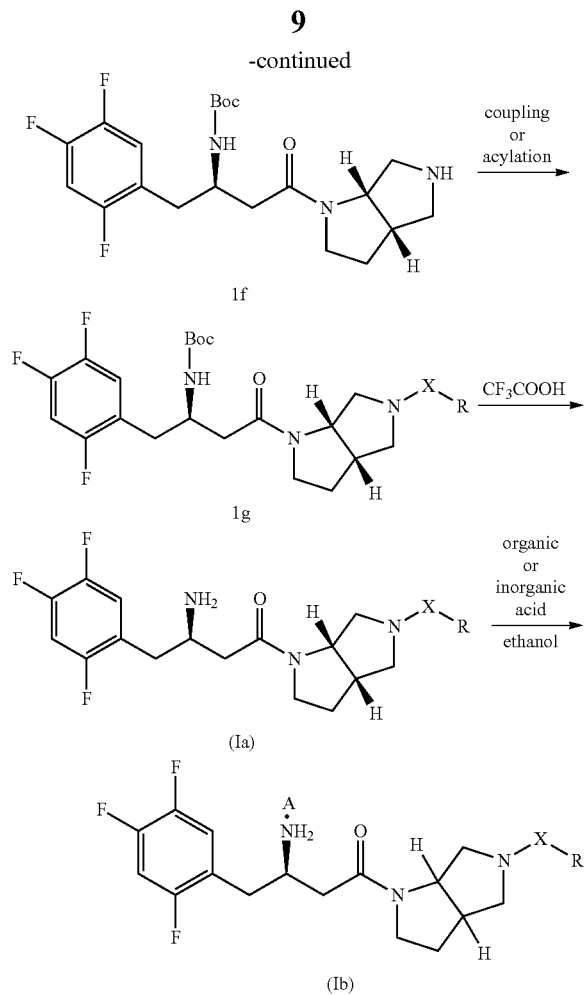

wherein, R, A and X are described as above.

DETAILED DESCRIPTION OF THE INVENTION

The present inventors synthesized a large number of compounds by broad and thorough researches and extensive structure-effect relationship investigations, and performed a lot of systematic research work such as in vitro screening, selectivity, metabolism, jin vivo glucose-decreasing activity, discovered firstly that the compound of formula (I) had strong inhibiting activity against DPP-IV, particularly suitable as DPP-IV inhibitor. The present inventor accomplished the present invention on this basis.

Definitions

Unless specifically stated, the following terms used in the specification and claims have the meanings as follows:

"Alkyl" refers to saturated aliphatic hydrocarbon groups, including straight-chain and branched-chain groups of 1 to 6 carbon atoms. Medium size of alkyl containing 1-6 carbon atoms is preferred, such as methyl, ethyl, propyl, 2-propyl, n-butyl, isobutyl, tert-butyl, 2,2-dimethylpropyl, phenyl, etc. Lower alkyl containing 1 to 4 carbon atoms are more preferred, such as methyl, ethyl, propyl, 2-propyl, n-butyl, isobutyl, tert-butyl, etc.

"Alkylidene" refers to a straight or branched divalent hydrocarbon chain containing 1-6 carbon atoms. Medium size of alkylidene containing 1-6 carbon atoms is preferred, such as methylidene, ethylidene, propylidene.

"Cycloalkyl" refers 3 to 8 membered full carbon monocyclic, 5/6 membered or 6/6 membered full carbon fused ring or multicyclic fused ring group, wherein one or more rings can contain one or more double bonds, but none of them has full conjugated π-electron system. Examples of cycloalkyl include cyclopropyl, cyclobutyl, cyclopentyl, cyclohexane, cyclohexadiene, adamantane, cycloheptane, cycloheptatriene and the like. Cyclopropyl and cyclobutyl are more preferred.

"Phenyl" refers to a group containing at least one aromatic ring, i.e., aromatic ring containing conjugated π-electron system, including carbocyclic aryl, heteroaryl.

"Heterocycle" refers to aryl containing 1-3 heteroatoms as ring atoms and other ring atoms being carbon, heteroatom includes O, S and N. Said ring may be a 5 or 6 membered ring. Examples of heterocyclic aryl group include but not limited to furyl, thienyl, pyridyl, pyrrole, N-alkylpyrrolyl, pyrimidinyl, pyrazinyl, imidazolyl, pyrazolyl, oxazolyl, isooxazolyl, thiazolyl, triazolyl, triazinyl and like.

Active Ingredients

As used herein, "compound of the present invention" means compound of formula (I). This term also includes various crystal forms, pharmaceutically acceptable inorganic or organic salts, hydrates or solvates of compound of formula (I).

The compounds of the present invention can contain one or more asymmetric centres, and thus exist as the form of racemate, racemic mixture, individual enantiomer, diastereoisomer compound and individual diastereomer. The asymmetric centres which can exist are dependent on the properties of various substituents on molecule. Each of such asymmetric centres will independently produce two optical isomers, and all possible optical isomers and diastereomer mixture as well as pure or partially pure compounds are included in the scope of the invention. The present invention is intended to include all such isomeric forms of these compounds.

The compounds of the present invention have one or more asymmetric carbon atoms, so formula (I) includes racemate, racemic mixture, individual enantiomer, diastereoisomer compound and individual diastereomer.

As used herein, "pharmaceutically acceptable salts" means no limitation as long as salts are pharmaceutically acceptable. In particular, the salts formed with acid can be listed. Suitable salt-forming acids include (but not limited to) hydrochloric acid, hydrobromic acid, hydrofluoric acid, sulfuric acid, nitric acid, phosphoric acid, and other inorganic acids, formic acid, acetic acid, propionic acid, oxalic acid, malonic acid, succinic acid, fumaric acid, maleic acid, lactic acid, malic acid, tartaric acid, citric acid, picric acid, methanesulfonic acid, benzenesulfonic acid, and other organic acids as well as aspartic acid, glutamic acid and other acidic amino acids.

The name and structural formula of representative compounds in the compound of formula (I) of the present invention are shown as below:

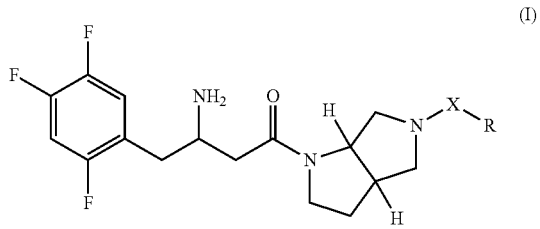

(I)

TABLE 1

The compounds of the present invention have the following structural formula

| compound | compound structure | compound name |
|---|---|---|
| 1 | 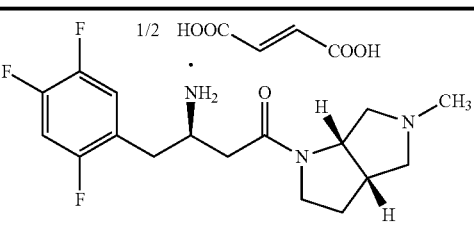 | (R)-3-amino-1-((3aS,6aS)-hexahydro-5-methylpyrrolo[3,4-b]pyrrol-1(2H)-yl)-4-(2,4,5-trifluorophenyl)but-1-anone fumarate |
| 2 | 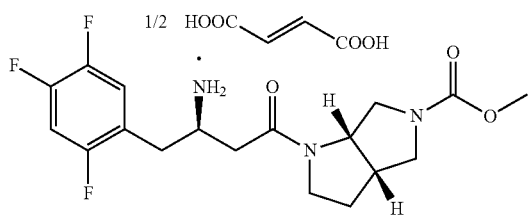 | (R)-3-amino-1-((3aS,6aS)-5-methoxycarbonylhexahydropyrrolo[3,4-b]pyrrol-1(2H)-yl)-4-(2,4,5-trifluorophenyl)but-1-anone fumarate |
| 3 | 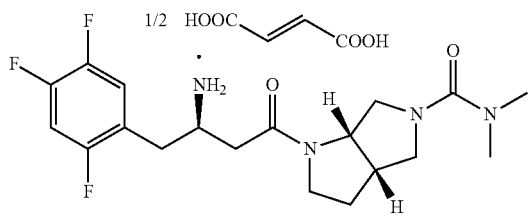 | (R)-3-amino-1-((3aS,6aS)-5-(N,N-dimethylaminoformyl)-hexahydropyrrolo[3,4-b]pyrrol-1(2H)-yl)-4-(2,4,5-trifluorophenyl)butane-1-one fumarate |
| 4 | 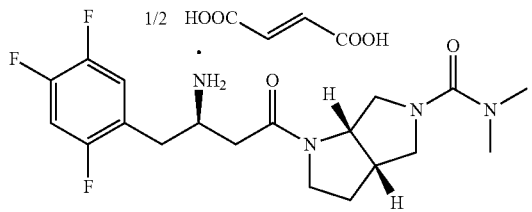 | (R)-3-amino-1-((3aS,6aS)-5-(N-methylaminoformyl)-hexahydropyrrolo[3,4-b]pyrrol-1(2H)-yl)-4-(2,4,5-trifluorophenyl)butane-1-one fumarate |
| 5 | 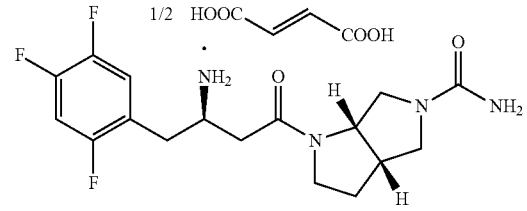 | (R)-3-amino-1-((3aS,6aS)-5-(methylaminoformyl)-hexahydropyrrolo[3,4-b]pyrrol-1(2H)-yl)-4-(2,4,5-trifluorophenyl)butane-1-one fumarate |
| 6 | 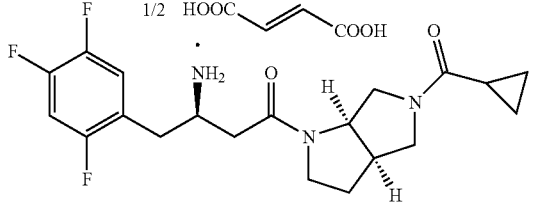 | (R)-3-amino-1-((3aS,6aS)-5-(cyclopropcarbonyl)-hexahydropyrrolo[3,4-b]pyrrol-1(2H)-yl)-4-(2,4,5-trifluorophenyl)butane-1-one fumarate |
| 7 | 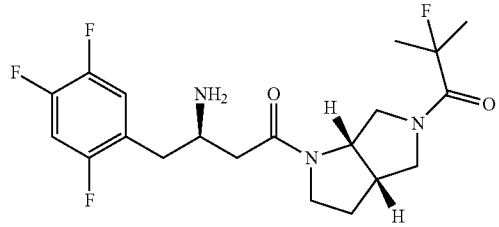 [SMILES: CC(C)(F)C(=O)N1C[C@@H]2CCN(C(=O)C[C@H](N)Cc3cc(F)c(F)cc3F)[C@@H]2C1] | (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butane-1-one |

TABLE 1-continued

The compounds of the present invention have the following structural formula

| compound | compound structure | compound name |
|---|---|---|
| 8 | 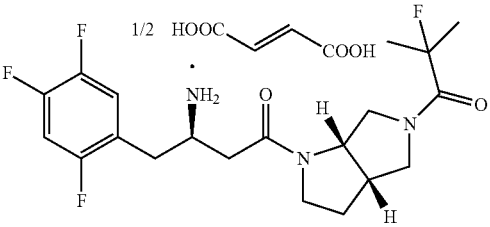 | (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butane-1-one fumarate |
| 9 | 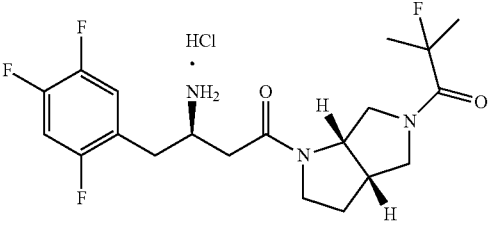 | (R)-3-amino-1-((3aS,6aS)-5-(2-fluoro-2-methylpropionyl)-hexapyrrolo[3,4-b]pyrrol-1(2H)-yl)-4-(2,4,5-trifluorophenyl)butane-1-one hydrochloride |
| 10 | 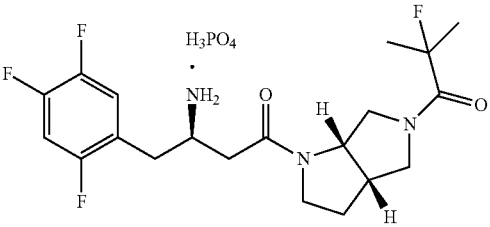 | (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butane-1-one phosphate |
| 11 | 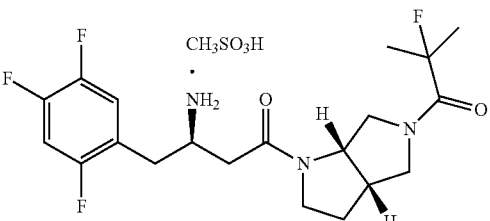 | (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butane-1-one methane sulfonate |
| 12 | 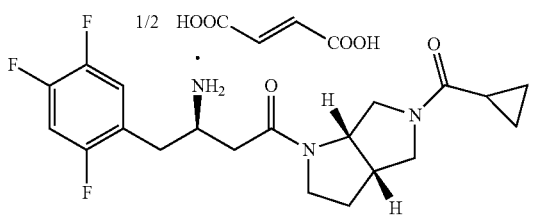 | (R)-3-amino-1-((3aS,6aS)-5-(cyclopropcarbonyl)-hexahydropyrrolo[3,4-b]pyrrol-1(2H)-yl)-4-(2,4,5-trifluorophenyl)butane-1-one fumarate |
| 13 | 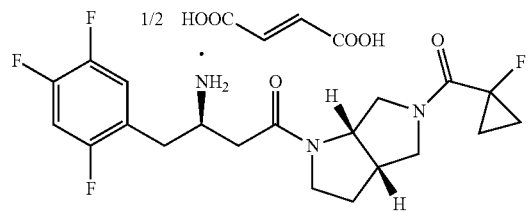 | (R)-3-amino-1-((3aS,6aS)-5-(1-fluorocyclopropylcarbonyl)-hexahydropyrrolo[3,4-b]pyrrol-1(2H)-yl)-4-(2,4,5-trifluorophenyl)butane-1-one fumarate |

TABLE 1-continued

The compounds of the present invention have the following structural formula

| compound | compound structure | compound name |
|---|---|---|
| 14 | 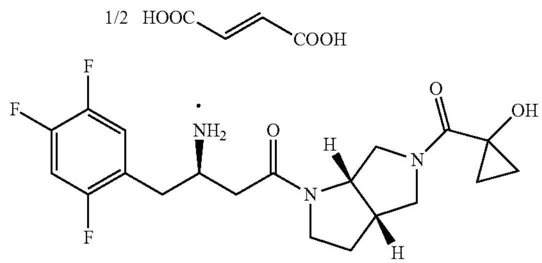 | (R)-3-amino-1-((3aS,6aS)-5-(1-hydroxylcyclopropylcarbonyl)-hexahydropyrrolo[3,4-b]pyrrol-1(2H)-yl)-4-(2,4,5-trifluorophenyl)butane-1-one fumarate |
| 15 | 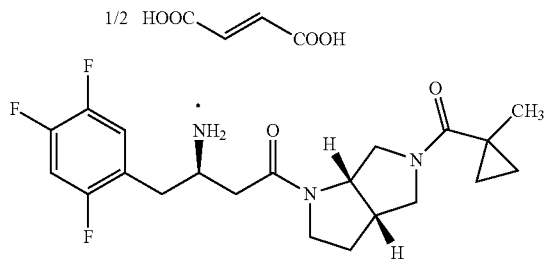 | (R)-3-amino-1-((3aS,6aS)-5-(1-methylcyclopropylcarbonyl)-hexahydropyrrolo[3,4-b]pyrrol-1(2H)-yl)-4-(2,4,5-trifluorophenyl)butane-1-one fumarate |
| 16 | 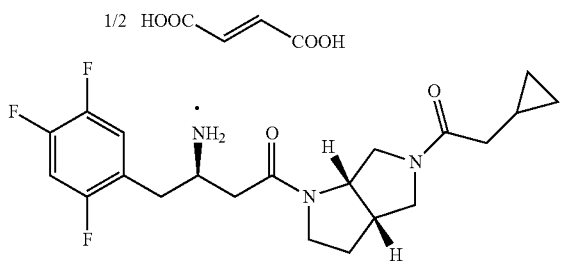 | (R)-3-amino-1-((3aS,6aS)-5-(cyclopropylmethylidenecarbonyl)-hexahydropyrrolo[3,4-b]pyrrol-1(2H)-yl)-4-(2,4,5-trifluorophenyl)butane-1-one fumarate |
| 17 | 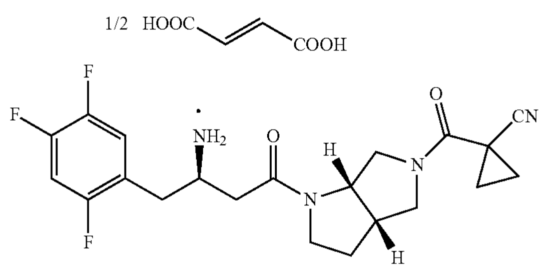 | (R)-3-amino-1-((3aS,6aS)-5-(1-cyanocyclopropylcarbonyl)-hexahydropyrrolo[3,4-b]pyrrol-1(2H)-yl)-4-(2,4,5-trifluorophenyl)butane-1-one fumarate |
| 18 | 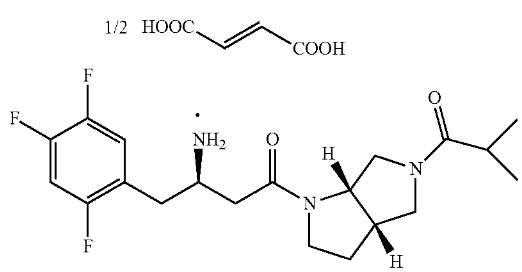 | (R)-3-amino-1-((3aS,6aS)-5-(isopropylcarbonyl)-hexahydropyrrolo[3,4-b]pyrrol-1(2H)-yl)-4-(2,4,5-trifluorophenyl)butane-1-one fumarate |

TABLE 1-continued

The compounds of the present invention have the following structural formula

| compound | compound structure | compound name |
|---|---|---|
| 19 | 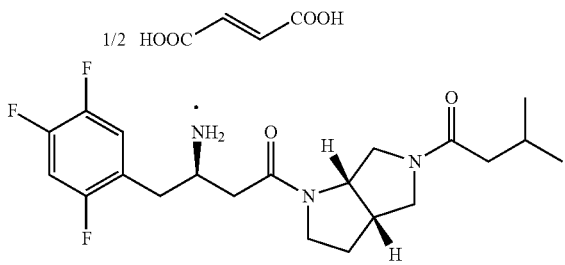 | (R)-3-amino-1-((3aS,6aS)-5-(3-methylbutyryl)-hexahydropyrrolo[3,4-b]pyrrol-1(2H)-yl)-4-(2,4,5-trifluorophenyl)butane-1-one fumarate |
| 20 | 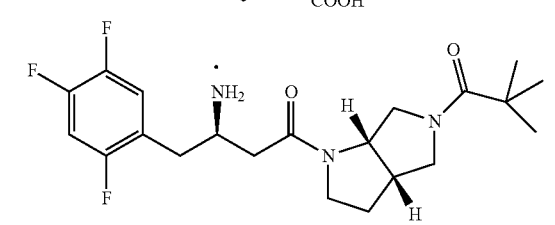 | (R)-3-amino-1-((3aS,6aS)-5-(tertvaleryl)-hexahydropyrrolo[3,4-b]pyrrol-1(2H)-yl)-4-(2,4,5-trifluorophenyl)butane-1-one fumarate |
| 21 | 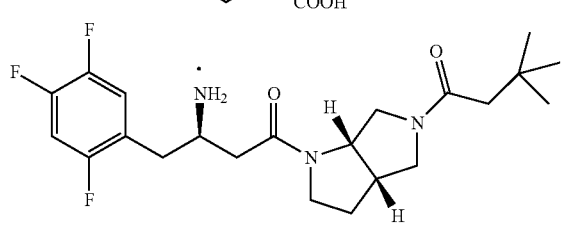 | (R)-3-amino-1-((3aS,6aS)-5-(3,3-dimethylbutyryl)-hexahydropyrrolo[3,4-b]pyrrol-1(2H)-yl)-4-(2,4,5-trifluorophenyl)butane-1-one fumarate |
| 22 | 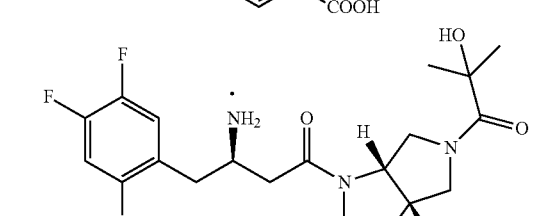 | (R)-3-amino-1-((3aS,6aS)-5-(2-hydroxyl-2-methylpropionyl)-hexahydropyrrolo[3,4-b]pyrrol-1(2H)-yl)-4-(2,4,5-trifluorophenyl)butane-1-one fumarate |
| 23 | 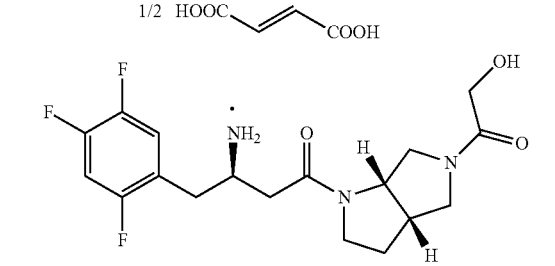 | (R)-3-amino-1-((3aS,6aS)-5-(hydroxylacetyl)-hexahydropyrrolo[3,4-b]pyrrol-1(2H)-yl)-4-(2,4,5-trifluorophenyl)butane-1-one fumarate |

TABLE 1-continued

The compounds of the present invention have the following structural formula

| compound | compound structure | compound name |
|---|---|---|
| 24 | 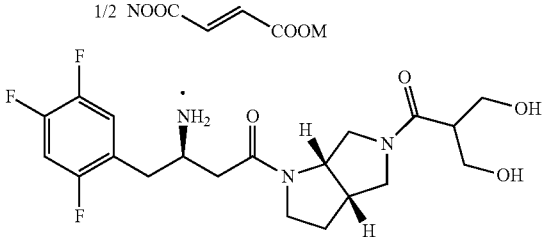 | (R)-3-amino-1-((3aS,6aS)-5-(1-hydroxymethyl2-hydroxypropionyl)-hexahydropyrrolo[3,4-b]pyrrol-1(2H)-yl)-4-(2,4,5-trifluorophenyl)butane-1-one fumarate |
| 25 | 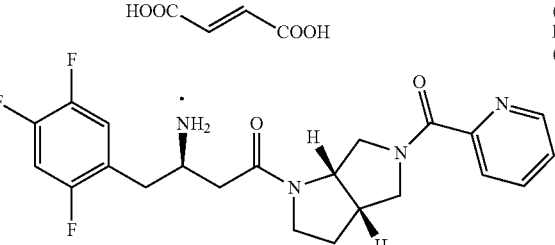 | (R)-3-amino-1-((3aS,6aS)-5-(pyrrol-2-yl)-hexahydropyrrolo[3,4-b]pyrrol-1(2H)-yl)-4-(2,4,5-trifluorophenyl)butane-1-one fumarate |
| 26 | 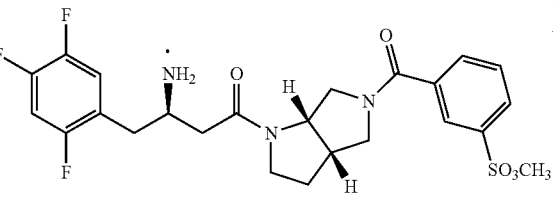 | (R)-3-amino-1-((3aS,6aS)-5-(3-mesylbenzoyl)-hexahydropyrrolo[3,4-b]pyrrol-1(2H)-yl)-4-(2,4,5-trifluorophenyl)butane-1-one fumarate |
| 27 | 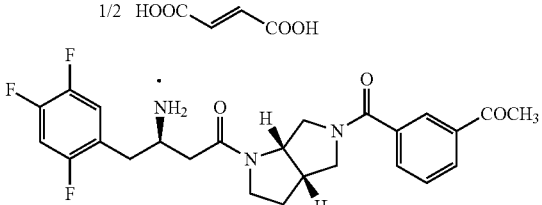 | (R)-3-amino-1-((3aS,6aS)-5-(3-acetylbenzoyl)-hexahydropyrrolo[3,4-b]pyrrol-1(2H)-yl)-4-(2,4,5-trifluorophenyl)butane-1-one fumarate |
| 28 | 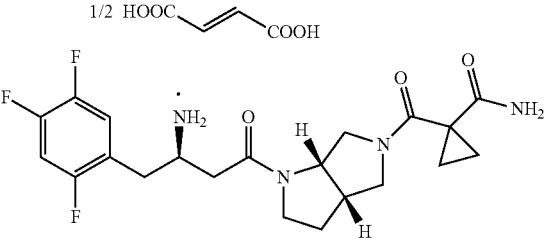 | (R)-3-amino-1-((3aS,6aS)-5-(1-aminocarbonylcyclopropylcarbonyl)-hexahydropyrrolo[3,4-b]pyrrol-1(2H)-yl)-4-(2,4,5-trifluorophenyl)butane-1-one fumarate |
| 29 | 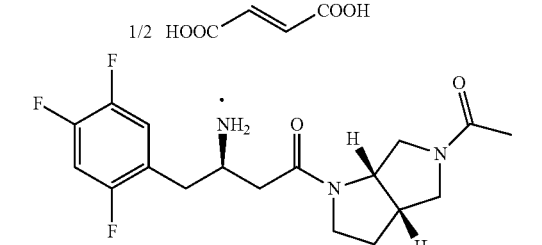 | (R)-3-amino-1-((3aS,6aS)-5-(acetyl)-hexahydropyrrolo[3,4-b]pyrrol-1(2H)-yl)-4-(2,4,5-trifluorophenyl)butane-1-one fumarate |

TABLE 1-continued

The compounds of the present invention have the following structural formula

| compound | compound structure | compound name |
|---|---|---|
| 30 | 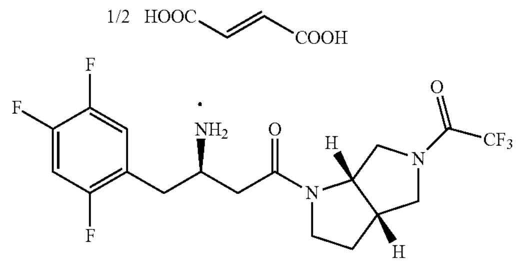 | (R)-3-amino-1-((3aS,6aS)-5-(trifluoroacetyl)-hexahydropyrrolo[3,4-b]pyrrol-1(2H)-yl)-4-(2,4,5-trifluorophenyl)butane-1-one fumarate |
| 31 | 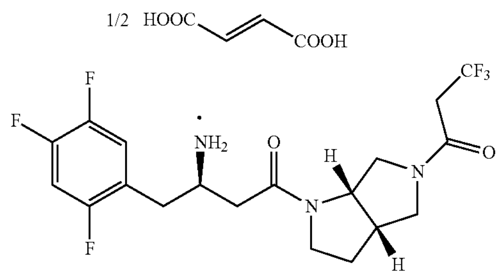 | (R)-3-amino-1-((3aS,6aS)-5-(3,3,3-trifluoropropionyl)-hexahydropyrrolo[3,4-b]pyrrol-1(2H)-yl)-4-(2,4,5-trifluorophenyl)butane-1-one fumarate |
| 32 | 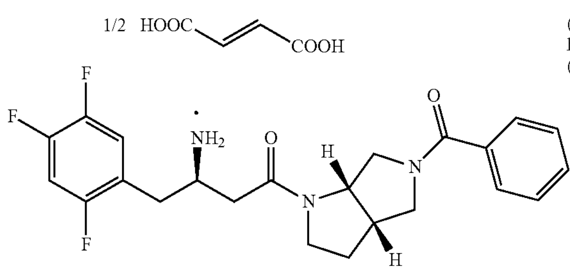 | (R)-3-amino-1-((3aS,6aS)-5-(benzoyl)-hexahydropyrrolo[3,4-b]pyrrol-1(2H)-yl)-4-(2,4,5-trifluorophenyl)butane-1-one fumarate |
| 33 | 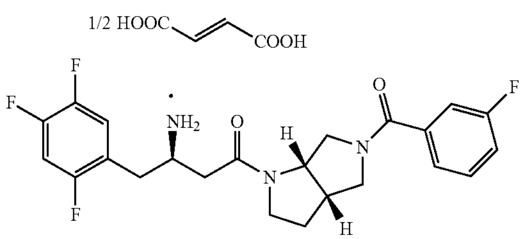 | (R)-3-amino-1-((3aS,6aS)-5-(3-fluorobenzoyl)-hexahydropyrrolo[3,4-b]pyrrol-1(2H)-yl)-4-(2,4,5-trifluorophenyl)butane-1-one fumarate |
| 34 | 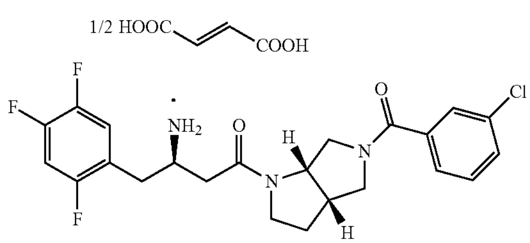 | (R)-3-amino-1-((3aS,6aS)-5-(3-chlorobenzoyl)-hexahydropyrrolo[3,4-b]pyrrol-1(2H)-yl)-4-(2,4,5-trifluorophenyl)butane-1-one fumarate |
| 35 | 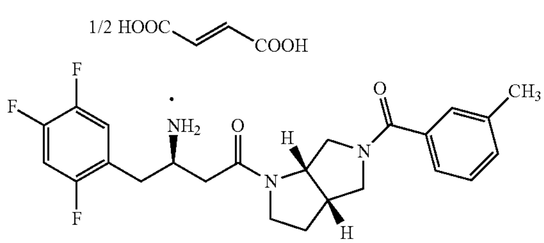 | (R)-3-amino-1-((3aS,6aS)-5-(3-methylbenzoyl)-hexahydropyrrolo[3,4-b]pyrrol-1(2H)-yl)-4-(2,4,5-trifluorophenyl)butane-1-one fumarate |

TABLE 1-continued

The compounds of the present invention have the following structural formula

| compound | compound structure | compound name |
|---|---|---|
| 36 | 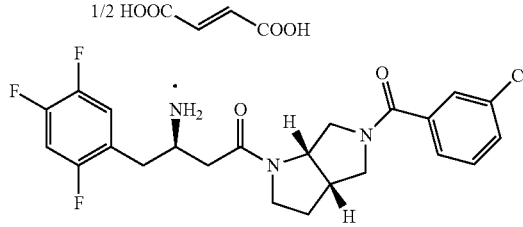 | (R)-3-amino-1-((3aS,6aS)-5-(3-cyanobenzoyl)-hexahydropyrrolo[3,4-b]pyrrol-1(2H)-yl)-4-(2,4,5-trifluorophenyl)butane-1-one fumarate |
| 37 | 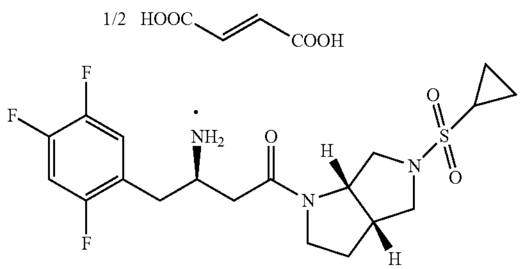 | (R)-3-amino-1-((3aS,6aS)-5-(cyclopropylsulfonyl)-hexahydropyrrolo[3,4-b]pyrrol-1(2H)-yl)-4-(2,4,5-trifluorophenyl)butane-1-one fumarate |
| 38 | 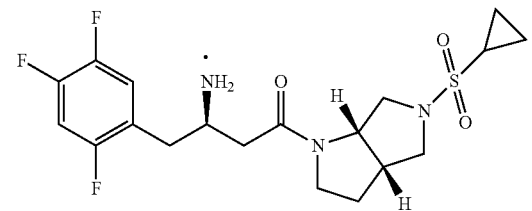 | (R)-3-amino-1-((3aS,6aS)-5-(mesyl)-hexahydropyrrolo[3,4-b]pyrrol-1(2H)-yl)-4-(2,4,5-trifluorophenyl)butane-1-one fumarate |
| 39 | 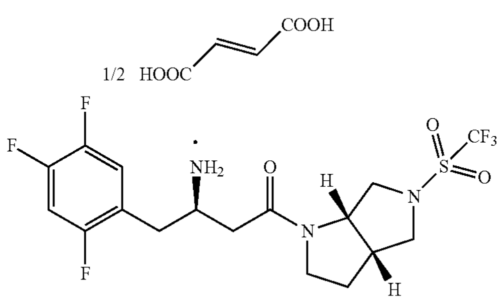 | (R)-3-amino-1-((3aS,6aS)-5-(trifluoromesyl)-hexahydropyrrolo[3,4-b]pyrrol-1(2H)-yl)-4-(2,4,5-trifluorophenyl)butane-1-one fumarate |
| 40 | 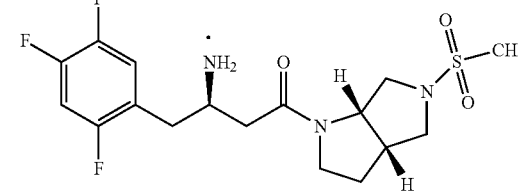 | (R)-3-amino-1-((3aS,6aS)-5-(benzenesulfonyl)-hexahydropyrrolo[3,4-b]pyrrol-1(2H)-yl)-4-(2,4,5-trifluorophenyl)butane-1-one fumarate |

TABLE 1-continued

The compounds of the present invention have the following structural formula

| compound | compound structure | compound name |
|---|---|---|
| 41 | 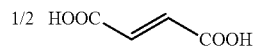 1/2 HOOC⤳COOH | (R)-3-amino-1-((3aS,6aS)-5-(p-tosyl)-hexahydropyrrolo[3,4-b]pyrrol-1(2H)-yl)-4-(2,4,5-trifluorophenyl)butane-1-one fumarate |

Preparation Methods

The preparation methods of the compounds of structural formula (I) of the invention are particularly described below, but these particular methods construct no limitation to the present invention. The conditions of such method e.g., reactant, solvent, base, the amount of used compounds, reaction temperature, time required by reaction and the like are not limited to the explanation below.

The compounds of the invention are also optionally easily produced by combing various synthesis methods described in the specification or known in the art. Such combination can be easily performed by the skill of the art belonging to the invention.

In the preparation methods of the invention, every reaction is often performed at the temperature from 0° C. to solvent's reflux temperature (preferably RT ~80° C.) in inert solvent. Reaction time is usually 0.1 hr~60 hrs, more preferably 0.5 hr~48 hrs.

In a preferred example, the compounds of formula (I) of the prevent invention can be prepared according to the following synthetic route:

Synthetic Route:

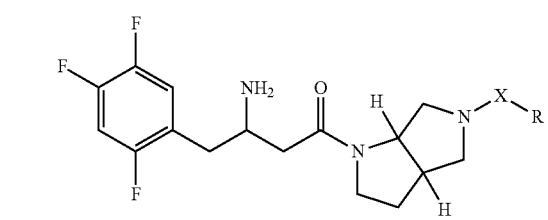

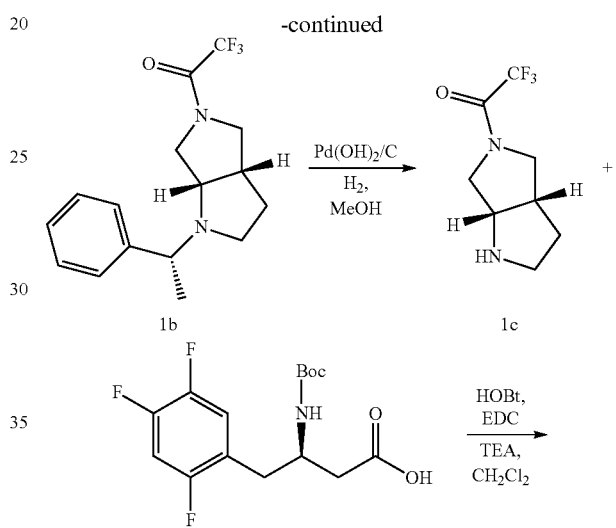

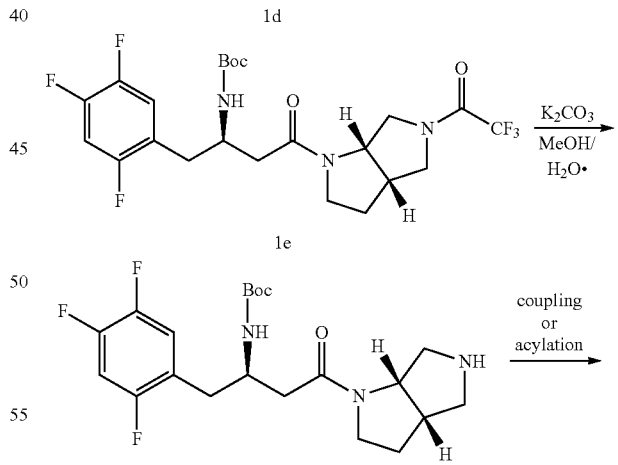

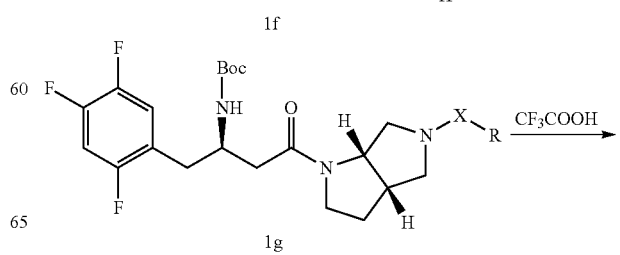

-continued

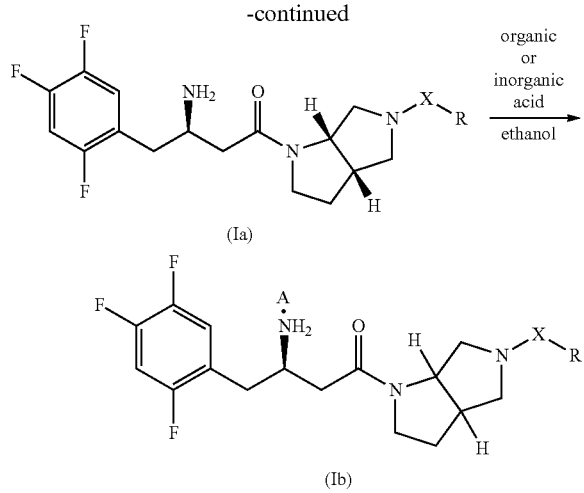

X, R and A are defined as described above.

(1) Compound 1a-1c can be prepared according to methods disclosed in patent [US20050101602].

(2) Compound 1d can be prepared according to methods disclosed in reference [*J. Med. Chem.* 2005, 48, 141].

(3) In the intert polar aprotic solvent, compound 1c can react with 1d under standard peptide coupling condition for 1-36 h, for example, by using 1-ethyl-3-(3-dimethylamino) carbodiimide and 1-hydroxylbenzotriazole (EDC/HOBT) or hexafluorophospho(7-azabenzotrizole-1-yl)-N,N,N',N'-tetramethylurea and 1-hydroxylazabenzotriazole, to give compound 1e. The reaction temperature is between −20-40° C. Polar aprotic solvent can include (but not limited to): dichloromethane, chloroform, 1,2-dichloroethane, ethyl acetate, tetrahydrofuran, diethyl ether, methyl tert-butyl ether, 1,6-dioxane, dimethylformamide, dimethyl sulfoxide, acetonitrile, and combination thereof. Preferred condition is to react for 12-24 hours at 20-40° C. in the presence of EDC/HOBT coupling agent with dichloromethane as solvent.

(4) Compound 1e reacts in the intert polar solvent for 1-36 hours at −20–40° C. in the presence of base to give compound 1f. Polar aprotic solvent can include (but not limited to): methanol, ethanol, isopropanol, water, tetrahydrofuran and the like; Base can include (but not limited to): potassium carbonate, sodium carbonate, sodium hydroxide, potassium hydroxide and the like. Preferred condition is to react in the mixed solvent of methanol and water for 12-24 hours at 20-40° C. by adding potassium carbonate.

(5) The synthesis of compound of formula IA can be prepared according to the methods as below.

Method 1: In the intert polar aprotic solvent, compound 1f can react under standard peptide coupling condition for 1-36 h, for example, by using 1-ethyl-3-(3-dimethylamino)carbodiimide and 1-hydroxylbenzotriazole (EDC/HOBT) or hexafluorophospho (7-azabenzotrizole-1-yl)-N,N,N',N'-tetramethylurea and 1-hydroxylazabenzotriazole, to give compound IA. The reaction temperature is between −20–40° C. Polar aprotic solvent can include (but not limited to): dichloromethane, chloroform, 1,2-dichloroethane, ethyl acetate, tetrahydrofuran, diethyl ether, methyl tert-butyl ether, 1,6-dioxane, dimethylformamide, dimethyl sulfoxide, acetonitrile, and the like. Preferred condition is to react for 12-24 hours at 20-40° C. in the presence of EDC/HOBT coupling agent with dichloromethane as solvent.

Method 2: In the intert polar protic solvent, compound 1f can react with various alkyl, aryl acyl chloride or anhydride at appropriate temperature in the presence of base to give compound Ig. Polar aprotic solvent can include (but not limited to): dichloromethane, chloroform, 1,2-dichloroethane, ethyl acetate, tetrahydrofuran, diethyl ether, methyl tert-butyl ether, 1,4-dioxane, dimethylformamide, dimethyl sulfoxide, acetonitrile, and the like. The reaction temperature is between 0~100° C. Base includes (but not limited to): imidazole, triethylamine, pyrrole, N-methylmorpholine, morpholine, N,N-diisopropylethylamine and the like; Preferred condition is to react for 12-24 hours at 20-40° C. with dichloromethane as solvent and triethylamine as base.

(6) In the intert polar aprotic solvent, compound Ig takes off protecting group to give compound of formula (I) in the presence of acid. Polar aprotic solvent can include (but not limited to): dichloromethane, chloroform, 1,2-dichloroethane, ethyl acetate, tetrahydrofuran, diethyl ether, methyl tert-butyl ether, 1,4-dioxane, dimethylformamide, dimethyl sulfoxide, acetonitrile, and the like. Acid includes (but not limited to): formic acid, acetic acid, trifluoroacetic acid, hydrochloric acid, methanesulfonic acid and the like. Preferred condition is to react for 0.5-2 hours at 20-40° C. with dichloromethane as solvent and adding trifluoroacetic acid.

(7) The methods of the prevent invention can optionally include salt-forming steps. For example, in the intert polar solvent, compound of formula (Ia) can form salt with acid to give formula (Ib). Polar solvent can include (but not limited to): polar solvent can be selected from methanol, ethanol, isopropanol, water, ethyl acetate, acetonitrile or the combination thereof. Acids can include (but not limited to) hydrochloric acid, hydrobromic acid, hydrofluoric acid, sulfuric acid, phosphoric acid, nitric acid and other inorganic acids, formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid, p-toluene sulfonic acid, and other organic acids as well as aspartic acid, glutamic acid and other acidic amino acids. Preferred acids are hydrochloric acid, phosphoric acid, formic acid, methanesulfonic acid and the like; Preferred condition is to react with preferred acid for 0.5~2 hours at 20-40° C.

(8) The synthesis of their enantiomers and diastereomer can be accomplished by choosing suitable chiral raw materials according to the above-mentioned preparation methods.

Pharmaceutical Compositions and Administration Methods

Since the compound of the present invention has superior DPP-IV-inhibiting activity, the compound of the present invention and various crystal forms, pharmaceutically acceptable inorganic or organic salts, hydrates or solvates thereof, as well as pharmaceutical compositions containing the compound of the present invention as main active ingredient can be used to treat, prevent and alleviate diseases associated with DPP-IV. According to the current techniques, the compound of the present invention can be used to teat type 2 diabetes, obesity, and hyperlipemia.

Pharmaceutical compositions of the present invention comprise safe and effective amount of the compound of the present invention or pharmaceutically acceptable salts and pharmaceutically acceptable excipients or carriers thereof. Wherein, "safe and effective amount" refers to: sufficient amount of compound to significantly improve disease condition without leading to serious adverse effect. Generally, pharmaceutical compositions contain 1-1000 mg compound of the present invention per dose, preferably 5-500 mg compound of the present invention per dose, more preferably 10-200 mg compound of the present invention per dose.

The compounds of the present invention and pharmaceutically acceptable salts thereof can be formulated into various formulations, which comprise safe and effective amount of the compound of the present invention or pharmaceutically acceptable salts and pharmacologically acceptable excipients or carriers thereof. Wherein, "safe and effective amount" refers to: sufficient amount of compound to significantly improve disease condition without leading to serious adverse effect. The safe and effective amount of the compound is determined based on the specific situations such as age, disease condition, treatment course of the subject to be treated.

"Pharmaceutically acceptable excipients or carriers" refers to: one or more compatible solid or liquid fillers or gel substances, they are suitable for human use and must have enough purity and sufficiently low toxicity. "Compatibility" herein means each component in the composition and the compound of the present invention can be incorporated into each other without significantly reducing the compound's pharmaceutical effect. Part examples of pharmacologically acceptable excipients or carriers are cellulose and its derivative (e.g., sodium carboxymethylcellulose, ethyl cellulose sodium, cellulose acetate, etc), gelatin, talc, solid lubricant (e.g., stearic acid, magnesium stearate), calcium sulfate, vegetable oil (e.g., soybean oil, sesame oil, peanut oil, olive oil, etc), polyols (e.g., propylene glycol, glycerol, mannitol, sorbitol, etc), emulsifier (eg., Tween®), wetting agent (e.g., sodium lauryl sulfate), colorant, flavouring agent, stabilizer, antioxidant, preservative, pyrogen-free water and so on.

The compound of the present invention, when applying, can be orally, rectally, parenterally (intravenously, intramuscularly or subcutaneously), topically administrated.

Solid dosage forms for oral administration include capsule, tablet, pill, powder and granule. Among which, active compounds are mixed with at least one common inert excipient (or carrier) such as sodium citrate or dicalcium phosphate, or mixed with the following ingredients: (a) filler or bulking agent, e.g., starch, lactose, sucrose, glucose, mannitol and silicic acid; (b) binder, e.g., carboxymethylcellulose, alginate, gelatin, polyvinyl pyrrolidone, sucrose and arabic gum; (c) humectants, e.g., glycerol; (d) disintegrating agent, e.g., agar, calcium carbonate, potato starch or tapioca starch, alginic acid, certain complex silicate, and sodium carbonate; (e) slowly dissolving agent, e.g., paraffin; (f) absorption accelerator, e.g., quaternary amine compound; (g) wetting agent, e.g., cetanol and glycerol monostearate; (h) adsorbent, e.g., kaolin; and (i) lubricant, e.g., talc, calcium stearate, magnesium stearate, solid polyethylene glycol, sodium lauryl sulfate, or mixture thereof. In capsule, tablet and pill, dosage form can also contain buffer.

Solid dosage forms such as tablet, sugar pill, capsule, pill and granule can be made by coat and shell materials, e.g., enteric coating and other materials well known in the art. They can comprise opacifying agent and the active compound in this composition or the release of compound can be released within a part of digestive tract in a delayed manner. Examples of the embedded components which can be used are polymeric substances and waxy substances. Active compound, when necessary, can form microcapsule with one or more of the above-mentioned excipients.

Liquid dosage forms for oral administration include pharmaceutically acceptable emulsion, solution, suspension, syrup or tincture. In addition to active compound, liquid dosage forms can include commonly employed inert diluents in the art, such as water or other solvent, solubilizer and emulsifier, e.g., ethanol, isopropanol, ethyl carbonate, ethyl acetate, propylene glycol, 1,3-butanediol, dimethylformamide as well as oil, particularly cottonseed oil, peanut oil, maize embryo oil, olive oil, castor oil and sesame oil or the mixture of these substances, etc.

In addition to these inert diluents, compositions can also comprise auxiliaries, such as wetting agent, emulsifier and suspending agent, sweetener, flavouring agent and flavour.

In addition to active compound, suspension can also comprise suspending agent, such as ethoxylated isooctadecanol, polyoxyethylene sorbitan and sorbitan ester, microcrystalline cellulose, aluminium methoxide and agar or the mixture of these substances, etc.

Compositions for parenteral administration can include physiologically acceptable sterile aqueous or nonaqueous solution, dispersion, suspension or emulsion, and sterile powders used to be redissolved into sterile injectable solution or dispersion. Suitable aqueous and nonaqueous carrier, diluents, solvent or excipient include water, ethanol, polyols and suitable mixture thereof.

The dosage forms of the compound of the present invention for topical administration include ointment, powder, patch, spray and inhalant. Active ingredients mix together with physiologically acceptable carrier and any preservative, buffer under sterile condition, or with possibly required propellant when necessary.

The compound of the present invention can be administrated alone or combined with other pharmaceutically acceptable compounds.

A safe and effective amount of the compounds of the present invention are applied to mammal (such as human) which need to be treated when using pharmaceutical composition, wherein dose is the pharmaceutically effective administration dose when applying, for a people of 60 kg body weight, daily administration dose is 1~1000 mg, preferably 10~500 mg. Of course, particular dose should consider factors such as administration route, patient health, which are within the technical scope of skilled physicians.

The major advantages of the invention include:
1. The compound of the present invention has higher DPP-IV-inhibiting activity and in vivo glucose-decreasing activity.
2. The compound of the present invention is a new type of DPP-IV inhibitor.
3. The preparation methods of the compounds of the prevent invention are simple with low manufacturing cost.

The invention will be more specifically explained in the following examples. It should be understood that these examples are used to illustrate the invention, not to limit the scope of the invention in any way. The experimental methods which the particular condition are not illustrated in the following examples are generally performed according to common conditions, or according to the conditions recommended by manufacturer. Unless otherwise stated, parts and percent are parts by weight and percent by weight.

In the all examples, melting point is determined by MEL-TEMP Melting Point Apparatus and thermometer is uncorrected; $^1$H NMR is recorded by Varian Mercury 400 Nuclear Magnetic Resonance Spectrometer, chemical shift is expressed by δ (ppm); Silica gels for isolation are all of 200-300 mesh if not specified, ratios of column chromatography to TLC detection developing agent are volume ratios.

Example 1

Step 1: Preparation of (3aR,6aR)-1-[(1R)-1-phenethyl]-5-(trifluoroacetyl)octahydropyrrolo[3,4-b]pyrrole 1b

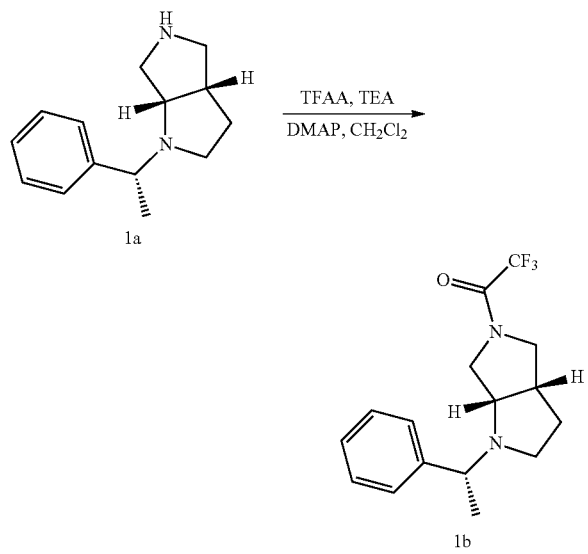

In ice bath, (3aS,6aS)-octahydro-1-[(R)-1-phenethyl]pyrrolo[3,4-b]pyrrole 1a (390 mg, 1.80 mmol) was dissolved in dichloromethane (10 mL), added N,N-dimethylaminopyridine (DMAP) (40 mg, 0.18 mmol) and triethylamine (TEA) (0.39 mL, 2.7 mmol), again added dropwise trifluoroacetic anhydride (TFAA) (0.38 mL, 2.7 mmol), stirred at room temperature overnight, added water, extracted aqueous phase by dichloromethane, dried by anhydrous magnesium sulfate, filtered and spun dry, purified by column chromatography (dichloromethane:methanol=50:1) to give title compound 1b as yellow oily matter (250 mg, 45%). $^1$H NMR (CDCl$_3$, 400 MHz): 1.40 (t, 3H), 1.60 (m, 1H), 2.07 (m, 1H), 2.53 (m, 1H), 2.76-2.84 (m, 2H), 2.99 (m, 1H), 3.09 (m, 1H), 3.39 (m, 1H), 3.62 (m, 3H), 7.27 (m, 5H).

Step 2: Preparation of 2,2,2-trifluoro-1-((3aR,6aR)-hexahydropyrrolo[3,4-b]pyrrol-5(1H)-yl)ethanone 1c

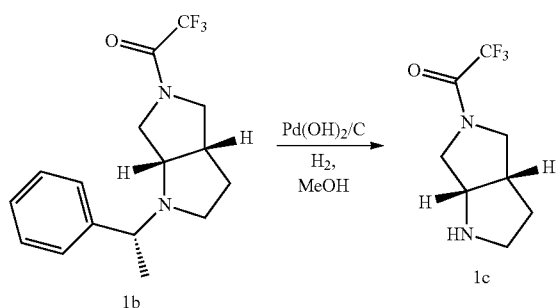

(3aR,6aR)-1-[(1R)-1-phenethyl]-5-(trifluoroacetyl)octahydropyrrolo[3,4-b]pyrrole 1b (250 mg, 0.80 mmol) was dissolved in methanol (10 mL), added Pd(OH)$_2$ (100 mg), catalyzed hydrogenation overnight at room temperature, filtered, concentrated to dry, added dichloromethane, again concentrated to dry, to give title compound 1c as colorless oily matter (272 mg, 100%). $^1$H NMR (CDCl$_3$, 400 MHz): 1.46 (s, 9H), 1.80 (m, 1H), 2.07 (m, 1H), 2.53 (m, 1H), 2.76-2.84 (m, 2H), 2.99 (m, 1H), 3.09 (m, 1.5H), 3.39 (m, 1.5H), 3.62 (m, 1H). MS m/z (ESI): 209.1 (M+1).

Step 3: Preparation of tertbutyl(R)-4-((3aS,6aS)-5-(2,2,2-trifluoroacetyl)hexahydropyrrolo[3,4-b]pyrrol-1(2H)-yl)-1-(2,4,5-trifluorophenyl)-4-oxybutan-2-ylcarbamate 1e

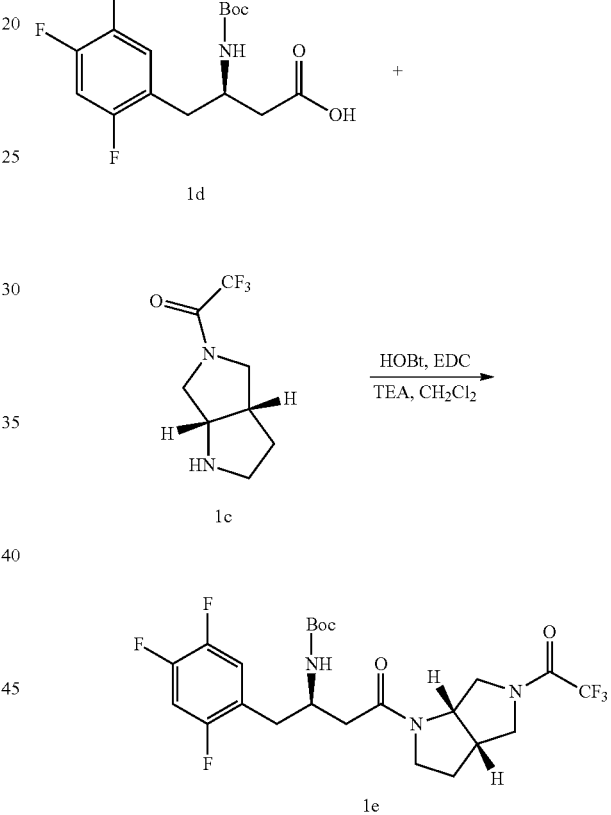

(R)-3-(tertbutoxycarbonylamino)-4-(2,4,5-trifluorophenyl)butyric acid 1d (435 mg, 1.30 mmol) and 2,2,2-trifluoro-1-((3aR,6aR)-hexahydropyrrolo[3,4-b]pyrrol-5(1H)-yl)ethanone 1c (272 mg, 1.30 mmol) were dissolved in dichloromethane (10 mL), added sequentially 1-hydroxylbenzotriazole (HOBt) (202 mg, 1.50 mmol), 1-(3-dimethylaminopropyl)-3-ethylcarbodiimide hydrochloride (EDC) (288 mg, 1.50 mmol) and triethylamine (151 mg, 1.50 mmol), stirred for 4 hours at room temperature. Organic phase was washed by 1N diluted hydrochloric acid (10 mL) and saturated sodium bicarbonate (10 mL) in order, dried by anhydrous sodium sulfate, concentrated, residues were purified by column chromatography to give title compound 1e (578 mg, 85%) as white solid. MS m/z (ESI): 524.2 (M+1).

Step 4: Preparation of tertbutyl(R)-1-(2,4,5-trifluorophenyl)-4-((3aS,6aS)-hexahydropyrrolo[3,4-b]pyrrol-1(2H)-yl)-4-oxybutan-2-ylcarbamate 1f

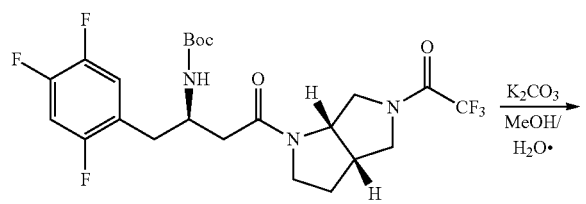

Tertbutyl(R)-4-((3aS,6aS)-5-(2,2,2-trifluoroacetyl)hexapyrrolo[3,4-b]pyrrol-1(2H)-yl)-1-(2,4,5-trifluorophenyl)-4-oxybutan-2-ylcarbamate 1e (578 mg, 1.1 mmol) was dissolved in methanol/water (5:1, 12 mL). Added potassium carbonate (167 mg, 1.2 mmol), stirred for 2 h at room temperature, concentrated to dry, added water, extracted by ethyl acetate, dried by anhydrous sodium sulfate, filtered, concentrated to dry to give title compound 1f as white solid (470 mg, 100%). MS m/z (ESI): 428.2 (M+1).

Step 5: Preparation of tertbutyl(R)-1-(2,4,5-trifluorophenyl)-4-((3aS,6aS)-hexahydro-5-methylpyrrolo[3,4-b]pyrrol-1(2H)-yl)-4-oxybutan-2-ylcarbamate 1g

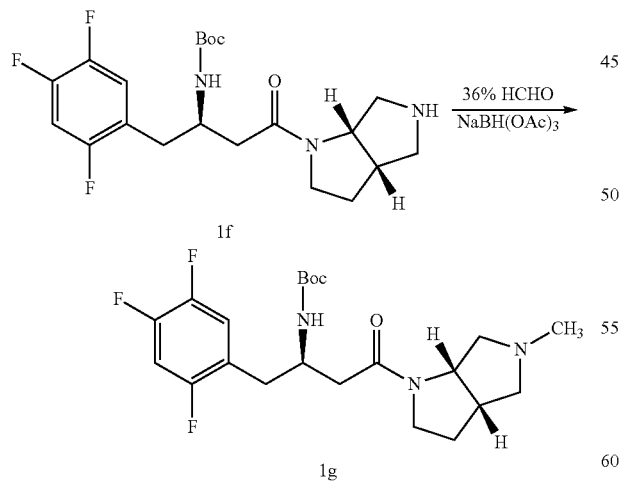

Tertbutyl(R)-1-(2,4,5-trifluorophenyl)-4-((3aS,6aS)-hexapyrrolo[3,4-b]pyrrol-1(2H)-yl)-4-oxybutan-2-ylcarbamate 1f (200 mg, 0.46 mmol) was dissolved in 36% formaldehyde solution (10 mL), added triacetoxy sodium borohydride (100 mg, 0.46 mmol), stirred for 20 hour at room temperature. Saturated sodium carbonate aqueous solution (25 mL) was added in solution to quench, aqueous phase was extracted by dichloromethane (20 mL×3), dried by anhydrous sodium sulfate, concentrated, residues were purified by column chromatography to give title compound 1g (145 mg, 72%) as colorless oily matter. MS m/z (ESI): 441.2 (M+1).

Step 6: Preparation of (R)-3-amino-1-((3aS,6aS)-hexahydro-5-methylpyrrolo[3,4-b]pyrrol-1(2H)-yl)-4-(2,4,5-trifluorophenyl)butan-1-one fumarate compound 1

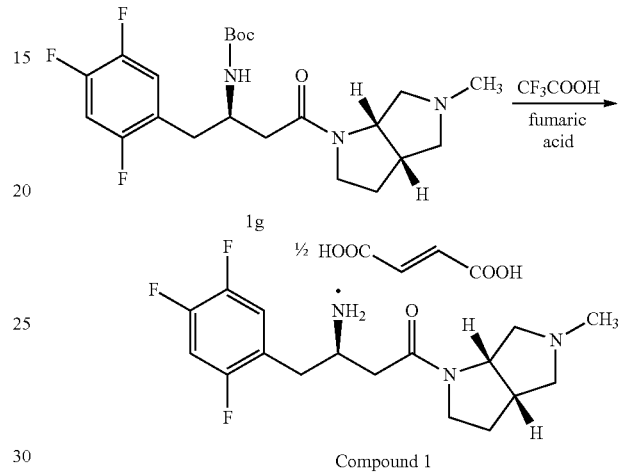

Tertbutyl(R)-1-(2,4,5-trifluorophenyl)-4-((3aS,6aS)-hexahydro-5-methylpyrrolo[3,4-b]pyrrol-1(2H)-yl)-4-oxybutan-2-ylcarbamate 1g (145 mg, 0.33 mmol) was dissolved in dichloromethane (1 mL), added dropwise trifluoroacetic acid (TFA) (1 mL), stirred for 1 hour at room temperature, concentrated after TLC detecting reaction was over, added dichloromethane (15 mL), washed by saturated sodium carbonate aqueous solution (15 mL), organic phase was dried by anhydrous sodium sulfate, concentrated, residues was dissolved in ethanol, added fumaric acid (20 mg, 0.17 mmol), stirred for 30 minutes at room temperature, precipitated solid, sucking filtrated to give title compound 1 (360 mg, 91%) as white solid. MS m/z (ESI): 342.2 (M+1). $^1$H NMR (D$_2$O, 400 MHz): δ 1.78 (m, 1H), 2.00 (m, 1H), 2.65-2.77 (m, 5H), 2.86-2.99 (m, 2H), 3.41-3.48 (m, 5H), 3.83 (m, 3H), 4.24-4.33 (m, 1H), 7.00-7.05 (m, 2H).

Example 2

Step 1: Preparation of tertbutyl(R)-1-(2,4,5-trifluorophenyl)-4-((3aS,6aS)-hexahydro-5-methoxyformylpyrrolo[3,4-b]pyrrol-1(2H)-yl)-4-oxybutan-2-ylcarbamate 2a

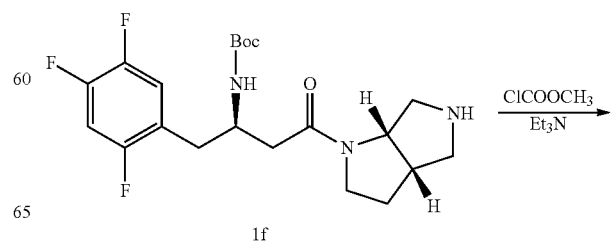

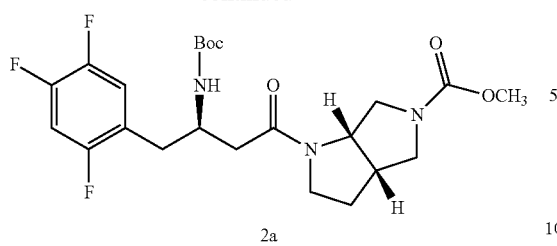

2a

Tertbutyl(R)-1-(2,4,5-trifluorophenyl)-4-((3aS,6aS)-hexapyrrolo[3,4-b]pyrrol-1(2H)-yl)-4-oxybutan-2-ylcarbamate 1f (250 mg, 0.58 mmol) was dissolved in dichloromethane (20 mL), added sequentially triethylamine (59 mg, 0.58 mmol) and methylchloroformate (55 mg, 0.58 mmol), stirred overnight at room temperature. Water (10 mL) was added in reaction solution, separated organic phase, aqueous phase was extracted by dichloromethane (20 mL), dried by anhydrous sodium sulfate, concentrated, residues was purified by column chromatography to give title compound 2a (278 mg, 99%) as colorless oily matter. MS m/z (ESI): 486.2 (M+1).

Step 2: Preparation of (R)-3-amino-1-((3aS,6aS)-5-methoxycarbonyl hexahydropyrrolo[3,4-b]pyrrol-1 (2H)-yl)-4-(2,4,5-trifluorophenyl)butan-1-one fumarate compound 2

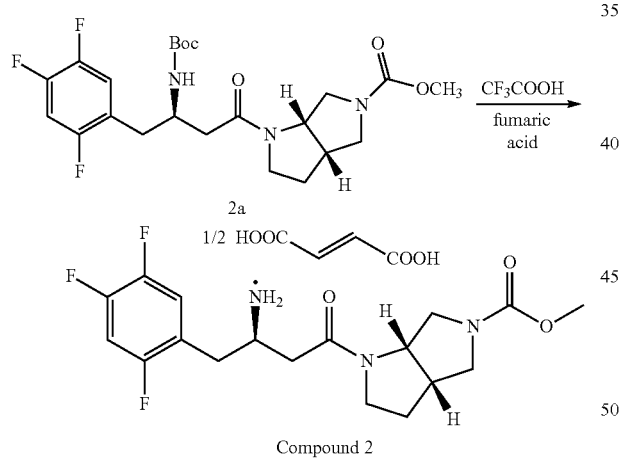

Compound 2

According to manipulation similar to step 6 of example 1, tertbutyl(R)-1-(2,4,5-trifluorophenyl)-4-((3aS,6aS)-hexahydro-5-methoxycarbonylpyrrolo[3,4-b]pyrrol-1(2H)-yl)-4-oxybutan-2-ylcarbamate 2a (278 mg, 0.57 mmol) was dissolved in dichloromethane (1 mL), added dropwise trifluoroacetic acid (TFA) (1 mL), added fumaric acid (33 mg, 0.29 mmol) after reaction was finished to give title compound 2 (180 mg, 82%) as white solid. MS m/z (ESI): 386.2 (M+1). $^1$H NMR (D$_2$O, 400 MHz): δ 1.86 (m, 1H), 2.22 (m, 1H), 2.76-3.24 (m, 6H), 3.45-3.63 (m, 4H), 3.75 (s, 3H), 3.80-4.25 (m, 4H), 4.50 (m, 1H), 6.63 (s, 1H), 6.78 (m, 1H), 7.23 (m, 1H).

Example 3

Step 1: Preparation of tertbutyl(R)-1-(2,4,5-trifluorophenyl)-4-((3aS,6aS)— hexahydro-5-(N,N-dimethylaminoformyl)-pyrrolo[3,4-b]pyrrol-1(2H)-yl)-4-oxybutan-2-ylcarbamate 3a

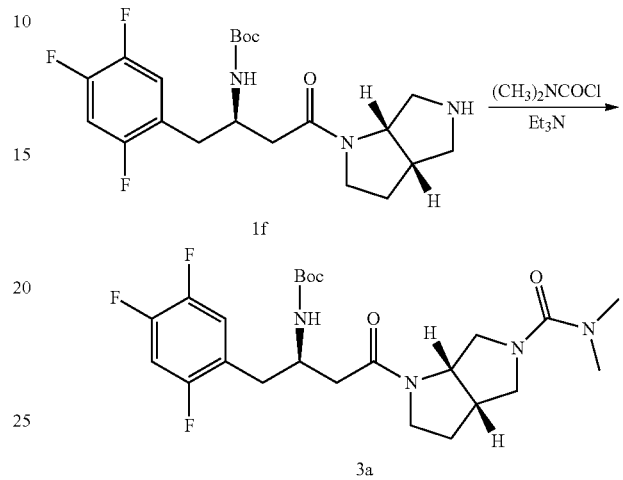

Tertbutyl(R)-1-(2,4,5-trifluorophenyl)-4-((3aS,6aS)-hexahydropyrrolo[3,4-b]pyrrol-1(2H)-yl)-4-oxybutan-2-ylcarbamate 1f (210 mg, 0.49 mmol) was dissolved in dichloromethane (20 mL), added sequentially dimethylaminoformyl chloride (52 mg, 0.49 mmol) and triethylamine (49 mg, 0.49 mmol), stirred overnight at room temperature. Water (10 mL) was added into reaction solution, seperated organic phase, aqueous phase was extracted by dichloromethane (20 mL), dried by anhydrous sodium sulfate, concentrated, residues was purified by column chromatography to give title compound 3a (151 mg, 62%) as colorless oily matter. MS m/z (ESI): 499.2 (M+1).

Step 3: Preparation of (R)-3-amino-1-((3aS,6aS)-5-(N,N-dimethyl aminoaminoformyl)-hexahydropyrrolo[3,4-b]pyrrol-1(2H)-yl)-4-(2,4,5-trifluorophenyl)butan-1-one fumarate compound 3

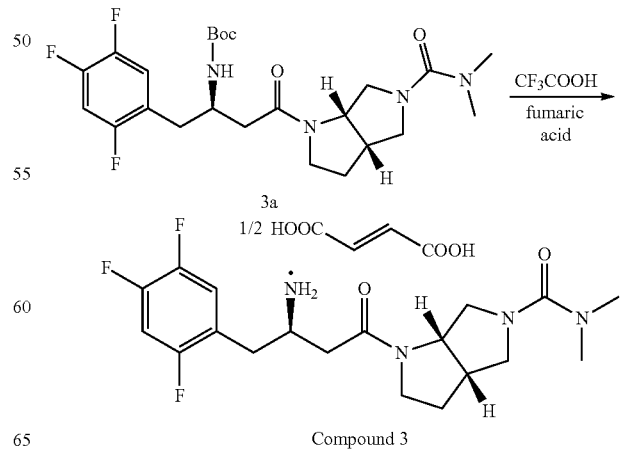

Compound 3

According to manipulation similar to step 6 of example 1, tertbutyl(R)-1-(2,4,5-trifluorophenyl)-4-((3aS,6aS)-hexahydro-5-(N,N-dimethylaminoformyl)-pyrrolo[3,4-b]pyrrol-1(2H)-yl)-4-oxybutan-2-ylcarbamate 3a (151 mg, 0.30 mmol) was dissolved in dichloromethane (1 mL), added dropwise trifluoroacetic acid (TFA) (1 mL), after reaction was finished, added fumaric acid (17 mg, 0.15 mmol) to give title compound 3 (77 mg, 56%) as white solid. MS m/z (ESI): 399.2 (M+1). $^1$H NMR (D$_2$O, 400 MHz): δ 1.95 (m, 1H), 2.19 (m, 1H), 2.64-3.18 (m, 12H) 3.38-3.62 (m, 4H), 3.68-4.15 (m, 4H), 4.45 (m, 1H), 6.61 (s, 1H), 6.78 (m, 1H), 7.23 (m, 1H).

Example 4

Step 1: Preparation of tertbutyl(R)-1-(2,4,5-trifluorophenyl)-4-((3aS,6aS)-hexahydro-5-(chloroformyl)-pyrrolo[3,4-b]pyrrol-1(2H)-yl)-4-oxybutan-2-ylcarbamate 4a

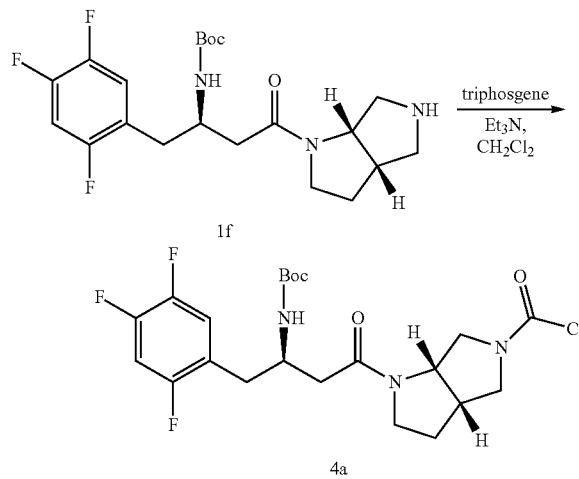

Tertbutyl(R)-1-(2,4,5-trifluorophenyl)-4-((3aS,6aS)-hexapyrrolo[3,4-b]pyrrol-1(2H)-yl)-4-oxybutan-2-ylcarbamate 1f (400 mg, 0.93 mmol) was dissolved in dichloromethane (20 mL), added solid triphosegene (92 mg, 0.31 mmol), added dropwise triethylamine (94 mg, 0.93 mmol) at −10° C., stirred for 3 hours at room temperature, water (10 mL) was added into reaction solution, seperated organic phase, aqueous phase was extracted by dichloromethane (20 mL), dried by anhydrous sodium sulfate, concentrated to give title compound 4a (432 mg, 95%) as colorless oily matter. Directly put into the next reaction step without purification.

Step 2: Preparation of tertbutyl(R)-1-(2,4,5-trifluorophenyl)-4-((3aS,6aS)-hexahydro-5-(methylaminoformyl)-pyrrolo[3,4-b]pyrrol-1(2H)-yl)-4-oxybutan-2-ylcarbamate 4b

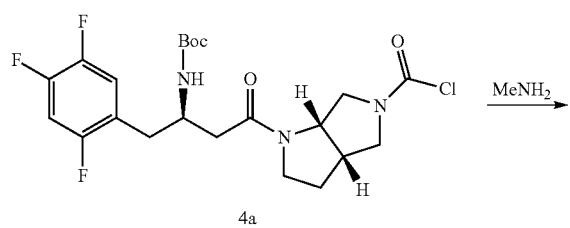

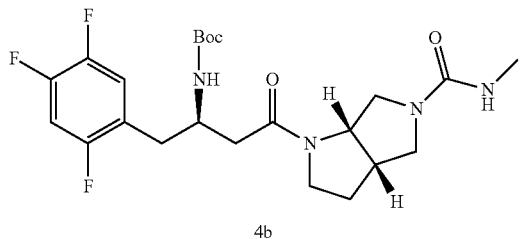

Tertbutyl(R)-1-(2,4,5-trifluorophenyl)-4-((3aS,6aS)-hexahydro-5-(chloroformyl)-pyrrolo[3,4-b]pyrrol-1(2H)-yl)-4-oxybutan-2-ylcarbamate 4a (432 mg, 0.88 mmol) was dissolved in ethanol (5 mL), added 33% of methylamine/ethanol solution (5 mL), stirred for 2 hours at room temperature, removed solvents under reduced pressure, residues were purified by column chromatography to give title compound 4b (225 mg, 53%) as colorless oily matter. MS m/z (ESI): 485.2 (M+1).

Step 3: Preparation of (R)-3-amino-1-((3aS,6aS)-5-(N-methylaminoformyl)-hexahydropyrrolo[3,4-b]pyrrol-1(2H)-yl)-4-(2,4,5-trifluorophenyl)butan-1-one fumarate compound 4

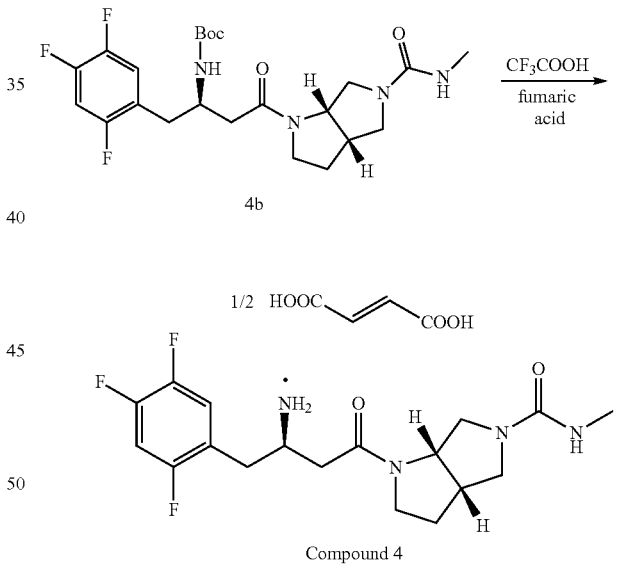

According to manipulation similar to step 6 of example 1, tertbutyl(R)-1-(2,4,5-trifluorophenyl)-4-((3aS,6aS)-hexahydro-5-(methylaminoformyl)-pyrrolo[3,4-b]pyrrol-1(2H)-yl)-4-oxybutan-2-ylcarbamate 4b (225 mg, 0.46 mmol) was dissolved in dichloromethane (1 mL), added dropwise trifluoroacetic acid (TFA) (1 mL), after reaction was finished, added fumaric acid (27 mg, 0.23 mmol) to give title compound 4 (95 mg, 47%) as white solid. MS m/z (ESI): 385.2 (M+1). $^1$H NMR (D$_2$O, 400 MHz): δ 1.93 (m, 1H), 2.17 (m, 1H), 2.63-3.15 (m, 9H), 3.36-3.60 (m, 4H), 3.66-4.14 (m, 4H), 4.45 (m, 1H), 6.60 (s, 1H), 6.78 (m, 1H), 7.23 (m, 1H).

Example 5

Step 1: Preparation of tertbutyl(R)-1-(2,4,5-trifluorophenyl)-4-((3aS,6aS)-hexahydro-5-(aminoformyl)-pyrrolo[3,4-b]pyrrol-1(2H)-yl)-4-oxybutan-2-ylcarbamate 5a

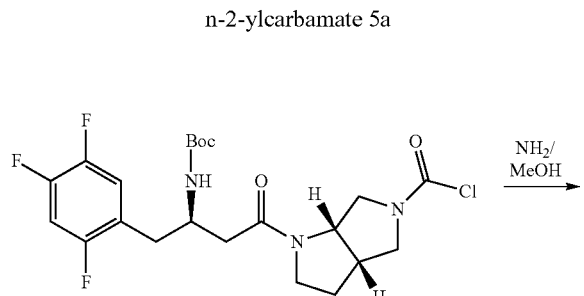

4a

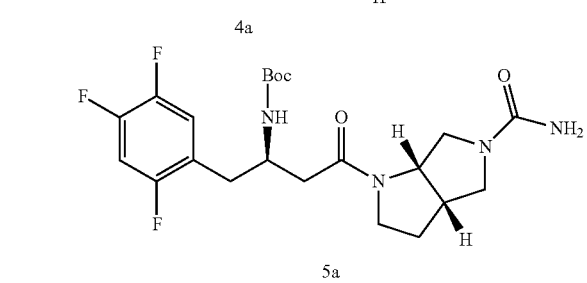

5a

Tertbutyl(R)-1-(2,4,5-trifluorophenyl)-4-((3aS,6aS)-hexahydro-5-(chloroformyl)-pyrrolo[3,4-b]pyrrol-1(2H)-yl)-4-oxybutan-2-ylcarbamate 4a (489 mg, 1.00 mmol) was dissolved in ammonia methanol solution (10 mL), stirred overnight at room temperature, removed solvents under reduced pressure, residues was purified by column chromatography to give title compound 5a (329 mg, 70%) as colorless oily matter. MS m/z (ESI): 471.1 (M+1).

Step 2: Preparation of (R)-3-amino-1-((3aS,6aS)-5-(aminoformyl)hexahydropyrrolo[3,4-b]pyrrol-1(2H)-yl)-4-(2,4,5-trifluorophenyl)butan-1-one fumarate compound 5

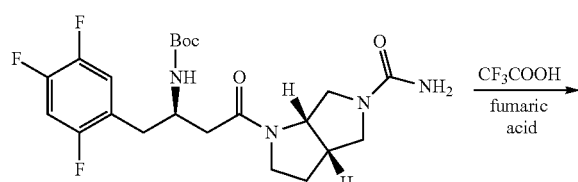

5a

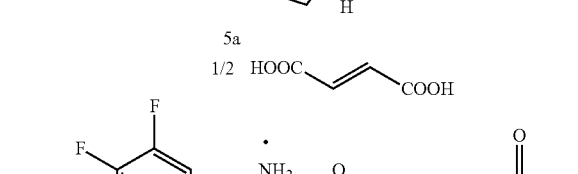

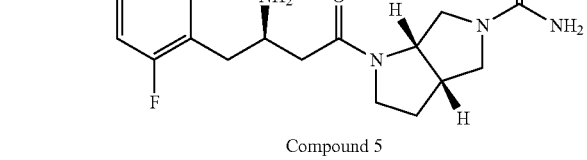

Compound 5

According to manipulation similar to step 6 of example 1, tertbutyl(R)-1-(2,4,5-trifluorophenyl)-4-((3aS,6aS)-hexahydro-5-(aminoformyl)-pyrrolo[3,4-b]pyrrol-1(2H)-yl)-4-oxybutan-2-ylcarbamate 5a (329 mg, 0.70 mmol) was dissolved in dichloromethane (1 mL), added dropwise trifluoroacetic acid (TFA) (1 mL), after reaction was finished, added fumaric acid (41 mg, 0.35 mmol) to give title compound 5 (78 mg, 26%) as white solid. MS m/z (ESI): 371.2 (M+1). $^1$H NMR (D$_2$O, 400 MHz): δ 1.92 (m, 1H), 2.15 (m, 1H), 2.63-3.11 (m, 6H), 3.36-3.55 (m, 4H), 3.61-4.12 (m, 4H), 4.42 (m, 1H), 6.58 (s, 1H), 6.78 (m, 1H), 7.23 (m, 1H).

Example 6

Step 1: Preparation of cyclopropyl((3aR,6aR)-hexahydro-1-[(R)-1-phenethyl]pyrrolo[3,4-b]pyrrol-5(1H)-yl)methylketone 6b

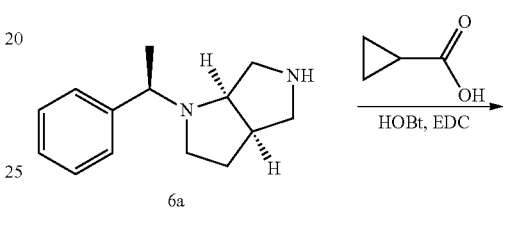

6a

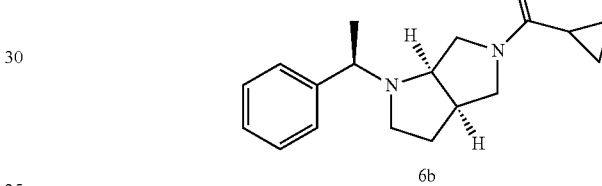

6b (3aR,6aR)-octahydro-1-[(R)-1-phenethyl]pyrrolo[3,4-b] pyrrole 6a (prepared according to patent US20050101602) (340 mg, 1.57 mmol) and cyclopropylformic acid (135 mg, 1.57 mmol) were dissolved in dichloromethane (20 mL), added sequentially HOBt (255 mg, 1.89 mmol), EDC (362 mg, 1.89 mmol) and triethylamine (191 mg, 1.89 mmol), stirred overnight at room temperature. Water (10 mL) was added into reaction solution, seperated organic phase, aqueous phase was extracted by dichloromethane (20 mL), dried by anhydrous sodium sulfate, concentrated, residues was purified by column chromatography to give cyclopropyl(3aR,6aR)-hexahydro-1-[(R)-1-phenethyl]pyrrolo[3,b]pyrroloe-5 (1H)-methylketone 6b (330 mg, 75%) as colorless oily matter. MS m/z (ESI): 285.2 (M+1).

Step 2: Preparation of cyclopropyl((3aR,6aR)-hexahydropyrrolo[3,4-b]pyrrol-5(1H)-yl)methylketone 6c

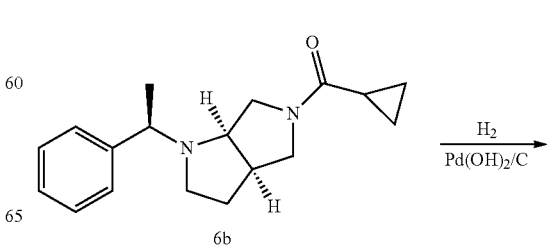

6b

41

-continued

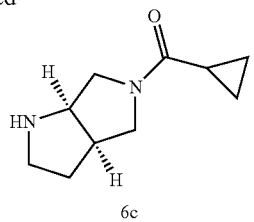
6c

Cyclopropyl(3aR,6aR)-hexahydro-1-[(R)-1-phenethyl]pyrrolo[3,4-b]pyrrole-5(1H)-methylketone 6b (330 mg, 1.16 mmol) was dissolved in anhydrous methanol (10 mL), added palladium hydroxide/carbon (90 mg), catalyzed hydrogenation for 3 hours at room temperature, concentrated to give cyclopropyl((3aR,6aR)-hexahydropyrrolo[3,4-b]pyrrol-5(1H)-yl)methylketone 6c (200 mg, 96%) as colorless oily matter. MS m/z (ESI): 181.1 (M+1).

Step 3: Preparation of (R)-3-amino-1((3aR,6aR)-5-(cyclopropylcarbonyl)-hexahydropyrrolo[3,4-b]pyrrol-1(2H)-yl)-4-(2,4,5-trifluorophenyl)butan-1-one-fumarate compound 6

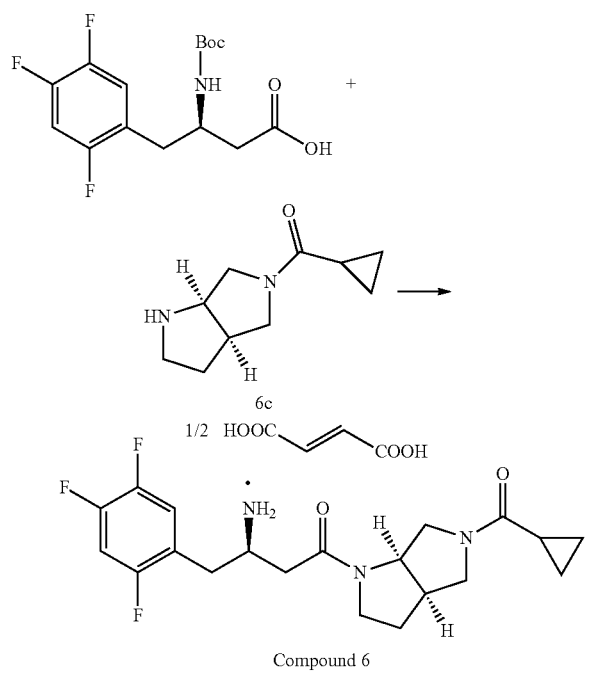
Compound 6

(R)-3-(tertbutoxycarbonylamino)-4-(2,4,5-trifluorophenyl)butyric acid (369 mg, 1.11 mmol) and cyclopropyl((3aR,6aR)-hexahydropyrrolo[3,4-b]pyrrol-5(1H)-yl)methylketone 6c (200 mg, 1.11 mmol) were dissolved in dichloromethane (10 mL), added sequentially 1-hydroxybenzotriazole(HOBt) (175 mg, 1.30 mmol), 1-(3-dimethylaminopropyl)-3-ethylcarbodiimide hydrochloride (EDC) (250 mg, 1.30 mmol) and triethylamine (151 mg, 1.50 mmol), stirred for 4 hours at room temperature. Organic phase was sequentially washed by 1N diluted hydrochloric acid (10 mL) and saturated sodium carbonate aqueous solution (10 mL), dried by anhydrous sodium sulfate, concentrated, residues was purified by column chromatography, resultant was dis-

42 solved in anhydrous ethanol (5 mL), added fumaric acid (64 mg, 0.55 mmol), stirred for 30 min, precipitated solid, filtered, dried to give title compound 6 (276 mg, 55%) as white solid. MS m/z (ESI): 396.2 (M+1). $^1$H NMR (CD$_3$OD, 600 MHz): δ 0.87-0.93 (m, 4H), 1.75-1.97 (m, 2H), 2.11-2.21 (m, 1H), 2.52-2.63 (m, 1H), 2.71-2.82 (m, 1H), 2.95-3.12 (m, 2H), 3.55-3.78 (m, 5H), 3.83 (m, 2H), 3.91-4.15 (m, 1H), 4.31-4.55 (m, 1H), 6.78 (m, 1H), 7.23 (m, 1H).

Example 7

Step 1: Preparation of tertbutyl(R)-1-(2,4,5-trifluorophenyl)-4-((3aS,6aS)-hexahydro-5-(2-fluoro-2-methylpropionyl)-pyrrolo[3,4-b]pyrrol-1(2H)-yl)-4-oxybutan-2-ylcarbamate 7a

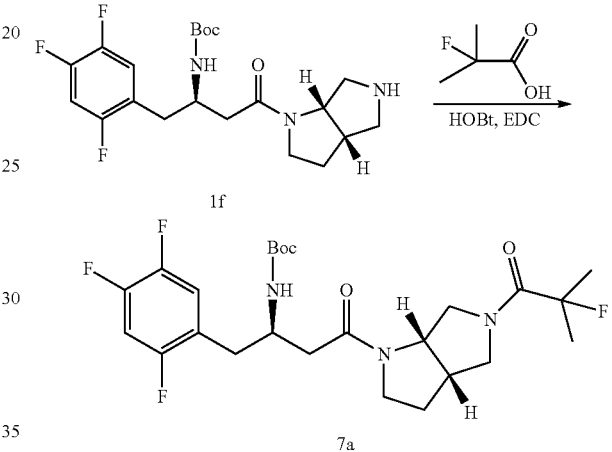
7a

Tertbutyl(R)-1-(2,4,5-trifluorophenyl)-4-((3aS,6aS)-hexahydropyrrolo[3,4-b]pyrrol-1(2H)-yl)-4-oxybutan-2-yl-carbamate 1f (250 mg, 0.58 mmol) and 2-fluoro-2-methylpropionic acid (purchased from J&K Scientific Ltd.) (61 mg, 0.58 mmol) were dissolved in dichloromethane (10 mL), added sequentially HOBt (88 mg, 0.65 mmol), EDC (125 mg, 0.65 mmol) and triethylamine (71 mg, 0.70 mmol), stirred overnight at room temperature. Water was added into reaction solution (10 mL), seperated organic phase, aqueous phase was extracted by dichloromethane (20 mL), dried by anhydrous sodium sulfate, concentrated, residues was purified by column chromatography to give title compound 7a (268 mg, 90%) as colorless oily matter. MS m/z (ESI): 516.2 (M+1).

Step 2: Preparation of (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butan-1-one compound 7

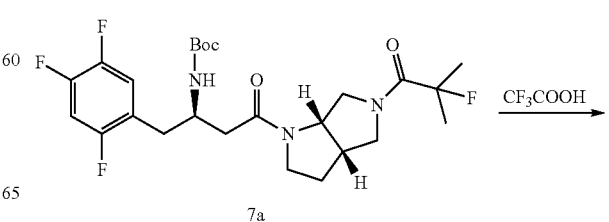
7a

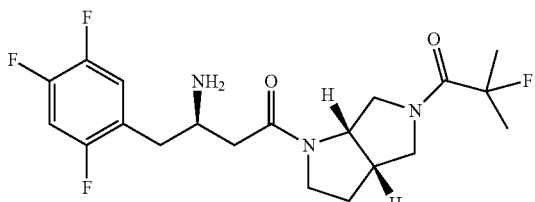

Compound 7

Tertbutyl(R)-1-(2,4,5-trifluorophenyl)-4-((3aS,6aS)-hexahydro-5-(2-fluoro-2-methylpropionyl)-pyrrolo[3,4-b]pyrrol-1(2H)-yl)-4-oxybutan-2-ylcarbamate 7a (268 mg, 0.52 mmol) was dissolved in dichloromethane (1 mL), added dropwise trifluoroacetic acid (TFA) (1 mL), stirred for 1 hour at room temperature, concentrated after TLC monitoring reaction was over, added dichloromethane (15 mL), washed by saturated sodium carbonate aqueous solution (15 mL), organic phase was dried by anhydrous sodium sulfate, concentrated, residues was purified by column chromatography to give title compound 7 (215 mg, 100%) as white solid. MS m/z (ESI): 416.4 (M+1), 438.2 (M+Na). $^1$H NMR (D$_2$O, 400 MHz): δ 1.62 (m, 6H), 1.96 (m, 1H), 2.20 (m, 1H), 2.78-2.91 (m, 2H), 3.05-3.30 (m, 3H), 3.42-3.83 (m, 6H), 3.96 (m, 2H), 7.20 (m, 1H), 7.35 (m, 1H).

Example 8

(R)-3-amino-1-((3aS,6aS)-5-(2-fluoro-2-methylpropionyl)-hexahydropyrrolo[3,4-b]-pyrrol-1 (2H)-yl)-4-(2,4,5-trifluorophenyl)butan-1-one fumarate

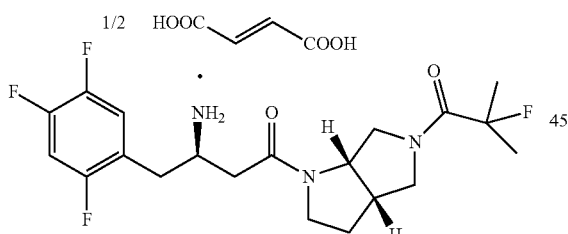

Free base (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butan-1-one compound 7 (100 mg, 0.24 mmol) obtained from example 7 was dissolved in ethanol, added fumaric acid (14 mg, 0.12 mmol), stirred for 30 minutes at room temperature, precipitated solid, sucking filtrated to give (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butan-1-onefumarate compound 8 (60 mg, 53%) as white solid. MS m/z (ESI): 416.4 (M+1), 438.2 (M+Na). $^1$H NMR (D$_2$O, 400 MHz): δ 1.62 (m, 6H), 1.96 (m, 1H), 2.20 (m, 1H), 2.78-2.91 (m, 2H), 3.05-3.30 (m, 3H), 3.42-3.83 (m, 6H), 3.96 (m, 2H), 6.68 (s, 1H), 7.20 (m, 1H), 7.35 (m, 1H).

Example 9

(R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butan-1-one hydrochloride

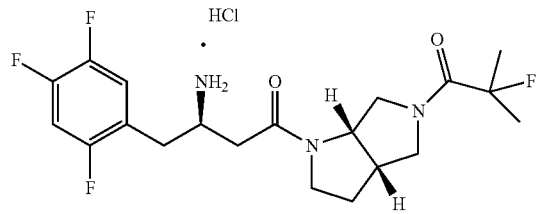 [SMILES: Cl ; CC(C)(F)C(=O)N1C[C@@H]2CCN(C(=O)C[C@H](N)Cc3cc(F)c(F)cc3F)[C@@H]2C1]

Free base (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butan-1-one compound 7 (100 mg, 0.24 mmol) obtained from example 7 was dissolved in ethanol (0.5 mL), added dropwise saturated hydrogen chloride diethyl ether solution (5 mL), precipitated white solid by stirring, standing for 4 hours in ice bath, filtered to give (R)-3-amino-1-((3aS, 6aS)-5-(2-fluoro-2-methylpropionyl)-hexahydropyrrolo[3,4-b]pyrrol-1(2H)-yl)-4-(2,4,5-trifluorophenyl)butan-1-one hydrochloride compound 9 (68 mg, 0.63%) as white powder. MS m/z (ESI): 416.4 (M+1), 438.2 (M+Na). $^1$H NMR (D$_2$O, 400 MHz): δ 1.62 (m, 6H), 1.96 (m, 1H), 2.20 (m, 1H), 2.78-2.91 (m, 2H), 3.05-3.30 (m, 3H), 3.42-3.83 (m, 6H), 3.96 (m, 2H), 7.20 (m, 1H), 7.35 (m, 1H).

Example 10

(R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butan-1-one phosphate

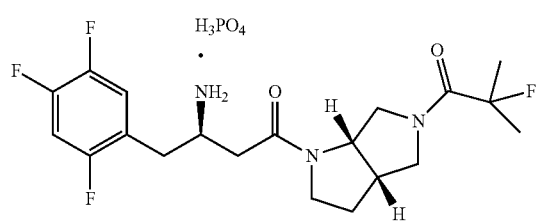 [SMILES: CC(C)(F)C(=O)N1C[C@@H]2CCN(C(=O)C[C@H](N)Cc3cc(F)c(F)cc3F)[C@@H]2C1 ; "H3PO4"]

Free base (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butan-1-one compound 7 (100 mg, 0.24 mmol) obtained from example 7 was dissolved in ethanol (0.5 mL), added dropwise into phosphoric acid (24 mg, 0.24 mmol) in ethanol solution (1 mL), stirred until precipitation of white solid, filtered to give (R)-3-amino-1-((3aS, 6aS)-5-(2-fluoro-2-methylpropionyl)-hexahydropyrrolo[3,4-b]pyrrol-1(2H)-yl)-4-(2,4,5-trifluorophenyl)butan-1-one phosphate compound 10 (84 mg, 84%) as white powder. MS m/z (ESI): 416.4 (M+1), 438.2 (M+Na). $^1$H NMR (D$_2$O, 400 MHz): δ 1.62 (m, 6H), 1.96 (m, 1H), 2.20 (m, 1H), 2.78-2.91 (m, 2H), 3.05-3.30 (m, 3H), 3.42-3.83 (m, 6H), 3.96 (m, 2H), 7.20 (m, 1H), 7.35 (m, 1H).

Example 11

(R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butan-1-onemethane sulfonate

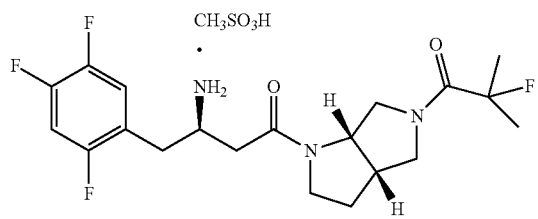 [SMILES: CC(C)(F)C(=O)N1C[C@@H]2CCN(C(=O)C[C@H](N)Cc3cc(F)c(F)cc3F)[C@@H]2C1 ; "CH3SO3H"]

Free base (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butan-1-one compound 7 (100 mg, 0.24 mmol) obtained from example 7 was dissolved in isopropanol (0.5 mL), added dropwise into mesilate (23 mg, 0.24 mmol) in isopropanol solution (1 mL), stirred until precipitation of white solid, filtered to give (R)-3-amino-1-((3aS, 6aS)-5-(4-cyanopyrrol-2-yl)hexahydropyrrolo[3,4-b]pyrrol-1(2H)-yl)-4-(2,4,5-trifluorophenyl)butan-1-one mesylate compound 11 (68 mg, 69%) as white powder. MS m/z (ESI): 416.4 (M+1), 438.2 (M+Na). $^1$H NMR (D$_2$O, 400 MHz): δ 1.62 (m, 6H), 1.96 (m, 1H), 2.20 (m, 1H), 2.78-2.91 (m, 2H), 3.05-3.30 (m, 3H), 3.42-3.83 (m, 6H), 3.96 (m, 2H), 7.20 (m, 1H), 7.35 (m, 1H).

Example 12

Step 1: Preparation of tertbutyl(R)-1-(2,4,5-trifluorophenyl)-4-((3aS,6aS)-hexahydro-5-(cyclopropylformyl)-pyrrolo[3,4-b]pyrrol-1(2H)-yl)-4-oxybutan-2-ylcarbamate 12a

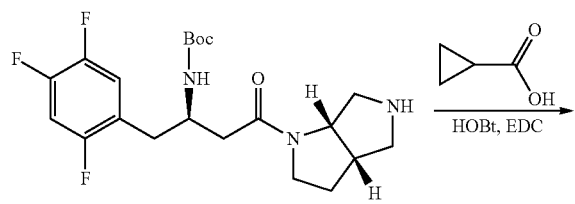

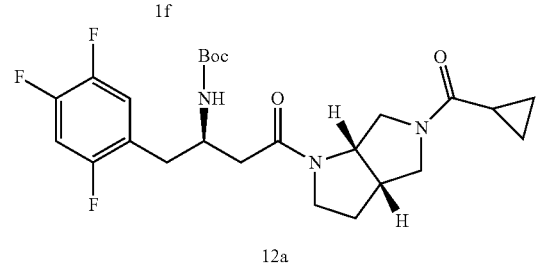

Tertbutyl(R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) and cyclopropylformic acid (40 mg, 0.46 mmol) were dissolved in dichloromethane (10 mL), added sequentially HOBt (88 mg, 0.65 mmol), EDC (125 mg, 0.65 mmol) and triethylamine (71 mg, 0.70 mmol), stirred overnight at room temperature. Water was added into reaction solution (10 mL), seperated organic phase, aqueous phase was extracted by dichloromethane (20 mL), dried by anhydrous sodium sulfate, concentrated, residues was purified by column chromatography to give title compound 7a (205 mg, 90%) as white solid. MS m/z (ESI): 496.2 (M+1).

Step 2: (R)-3-amino-1-((3aS,6aS)-5-(cyclopropylcarbonyl)-hexahydropyrrolo[3,4-b]pyrrol-1(2H)-yl)-4-(2,4,5-trifluorophenyl)butan-1-one fumarate compound 12

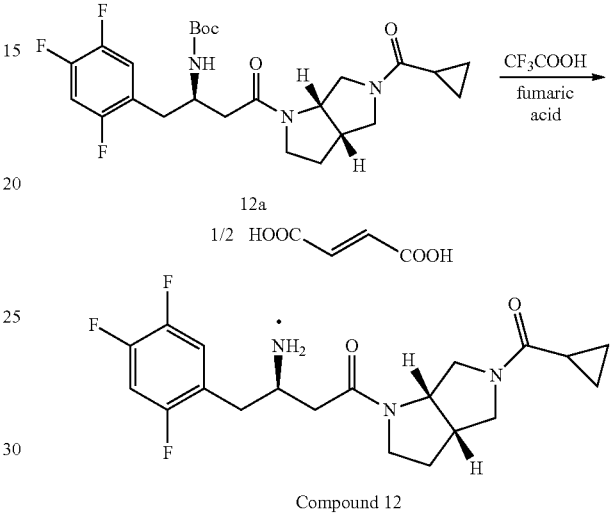

According to manipulation similar to step 6 of example 1, tertbutyl(R)-1-(2,4,5-trifluorophenyl)-4-((3aS,6aS)-hexahydro-5-(cyclopropylformyl)-pyrrolo[3,4-b]pyrrol-1(2H)-yl)-4-oxybutan-2-ylcarbamate 12a (205 mg, 0.41 mmol) was dissolved in dichloromethane (1 mL), added dropwise trifluoroacetic acid (TFA) (1 mL), after reaction was finished, added fumaric acid (23 mg, 0.20 mmol) to give title compound 12 (132 mg, 74%) as white solid. MS m/z (ESI): 396.2 (M+1). $^1$H NMR (CD$_3$OD, 600 MHz): δ 0.87-0.95 (m, 4H), 1.71-1.95 (m, 2H), 2.12-2.21 (m, 1H), 2.52-2.64 (m, 1H), 2.71-2.83 (m, 1H), 2.95-3.13 (m, 2H), 3.55-3.75 (m, 5H), 3.82 (m, 2H), 3.90-4.13 (m, 1H), 4.30-4.54 (m, 1H), 6.68 (s, 1H), 7.20 (m, 1H), 7.35 (m, 1H).

Example 13

(R)-3-amino-1-((3aS,6aS)-5-(1-fluorocyclopropylcarbonyl)-hexahydropyrrolo[3,4-b]pyrrol-1(2H)-yl)-4-(2,4,5-trifluorophenyl)butan-1-one fumarate compound 13

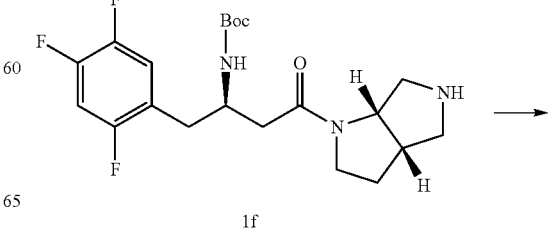

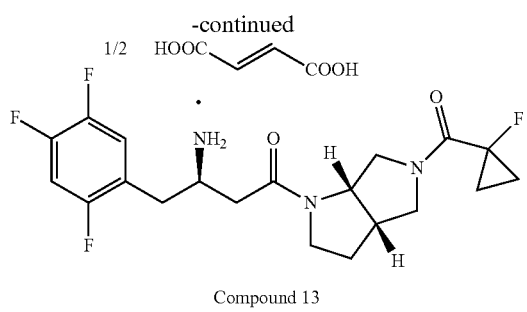

Compound 13

According to manipulation similar to example 12, tertbutyl (R)-1-(2,4,5-fluorophenyl)-4-((3aS,6aS)-hexahydropyrrole[3,4-b]pyrrol-1(2H)-yl)-4-oxybutan-2-ylcarbamate 1f (200 mg, 0.46 mmol) reacted with 1-fluorocyclopropylformic aid (48 mg, 0.46 mmol) (purchased from Alfa Aesar (Tianjin) Co. Ltd), intermediate was harvested after column chromatography, again added fumaric acid (28 mg, 0.24 mmol) to give target compound 13 (76 mg, 35%). MS m/z (ESI): 414.4 (M+1), 436.4 (M+Na). $^1$H NMR (CD$_3$OD, 600 MHz): δ 7.35 (m, 1H), 7.20 (m, 1H), 6.68 (s, 1H), 4.50 (m, 1H), 3.96 (m, 3H), 3.42-3.83 (m, 6H), 3.05-3.30 (m, 3H), 2.78-2.91 (m, 2H), 2.20 (m, 1H), 1.96 (m, 1H), 1.01 (m, 2H), 0.95 (m, 2H).

Example 14

Preparation of (R)-3-amino-1-((3aS,6aS)-5-(1-hydroxylcyclopropylcarbonyl)-hexahydropyrrolo[3,4-b]pyrrol-1(2H)-yl)-4-(2,4,5-trifluorophenyl)butan-1-one fumarate compound 14

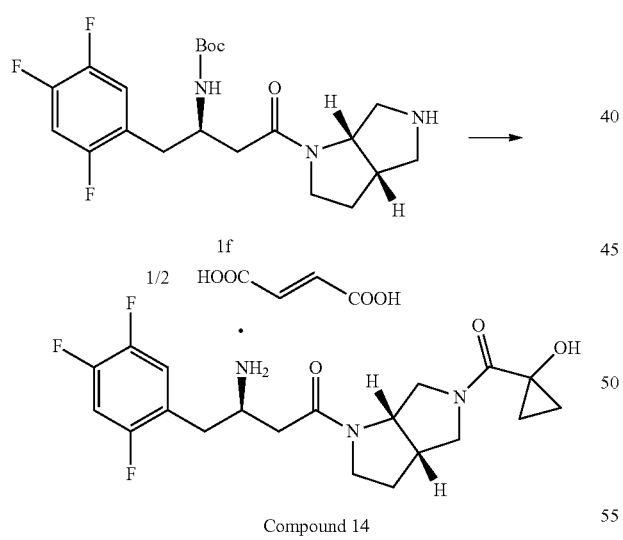

Compound 14

According to manipulation similar to example 12, tertbutyl (R)-1-(2,4,5-fluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with 1-hydroxylcyclopropylformic acid (47 mg, 0.46 mmol) (purchased from Alfa Aesar (Tianjin) Co. Ltd), intermediate was harvested after column chromatography, again added fumaric acid (28 mg, 0.24 mmol) to give target compound 14 (95 mg, 44%). MS m/z (ESI): 412.4 (M+1), 434.4 (M+Na). $^1$H NMR (CD$_3$OD, 600 MHz): δ 7.35 (m, 1H), 7.20 (m, 1H), 6.68 (s, 1H), 4.51 (m, 1H), 3.94 (m, 3H), 3.40-3.81 (m, 6H), 3.15-3.32 (m, 3H), 2.75-2.92 (m, 2H), 2.24 (m, 1H), 1.97 (m, 1H), 1.03 (m, 2H), 0.95 (m, 2H).

Example 15

Preparation of (R)-3-amino-1-((3aS,6aS)-5-(1-methylcyclopropylcarbonyl)-hexahydropyrrolo[3,4-b]pyrrol-1(2H)-yl)-4-(2,4,5-trifluorophenyl)butan-1-one fumarate compound 15

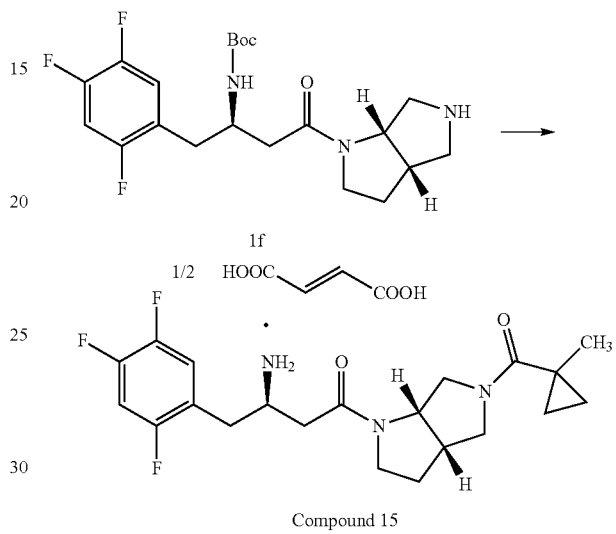

Compound 15

According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) (purchased from Sigma-Aldrich (Shanghai) Trading Co., Ltd) reacted with 1-methylcyclopropylformic acid (46 mg, 0.46 mmol), intermediate was harvested by column chromatography, again added fumaric acid (28 mg, 0.24 mmol) to give target compound 15 (111 mg, 51%). MS m/z (ESI): 410.4 (M+1), 432.4 (M+Na). $^1$H NMR (CD$_3$OD, 600 MHz): δ 7.34 (m, 1H), 7.21 (m, 1H), 6.68 (s, 1H), 4.51 (m, 1H), 3.94 (m, 3H), 3.41-3.80 (m, 6H), 3.11-3.30 (m, 3H), 2.71-2.90 (m, 2H), 2.22 (m, 1H), 1.95 (m, 1H), 1.29 (s, 3H), 1.01 (m, 2H), 0.91 (m, 2H).

Example 16

Preparation of (R)-3-amino-1-((3aS,6aS)-5-(cyclopropylmethylidenecarbonyl)-hexahydropyrrolo[3,4-b]pyrrol-1(2H)-yl)-4-(2,4,5-trifluorophenyl)butan-1-onefumarate compound 16

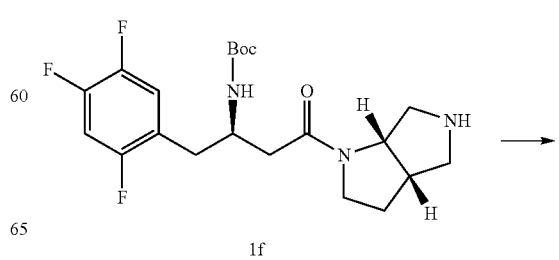

1f

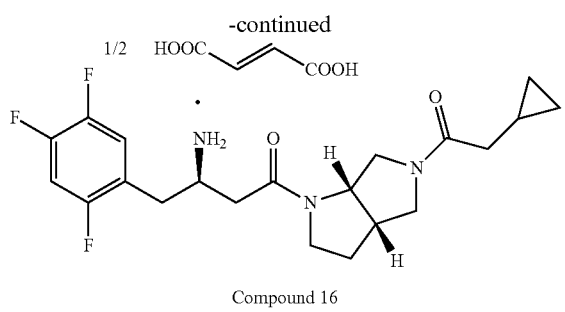

Compound 16

According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with 2-cyclopropylacetic acid (46 mg, 0.46 mmol), intermediate was harvested by column chromatography, again added fumaric acid (28 mg, 0.24 mmol) to give target compound 16 (50 mg, 23%). MS m/z (ESI): 410.4 (M+1), 432.4 (M+Na). $^1$H NMR (CD$_3$OD, 600 MHz): δ 7.33 (m, 1H), 7.20 (m, 1H), 6.68 (s, 1H), 4.50 (m, 1H), 3.93 (m, 3H), 3.41-3.76 (m, 6H), 3.11-3.26 (m, 3H), 2.70-2.88 (m, 2H), 2.22 (m, 1H), 2.14 (m, 2H), 1.95 (m, 1H), 1.11 (m, 1H), 0.95 (m, 2H), 0.83 (m, 2H).

Example 17

Preparation of (R)-3-amino-1-((3aS,6aS)-5-(1-cyanocyclopropylcarbonyl)-hexahydropyrrolo[3,4-b]pyrrol-1(2H)-yl)-4-(2,4,5-trifluorophenyl)butan-1-one fumarate compound 17

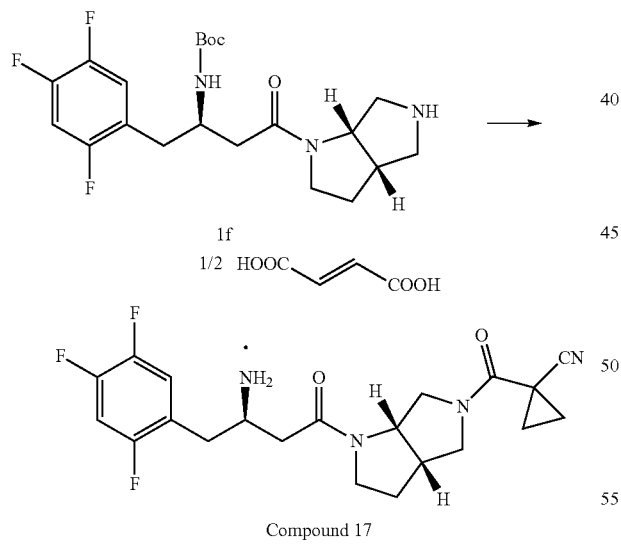

Compound 17

According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with 1-cyanocyclopropylformic acid (51 mg, 0.46 mmol), intermediate was harvested by column chromatography, again added fumaric acid (28 mg, 0.24 mmol) to give target compound 17 (85 mg, 3 g %). MS m/z (ESI): 421.4 (M+1). $^1$H NMR (CD$_3$OD, 600 MHz): δ 1.57 (m, 2H), 1.63-1.70 (m, 2H), 1.89 (m, 1H), 2.13 (m, 1H), 2.63-2.82 (m, 2H), 2.90-3.25 (m, 4H), 3.52-3.69 (m, 4H), 4.04 (m, 2H), 4.34 (m, 1H), 6.68 (s, 1H), 7.17 (m, 1H), 7.29 (m, 1H).

Example 18

Preparation of (R)-3-amino-1-((3aS,6aS)-5-(isopropylcarbonyl)-hexahydropyrrolo[3,4-b]pyrrol-1(2H)-yl)-4-(2,4,5-trifluorophenyl)butan-1-one fumarate compound 18

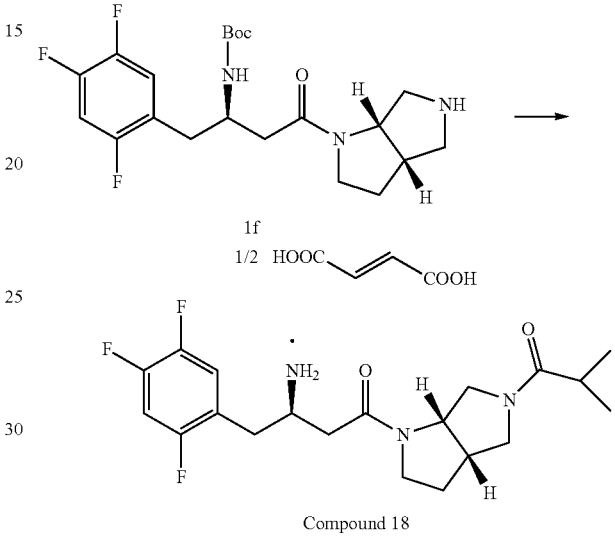

Compound 18

According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with isobutyric acid (41 mg, 0.46 mmol), intermediate was harvested by column chromatography, again added fumaric acid (28 mg, 0.24 mmol) to give target compound 18 (92 mg, 42%). MS m/z (ESI): 398.4 (M+1). $^1$H NMR (CD$_3$OD, 600 MHz): δ 1.08 (m, 6H), 1.90 (m, 1H), 2.16 (m, 1H), 2.88 (m, 1H), 3.14 (m, 3H), 3.44 (m, 1H), 3.68 (m, 5H), 3.88 (m, 2H), 4.01 (m, 1H), 4.50 (m, 1H), 6.68 (s, 1H), 7.23 (m, 1H), 7.34 (m, 1H).

Example 19

Preparation of (R)-3-amino-1-((3aS,6aS)-5-(3-methylbutyryl)-hexahydropyrrolo[3,4-b]pyrrol-1(2H)-yl)-4-(2,4,5-trifluorophenyl)butan-1-one fumarate compound 19

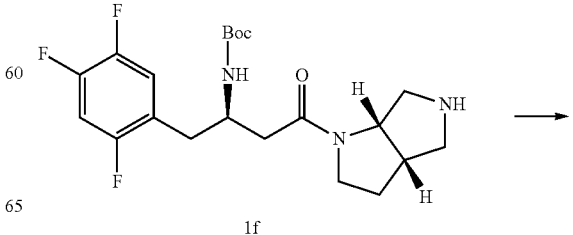

1f

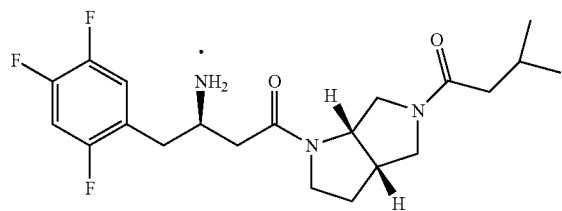

Compound 19

According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with 3-methylbutyric acid (51 mg, 0.46 mmol), intermediate was harvested by column chromatography, again added fumaric acid (28 mg, 0.24 mmol) to give target compound 19 (97 mg, 45%). MS m/z (ESI): 412.4 (M+1). $^1$H NMR (CD$_3$OD, 600 MHz): δ 0.88-0.99 (m, 6H), 1.82-1.91 (m, 1H), 1.94-2.22 (m, 4H), 2.60-2.70 (m, 2H), 2.93-3.09 (m, 4H), 3.31-3.45 (m, 2H), 3.47-3.69 (m, 3H), 3.70-3.83 (m, 2H), 4.44 (m, 1H), 6.68 (s, 1H), 7.18-7.40 (m, 2H).

Example 20

Preparation of (R)-3-amino-1-((3aS,6aS)-5-(tertvaleryl)-hexahydropyrrolo[3,4-b]pyrrol-1(2H)-yl)-4-(2,4,5-trifluorophenyl)butan-1-one fumarate compound 20

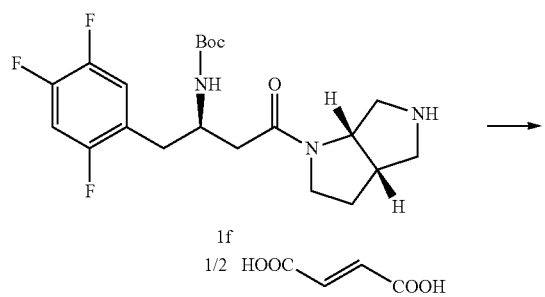

Compound 20

According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with tertbutyric acid (47 mg, 0.46 mmol), intermediate was harvested by column chromatography, again added fumaric acid (28 mg, 0.24 mmol) to give target compound 20 (82 mg, 38%). MS m/z (ESI): 412.4 (M+1). $^1$H NMR (CD$_3$OD, 600 MHz): δ 1.19 (s, 9H), 1.84 (m, 1H), 2.04-2.17 (m, 1H), 2.87 (m, 3H), 3.41 (m, 2H), 3.53 (m, 3H), 3.62 (m, 2H), 3.69 (m, 2H), 3.83-3.94 (m, 1H), 4.42 (m, 1H), 6.95 (m, 1H), 7.17 (m, 1H).

Example 21

Preparation of (R)-3-amino-1-((3aS,6aS)-(3,3-dimethylbutyryl)-hexahydropyrrolo[3,4-b]pyrrolo-1(2H)-yl)-4-(2,4,5-trifluorophenyl)butan-1-one fumarate compound 21

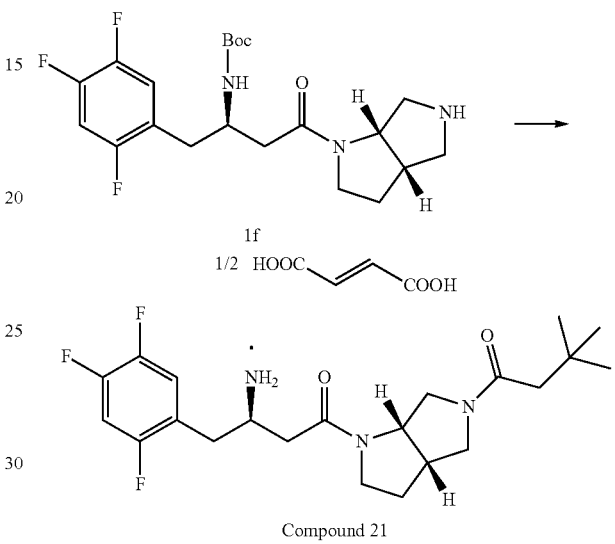

Compound 21

According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with 3,3-dimethylbutyric acid (47 mg, 0.46 mmol), intermediate was harvested by column chromatography, again added fumaric acid (27 mg, 0.245 mmol) to give target compound 21 (111 mg, 50%). MS m/z (ESI): 426.4 (M+1), 448.4 (M+Na). $^1$H NMR (CD$_3$OD, 600 MHz): δ 1.06 (s, 9H), 1.84 (m, 1H), 2.04-2.17 (m, 3H), 2.88 (m, 3H), 3.42 (m, 2H), 3.54 (m, 3H), 3.65 (m, 2H), 3.71 (m, 2H), 3.83-3.94 (m, 1H), 4.42 (m, 1H), 6.95 (m, 1H), 7.17 (m, 1H).

Example 22

Preparation of (R)-3-amino-1-((3aS,6aS)-5-(2-hydroxyl-2-methylpropionyl)-hexahydropyrrolo[3,4-b]pyrrol-1(2H)-yl)-4-(2,4,5-trifluorophenyl)butan-1-onefumarate compound 22

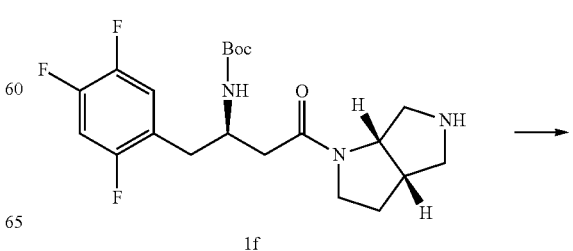

1f 3.33-3.50 (m, 1H), 3.50-3.64 (m, 4H), 3.70-3.87 (m, 2H), 4.36-4.55 (m, 3H), 6.68 (s, 1H), 7.19 (m, 1H), 7.35 (m, 1H).

Example 24

Preparation of (R)-3-amino-1-((3aS,6aS)-5-(1-hydroxymethyl 2-hydroxylpropionyl)-hexahydropyrrolo[3,4-b]pyrrol-1(2H)-yl)-4-(2,4,5-trifluorophenyl)butan-1-one fumarate compound 24

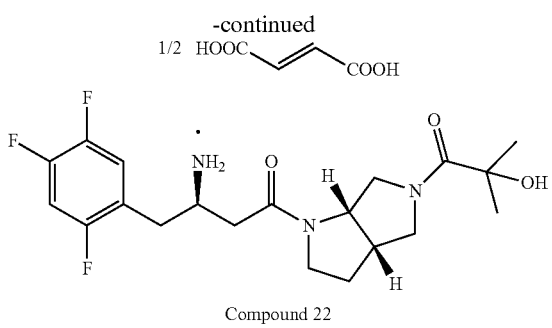

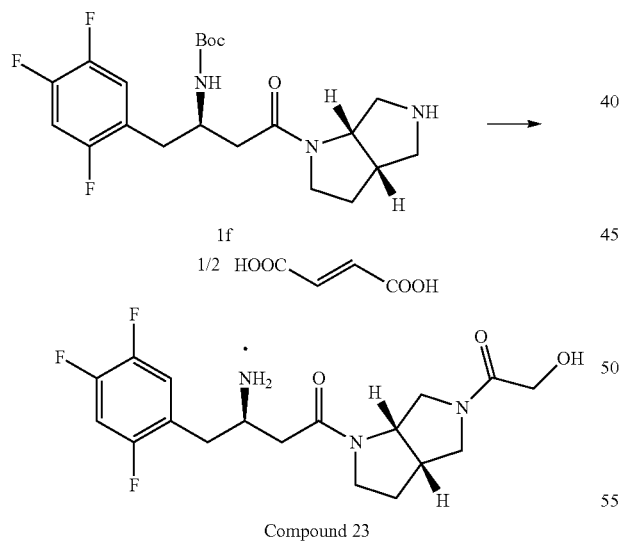

Compound 22

According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with 2-hydroxyl-2-methylpropionic acid (49 mg, 0.46 mmol), intermediate was harvested by column chromatography, again added fumaric acid (27 mg, 0.24 mmol) to give target compound 22 (56 mg, 26%). MS m/z (ESI): 414.4 (M+1). $^1$H NMR (CD$_3$OD, 600 MHz): δ 1.26 (m, 6H), 1.91 (m, 1H), 2.18 (m, 1H), 2.90 (m, 1H), 3.15 (m, 3H), 3.45 (m, 1H), 3.69 (m, 5H), 3.89 (m, 2H), 4.06 (m, 1H), 4.55 (m, 1H), 6.68 (s, 1H), 7.23 (m, 1H), 7.34 (m, 1H).

Example 23

Preparation of (R)-3-amino-1-((3aS,6aS)-5-(hydroxylacetyl)-hexahydropyrrolo[3,4-b]pyrrol-1(2H)-yl)-4-(2,4,5-trifluorophenyl)butan-1-one fumarate compound 23

Compound 23

According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with 2-hydroxylacetic acid (35 mg, 0.46 mmol), intermediate was harvested by column chromatography, again added fumaric acid (27 mg, 0.245 mmol) to give target compound 23 (74 mg, 36%). MS m/z (ESI): 386.3 (M+1). $^1$H NMR (CD$_3$OD, 600 MHz): δ 1.72-1.94 (m, 1H), 2.00-2.20 (m, 1H), 2.67 (m, 1H), 2.93-3.10 (m, 4H), According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with 3-hydroxyl-2-(hydroxymethyl)propionic acid (55 mg, 0.46 mmol) (purchased fro, J&K scientific Co. Ltd.), intermediate was harvested by column chromatography, again added fumaric acid (27 mg, 0.24 mmol) to give target compound 24 (33 mg, 15%). MS m/z (ESI): 430.3 (M+1). $^1$H NMR (CD$_3$OD, 600 MHz): δ 1.78-1.94 (m, 1H), 2.05-2.20 (m, 1H), 2.62 (m, 1H), 2.68 (m, 1H), 2.94-3.11 (m, 4H), 3.31-3.51 (m, 1H), 3.50-3.64 (m, 4H), 3.71-3.87 (m, 6H), 4.35-4.54 (m, 1H), 6.68 (s, 1H), 7.19 (m, 1H), 7.35 (m, 1H).

Example 25

Preparation of (R)-3-amino-1-((3aS,6aS)-5-(pyrrol-2-yl)-hexahydropyrrolo[3,4-b]pyrrol-1(2H)-yl)-4-(2,4,5-trifluorophenyl)butan-1-one fumarate compound 25

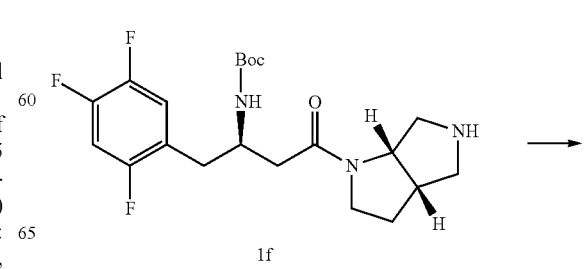

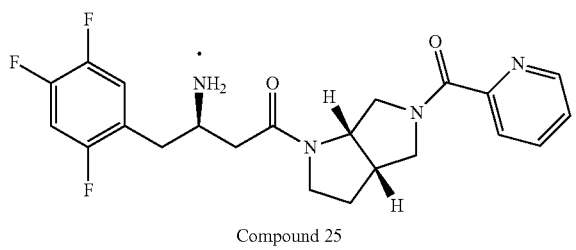

Compound 25

According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with picoline (56 mg, 0.46 mmol), intermediate was harvested by column chromatography, again added fumaric acid (53 mg, 0.46 mmol) to give target compound 25 (42 mg, 17%). MS m/z (ESI): 433.4 (M+1). $^1$H NMR (CD$_3$OD, 600 MHz): δ 1.96 (m, 1H), 2.16 (m, 1H), 2.80-2.91 (m, 2H), 2.97-3.43 (m, 3H), 3.44-3.85 (m, 5H), 3.90 (m, 2H), 4.43 (m, 1H), 6.62 (s, 1H), 6.70 (m, 1H), 7.18 (m, 1H), 7.88 (m, 1H), 8.09-8.32 (m, 3H).

Example 26

Preparation of (R)-3-amino-1-((3aS,6aS)-5-(3-mesylbenzoyl)-hexahydropyrrolo[3,4-b]pyrrol-1(2H)-yl)-4-(2,4,5-trifluorophenyl)butan-1-one fumarate compound 26

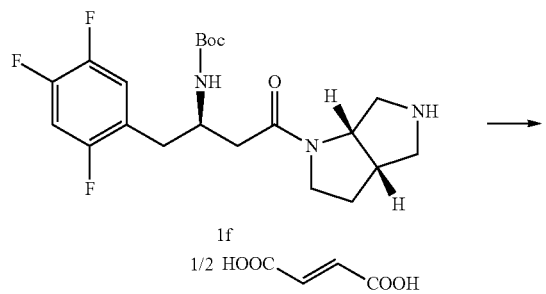

Compound 26

According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with 3-mesylbenzoic acid (92 mg, 0.46 mmol), intermediate was harvested by column chromatography, again added fumaric acid (27 mg, 0.23 mmol) to give target compound 26 (23 mg, 9%). MS m/z (ESI): 510.5 (M+1), 532.5 (M+Na). $^1$H NMR (CD$_3$OD, 600 MHz): δ 2.75-3.05 (m, 5H), 3.07-3.42 (m, 5H), 3.55-4.18 (m, 7H), 4.42 (m, 1H), 6.68 (s, 1H), 7.16-7.36 (m, 2H), 7.72-8.14 (m, 4H).

Example 27

Preparation of (R)-3-amino-1-((3aS,6aS)-5-(3-acetylbenzoyl)-hexahydropyrrolo[3,4-b]pyrrol-1(2H)-yl)-4-(2,4,5-trifluorophenyl)butan-1-one fumarate compound 27

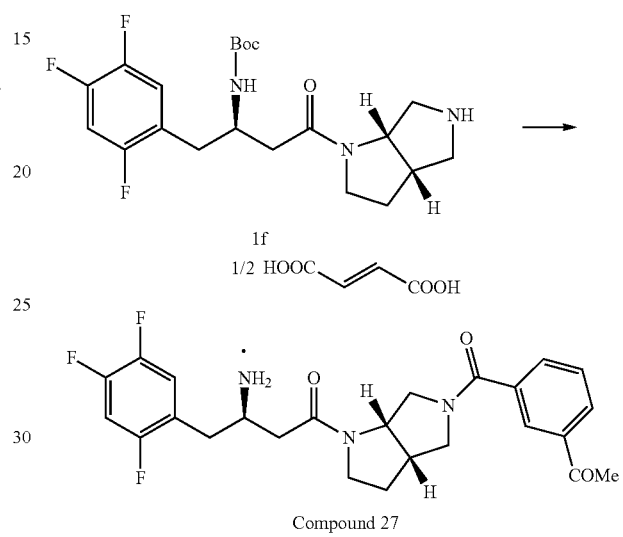

Compound 27

According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with 3-acetylbenzoic acid (75 mg, 0.46 mmol), intermediate was harvested by column chromatography, again added fumaric acid (27 mg, 0.23 mmol) to give target compound 27 (37 mg, 15%). MS m/z (ESI): 474.5 (M+1). $_1$H NMR (CD$_3$OD, 600 MHz): δ 1.74-2.76 (m, 2H), 2.65 (s, 3H), 2.71 (m, 1H), 2.88 (m, 1H), 2.96 (m, 1H), 3.15 (m, 1H), 3.38 (m, 1H), 3.53-3.64 (m, 4H), 3.65-3.86 (m, 3H), 4.40 (m, 1H), 6.64 (s, 1H), 7.08-7.33 (m, 2H), 7.55-7.75 (m, 2H), 7.92-8.12 (m, 2H).

Example 28

Step 1: Preparation of (R)-4-((3aS,6aS)-5-(1-aminocarbonylcyclopropylcarbonyl)-hexahydropyrrolo[3,4-b]pyrrol-1(2H)-yl)-4-carbonyl-1-(2,4,5-trifluorophenyl)butan-2-yltertbutyl carbamate 28a

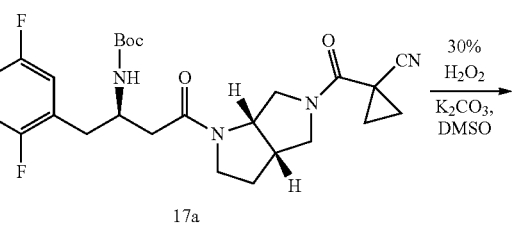

17a

-continued

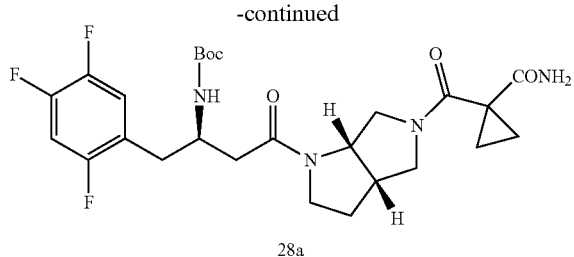

28a (R)-4-((3aS,6aS)-5-(1-cyanocyclopropylcarbonyl)-hexahydropyrrolo[3,4-b]pyrrol-1(2H)-yl)-4-carbonyl-1-(2,4,5-trifluorophenyl)butan-2-yltertbutyl carbamate 17a (300 mg, 0.58 mmol) was dissolved in DMSO (5 mL), added 30% of hydrogen peroxide (0.5 mL) and potassium carbonate (160 mg, 1.16 mmol) at 0° C., the temperature of reaction solution was raised to room temperature and stirred for 5 minutes, added water (20 mL), extracted by dichloromethane, dried by anhydrous sodium sulfate, concentrated, residues was purified by column chromatography to give (R)-4-((3aS,6aS)-5-(1-aminocarbonylcyclopropylcarbonyl)-hexahydropyrrolo[3,4-b]pyrrol-1(2H)-yl)-4-carbonyl-1-(2,4,5-trifluorophenyl)butan-2-yltertbutyl carbamate 28a (265 mg, 85%) as white foamy solid. MS m/z (ESI): 539.2 (M+1).

Step 2: Preparation of (R)-3-amino-1-((3aS,6aS)-5-(1-aminocarbonylcyclopropylcarbonyl)-hexahydropyrrolo[3,4-b]pyrrol-1(2H)-yl)-4-(2,4,5-trifluorophenyl)butan-1-one fumarate compound 28

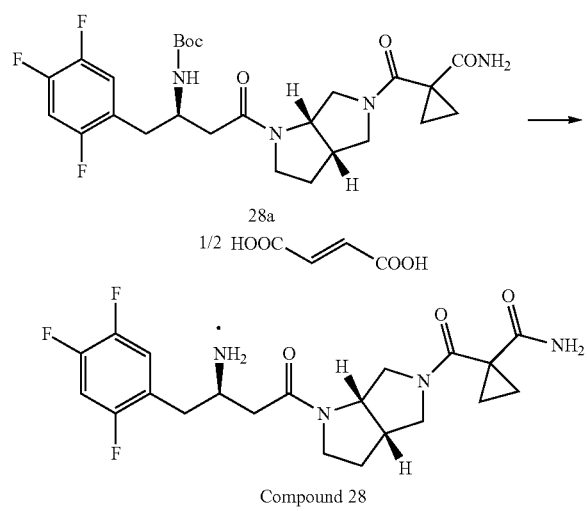

According to manipulation similar to example 12, (R)-4-((3aS,6aS)-5-(1-aminocarbonylcyclopropylcarbonyl)-hexahydropyrrolo[3,4-b]pyrrol-1(2H)-yl)-4-carbonyl-1-(2,4,5-trifluorophenyl)butan-2-yltertbutyl carbamate 28a (265 mg, 0.49 mmol) was dissolved in trifluoroacetic acid (5 mL), the resultant compound formed salt with fumaric acid (29 mg, 0.25 mmol) to give title compound 28 (136 mg, 56%) as white solid. MS m/z (ESI): 497.2 (M+1). $^1$H NMR (CD$_3$OD, 600 MHz): δ 1.58 (m, 2H), 1.65 (m, 2H), 1.91 (m, 1H), 2.15 (m, 1H), 2.63-2.81 (m, 2H), 2.91-3.26 (m, 4H), 3.53-3.65 (m, 4H), 4.05 (m, 2H), 4.37 (m, 1H), 6.69 (s, 1H), 7.17 (m, 1H), 7.29 (m, 1H).

Example 29

Step 1: Preparation of tertbutyl(R)-1-(2,4,5-trifluorophenyl)-4-((3aS,6aS)-hexahydro-5-(acetyl)-pyrrolo[3,4-b]pyrrol-1(2H)-yl)-4-oxybutan-2-ylcarbamate 29a

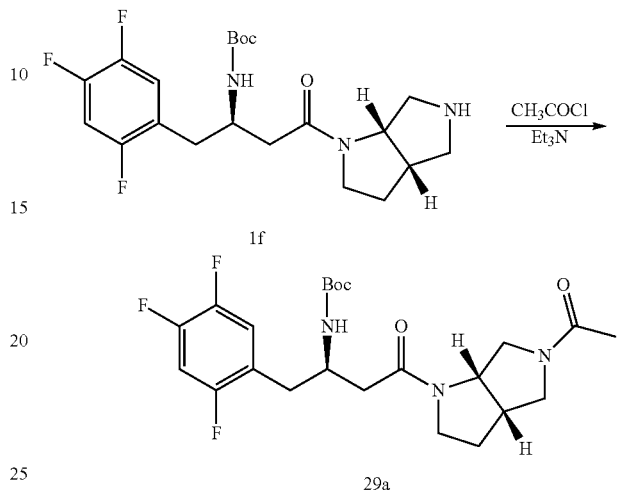

Tertbutyl(R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) was dissolved in dichloromethane (20 mL), added sequentially triethylamine (46 mg, 0.46 mmol) and acetyl chloride (36 mg, 0.46 mmol), stirred overnight at room temperature. Water (10 mL) was added into reaction solution, separated organic phase, aqueous phase was extracted by dichloromethane (20 mL), dried by anhydrous sodium sulfate, concentrated, residues was purified by column chromatography to give title compound 29a (207 mg, 96%) as white solid. MS m/z (ESI): 470.2 (M+1).

Step 2: Preparation of (R)-3-amino-1-((3aS,6aS)-5-(acetyl)-hexahydropyrrolo[3,4-b]pyrrol-1(2H)-yl)-4-(2,4,5-trifluorophenyl)butan-1-one fumarate compound 29

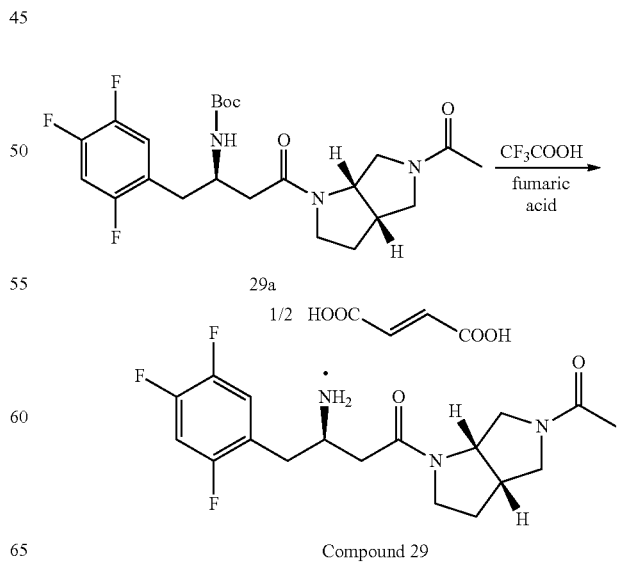

Tertbutyl(R)-1-(2,4,5-trifluorophenyl)-4-((3aS,6aS)-hexahydro-5-(acetyl)-pyrrolo[3,4-b]pyrrol-1(2H)-yl)-4-oxybutan-2-ylcarbamate 29a (207 mg, 0.44 mmol) was dissolved in dichloromethane (1 mL), added dropwise trifluoroacetic acid (TFA) (1 mL), stirred for 1 hours at room temperature, after TLC monitoring reaction was over, concentrated, added dichloromethane (15 mL), washed with saturated sodium carbonate aqueous solution (15 mL), organic phase was dried by anhydrous sodium sulfate, concentrated, residues was dissolved in ethanol, added fumaric acid (23 mg, 0.22 mmol), stirred for 30 minutes at room temperature, precipitated solid, sucking filtrated to give title compound 29 (118 mg, 63%) as white solid. MS m/z (ESI): 370.4 (M+1). $^1$H NMR (D$_2$O, 400 MHz): δ 1.72-1.94 (m, 1H), 2.03 (d, 3H), 2.00-2.20 (m, 2H), 2.67 (m, 2H), 2.93-3.10 (m, 4H), 3.33-3.50 (m, 1H), 3.50-3.64 (m, 2H), 3.70-3.87 (m, 2H), 4.36-4.55 (m, 1H), 6.69 (s, 1H), 7.18-7.28 (m, 1H), 7.28-7.40 (m, 1H).

Example 30

Preparation of (R)-3-amino-1-((3aS,6aS)-5-(trifluoroacetyl)-hexahydropyrrolo[3,4-b]pyrrol-1(2H)-yl)-4-(2,4,5-trifluorophenyl)butan-1-one fumarate compound 30

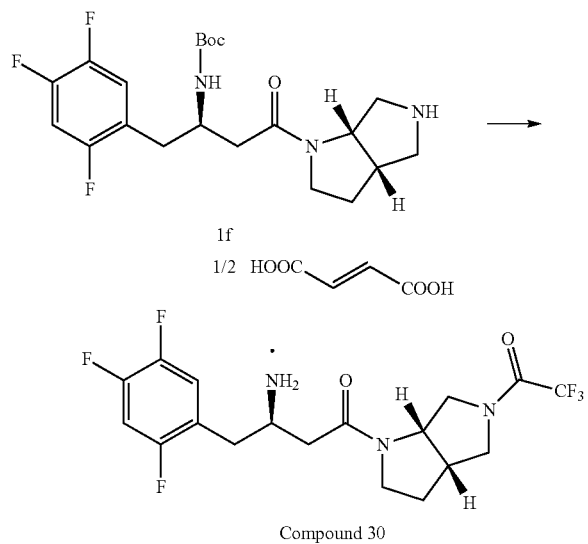

Compound 30

According to manipulation similar to example 29, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with trifluoroacetic anhydride (97 mg, 0.46 mmol), intermediate was harvested by column chromatography, again added fumaric acid (27 mg, 0.23 mmol) to give target compound 30 (91 mg, 41%). MS m/z (ESI): 424.4 (M+1), 446.4 (M+Na). $^1$H NMR (CD$_3$OD, 600 MHz): δ 1.80-2.22 (m, 2H), 2.72-2.90 (m, 2H), 3.00-3.25 (m, 3H), 3.47-3.70 (m, 4H), 3.85 (m, 1H), 3.96-4.08 (m, 2H), 4.19-4.41 (m, 1H), 6.69 (s, 1H), 7.15-7.34 (m, 2H).

Example 31

Preparation of (R)-3-amino-1-((3aS,6aS)-5-(3,3,3-trifluoropropionyl)-hexahydropyrrolo[3,4-b]pyrrol-1 (2H)-yl)-4-(2,4,5-trifluorophenyl)butan-1-one fumarate compound 31

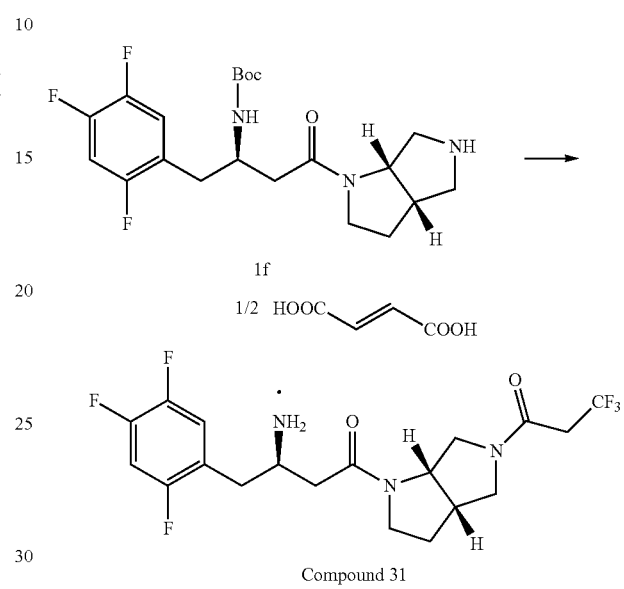

Compound 31

According to manipulation similar to example 12, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with trifluoropropionic acid (59 mg, 0.46 mmol) (purchased from Alfa Aesar (Tianjin) Co. Ltd), intermediate was harvested by column chromatography, again added fumaric acid (27 mg, 0.23 mmol) to give target compound 31 (50 mg, 22%). MS m/z (ESI): 438.4 (M+1). $^1$H NMR (CD$_3$OD, 600 MHz): δ 1.85-2.21 (m, 2H), 2.70 (s, 2H), 2.75-2.94 (m, 2H), 3.05-3.29 (m, 3H), 3.47-3.74 (m, 4H), 3.84 (m, 1H), 3.96-4.07 (m, 2H), 4.31 (m, 1H), 6.69 (s, 1H), 7.15-7.34 (m, 2H).

Example 32

Preparation of (R)-3-amino-1-((3aS,6aS)-5-(benzoyl)-hexahydropyrrolo[3,4-b]pyrrol-1(2H)-yl)-4-(2,4,5-trifluorophenyl)butan-1-one fumarate compound 32

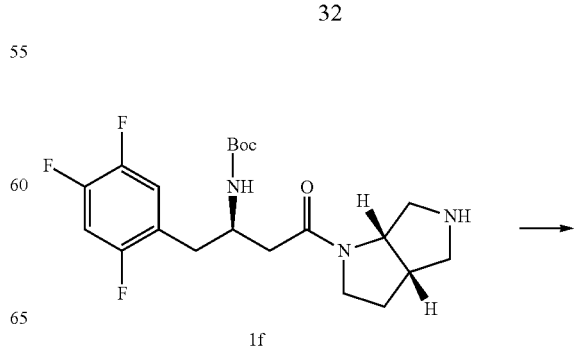

1f

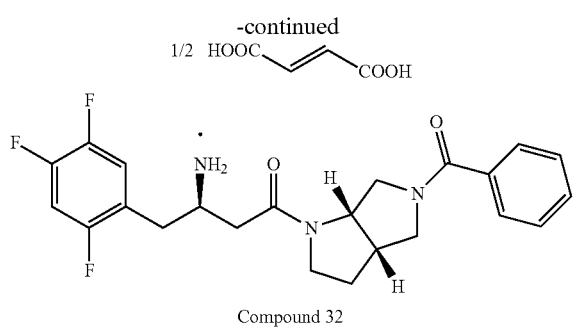

Compound 32

According to manipulation similar to example 29, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with benzoyl chloride (65 mg, 0.46 mmol), intermediate was harvested by column chromatography, again added fumaric acid (27 mg, 0.23 mmol) to give target compound 32 (81 mg, 36%). MS m/z (ESI): 432.5 (M+1), 454.4 (M+Na). $^1$H NMR (CD$_3$OD, 600 MHz): δ 1.80-2.22 (m, 2H), 2.76-3.24 (m, 4H), 3.45-4.18 (m, 8H), 4.46 (m, 1H), 6.59 (s, 1H), 7.19-7.55 (m, 7H).

Example 33

Preparation of (R)-3-amino-1-((3aS,6aS)-5-(3-fluorobenzoyl)-hexahydropyrrolo[3,4-b]pyrrol-1(2H)-yl)-4-(2,4,5-trifluorophenyl)butan-1-one fumarate compound 33

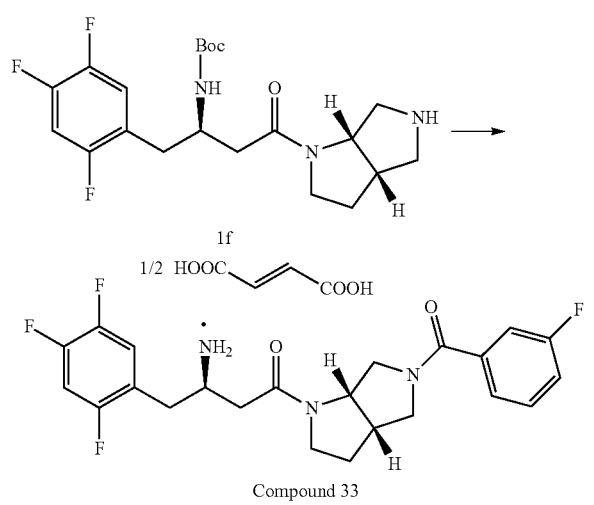

Compound 33

According to manipulation similar to example 29, tertbutyl (R)-1-(2,4,5-fluorophenyl)-4-((3aS,6aS)-hexahydropyrrolo[3,4-b]pyrrol-1(2H)-yl)-4-oxybutan-2-ylcarbamate f (200 mg, 0.46 mmol) reacted with 3-fluorobenzoyl chloride (73 mg, 0.46 mmol), intermediate was harvested by column chromatography, again added fumaric acid (27 mg, 0.23 mmol) to give target compound 33 (84 mg, 36%). MS m/z (ESI): 450.4 (M+1), 472.4 (M+Na). $^1$H NMR (CD$_3$OD, 600 MHz): δ 1.78-1.98 (m, 1H), 2.02-2.20 (m, 1H), 2.59-2.66 (m, 2H), 2.89-3.11 (m, 4H), 3.53-3.69 (m, 4H), 3.71-3.87 (m, 2H), 4.40-4.12 (dd, 1H), 6.66 (s, 1H), 7.19-7.34 (m, 5H), 7.45 (m, 1H)

Example 34

Preparation of (R)-3-amino-1-((3aS,6aS)-5-(3-chlorobenzoyl)-hexahydropyrrolo[3,4-b]pyrrol-1(2H)-yl)-4-(2,4,5-trifluorophenyl)butan-1-one fumarate compound 34

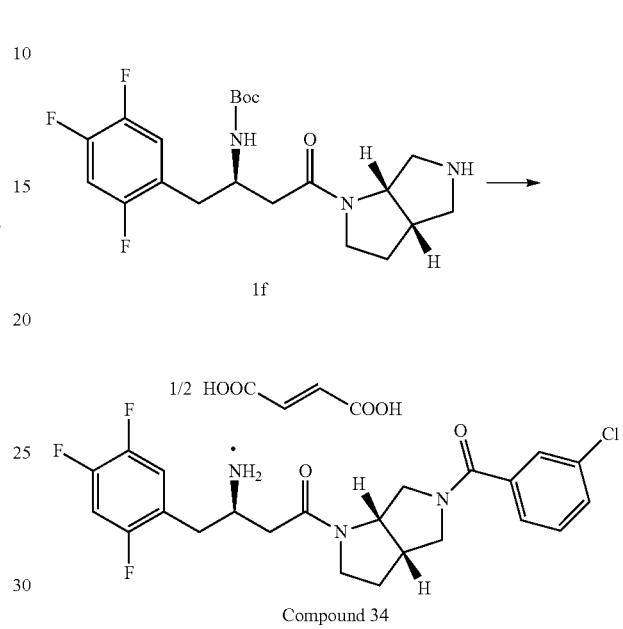

Compound 34

According to manipulation similar to example 29, tertbutyl (R)-1-(2,4,5-fluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with 3-chlorobenzoyl chloride (80 mg, 0.46 mmol), intermediate was harvested by column chromatography, again added fumaric acid (27 mg, 0.23 mmol) to give target compound 34 (89 mg, 37%). MS m/z (ESI): 466.4 (M+1). $^1$H NMR (CD$_3$OD, 600 MHz): δ 1.61-1.92 (m, 1H), 1.94-2.19 (m, 1H), 2.71 (m, 2H), 2.90-2.95 (m, 2H), 3.04-3.24 (m, 2H), 3.36-3.40 (m, 2H), 3.73-3.99 (m, 2H), 4.38 (br, 1H), 6.52 (s, 1H), 7.00-7.16 (m, 2H), 7.27 (m, 2H), 7.33-7.40 (m, 1H), 7.42-7.46 (m, 1H).

Example 35

Preparation of (R)-3-amino-1-((3aS,6aS)-5-(3-methylbenzoyl)-hexahydropyrrolo[3,4-b]pyrrol-1(2H)-yl)-4-(2,4,5-trifluorophenyl)butan-1-one fumarate compound 35

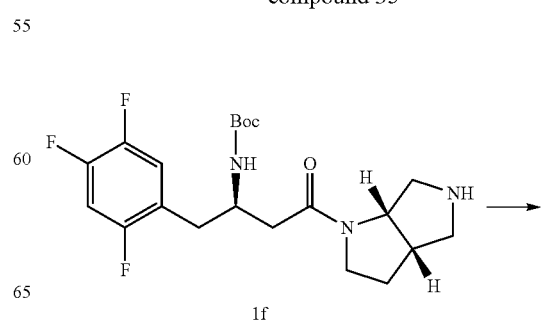

1f

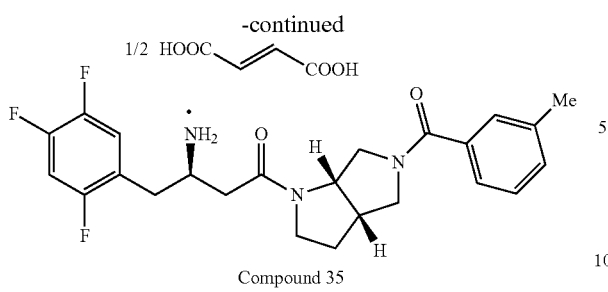

Compound 35

According to manipulation similar to example 29, tertbutyl (R)-1-(2,4,5-fluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with 3-methylbenzoyl chloride (62 mg, 0.46 mmol), intermediate was harvested by column chromatography, again added fumaric acid (27 mg, 0.23 mmol) to give target compound 35 (116 mg, 50%). MS m/z (ESI): 446.4 (M+1). $^1$H NMR (CD$_3$OD, 600 MHz): δ 1.78-1.95 (m, 1H), 2.14-2.19 (m, 1H), 2.33-2.38 (d, 3H), 2.58-2.70 (m, 2H), 2.88-2.91 (m, 1H), 2.97-3.08 (m, 2H), 3.56-3.69 (m, 1H), 3.76-3.85 (m, 2H), 4.39-4.49 (dd, 1H), 6.66 (s, 1H), 7.20-7.35 (m, 6H).

Example 36

Preparation of (R)-3-amino-1-((3aS,6aS)-5-(3-cyanobenzoyl)-hexahydropyrrolo[3,4-b]pyrrol-1(2H)-yl)-4-(2,4,5-trifluorophenyl)butan-1-one fumarate compound 36

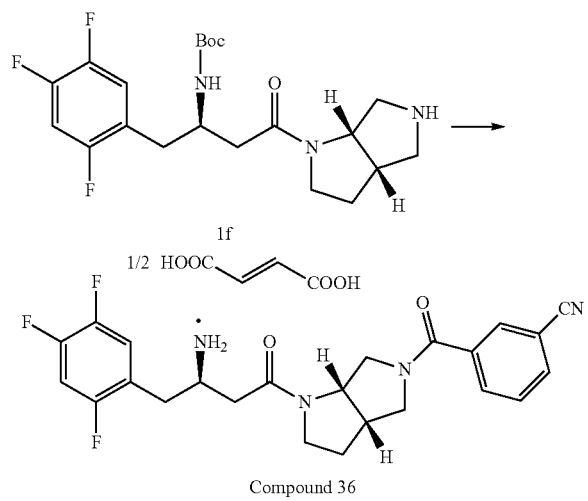

Compound 36

According to manipulation similar to example 29, tertbutyl (R)-1-(2,4,5-fluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with 3-cyanobenzoyl chloride (76 mg, 0.46 mmol), intermediate was harvested by column chromatography, again added fumaric acid (27 mg, 0.23 mmol) to give target compound 36 (78 mg, 33%). MS m/z (ESI): 457.4 (M+1), 479.5 (M+23). $^1$H NMR (CD$_3$OD, 600 MHz): δ 2.00-2.17 (m, 1H), 2.71-3.10 (m, 4H), 3.16 (m, 1H), 3.56-3.69 (m, 1H), 3.33-3.41 (m, 1H), 3.52-3.74 (m, 5H), 3.80-3.88 (m, 2H), 4.07-4.42 (m, 1H), 6.66 (s, 1H), 7.15-7.36 (m, 2H), 7.60-7.70 (m, 1H), 7.73-7.84 (m, 1H), 7.89-7.94 (m, 2H).

Example 37

Step 1: Preparation of tertbutyl(R)-1-(2,4,5-trifluorophenyl)-4-((3aS,6aS)-hexahydro-5-(cyclopropylsulfuryl)-pyrrolo[3,4-b]pyrrol-1(2H)-yl)-4-oxybutan-2-ylcarbamate 37a

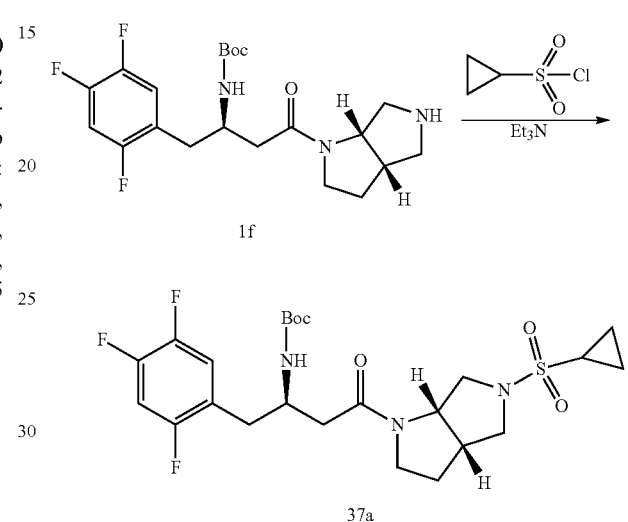

Tertbutyl(R)-1-(2,4,5-trifluorophenyl)-4-((3aS,6aS)-hexahydropyrrolo[3,4-b]pyrrol-1(2H)-yl)-4-oxybutan-2-yl-carbamate 1f (200 mg, 0.46 mmol) was dissolved in dichloromethane (20 mL), added sequentially triethylamine (46 mg, 0.46 mmol) and cyclopropylsulfonyl chloride (64 mg, 0.46 mmol), stirred overnight at room temperature. Water (10 mL) was added into reaction solution, separated organic phase, aqueous phase was extracted by dichloromethane (20 mL), dried by anhydrous sodium sulfate, concentrated, residues was purified by column chromatography to give title compound 37a (260 mg, 70%) as white solid. MS m/z (ESI): 532.2 (M+1).

Step 2: Preparation of (R)-3-amino-1-((3aS,6aS)-5-(cyclopropylsulfonyl)-hexahydropyrrolo[3,4-b]pyrrol-1(2H)-yl)-4-(2,4,5-trifluorophenyl)butan-1-one fumarate 37

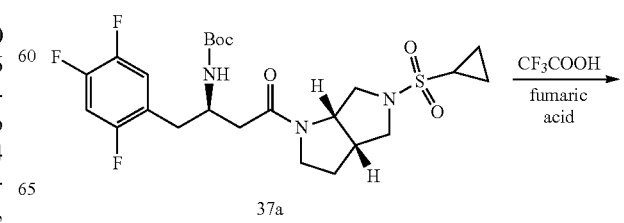

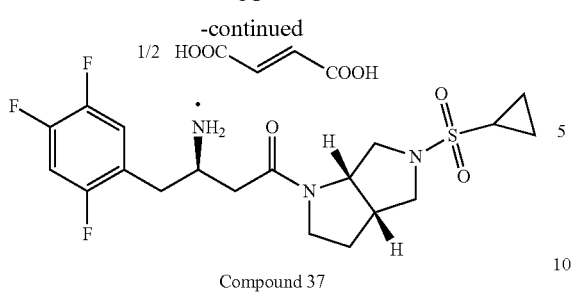

Compound 37

Tertbutyl(R)-1-(2,4,5-trifluorophenyl)-4-((3aS,6aS)-hexahydro-5-(cyclopropylbenzonyl)-pyrrolo[3,4-b]pyrrol-1(2H)-yl)-4-oxybutan-2-ylcarbamate 37a (260 mg, 0.48 mmol) was dissolved in dichloromethane (1 mL), added trifluoroacetic acid (TFA) (1 mL), stirred for 1 hours at room temperature, after TLC monitoring was over, concentrated, added dichloromethane (15 mL), washed with saturated sodium carbonate aqueous solution (15 mL), organic phase was dried by anhydrous sodium sulfate, concentrated, residues was dissolved in ethanol, added fumaric acid (28 mg, 0.24 mmol), stirred for 30 minutes at room temperature, precipitated solid, sucking filtrated to give title compound 37 (82 mg, 35%) as white solid. MS m/z (ESI): 432.4 (M+1). $^1$H NMR (D$_2$O, 400 MHz): δ 1.35 (m, 4H), 1.94 (m, 1H), 2.20 (m, 1H), 2.68 (m, 1H), 2.83 (m, 1H), 3.15 (m, 4H), 3.29 (m, 1H), 3.40 (m, 1H), 3.62 (m, 3H), 4.01 (m, 1H), 4.52 (m, 1H), 4.66 (m, 2H), 6.66 (s, 1H), 7.23 (m, 1H), 7.34 (m, 1H).

Example 38

Preparation of (R)-3-amino-1-((3aS,6aS)-5-(mesyl)-hexahydropyrrolo[3,4-b]pyrrol-1(2H)-yl)-4-(2,4,5-trifluorophenyl)butan-1-one fumarate compound 38

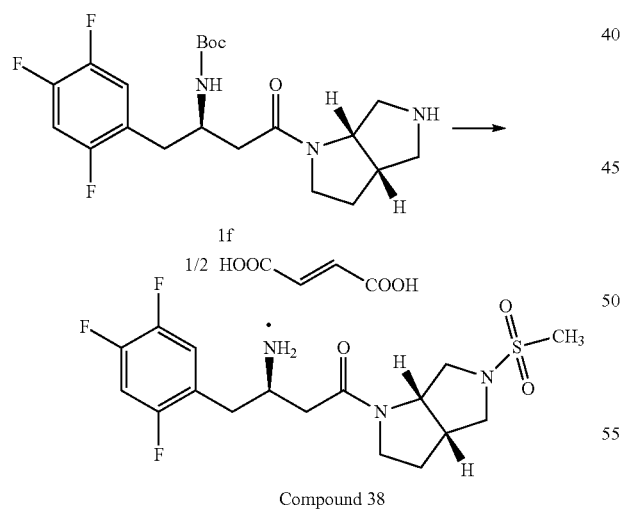

Compound 38

According to manipulation similar to example 37, tertbutyl (R)-1-(2,4,5-fluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with methanesulfonyl chloride (52 mg, 0.46 mmol), intermediate was harvested by column chromatography, again added fumaric acid (27 mg, 0.23 mmol) to give target compound 38 (55 mg, 26%). MS m/z (ESI): 406.3 (M+1). $^1$H NMR (CD$_3$OD, 600 MHz): δ 1.92 (m, 1H), 2.15 (m, 1H), 2.71-2.85 (m, 2H), 3.10-3.00 (m, 5H), 3.26 (m, 1H), 3.32 (m, 1H), 3.49 (m, 2H), 3.65 (m, 2H), 3.98 (m, 1H), 4.46 (m, 1H), 6.64 (s, 1H), 7.16-7.32 (m, 2H).

Example 39

Preparation of (R)-3-amino-1-((3aS,6aS)-5-(trifluoromesyl)-hexahydropyrrolo[3,4-b]pyrrol-1(2H)-yl)-4-(2,4,5-trifluorophenyl)butan-1-onefumarate compound 39

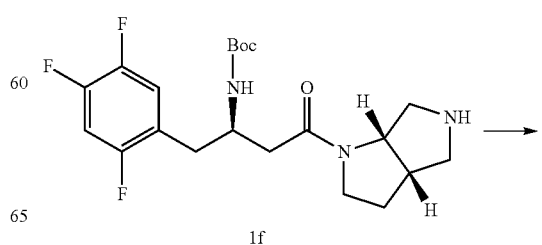

Compound 39

According to manipulation similar to example 37, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with trifluoromethanesulfonyl chloride (67 mg, 0.46 mmol), intermediate was harvested by column chromatography, again added fumaric acid (27 mg, 0.23 mmol) to give target compound 39 (107 mg, 45%). MS m/z (ESI): 460.4 (M+1). $^1$H NMR (CD$_3$OD, 600 MHz): δ 1.94 (m, 1H), 2.17 (m, 1H), 2.77 (m, 2H), 3.04-3.19 (m, 3H), 3.45-3.72 (m, 4H), 3.84 (m, 2H), 3.98 (m, 1H), 4.52 (m, 1H), 6.52 (s, 1H), 7.17-7.28 (m, 2H).

Example 40

Preparation of (R)-3-amino-1-((3aS,6aS)-5-(benzenesulfonyl)-hexahydropyrrolo[3,4-b]pyrrol-1(2H)-yl)-4-(2,4,5-trifluorophenyl)butan-1-one fumaric acid compound 40

1f

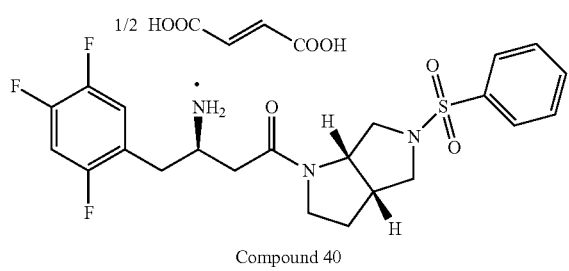

Compound 40

According to manipulation similar to example 37, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with benzenesulfonyl chloride (81 mg, 0.46 mmol), intermediate was harvested by column chromatography, again added fumaric acid (27 mg, 0.23 mmol) to give target compound 40 (123 mg, 51%). MS m/z (ESI): 468.4 (M+1). $^1$H NMR (CD$_3$OD, 600 MHz) δ 1.87 (m, 1H), 2.07 (m, 1H), 2.58 (m, 2H), 3.03-3.16 (m, 3H), 3.22 (m, 1H), 3.44-3.51 (m, 4H), 3.55 (m, 1H), 3.92 (m, 1H), 4.33 (m, 1H), 7.29 (m, 2H), 7.66 (m, 3H), 7.89 (m, 2H).

Example 41

Preparation of (R)-3-amino-1-((3aS,6aS)-5-(p-tosyl)-hexahydropyrrolo[3,4-b]pyrrol-1(2H)-yl)-4-(2,4,5-trifluorophenyl)butan-1-onefumarate compound 41

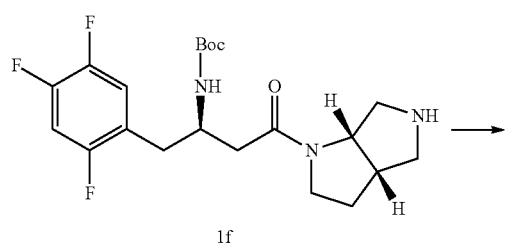

1f

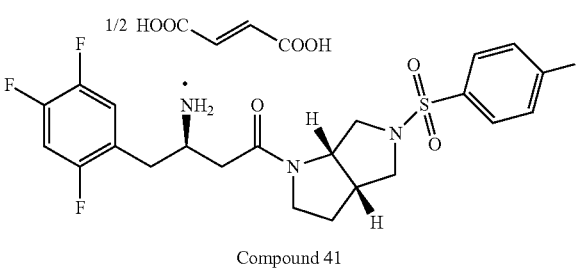

Compound 41

According to manipulation similar to example 37, tertbutyl (R)-1-(2,4,5-trifluorophenyl)-4-((3aS,6aS)-hexahydropyrrolo[3,4-b]pyrrol-1(2H)-yl)-4-oxybutan-2-ylcarbamate 1f (200 mg, 0.46 mmol) reacted with p-tosyl chloride (87 mg, 0.46 mmol), intermediate was harvested by column chromatography, again added fumaric acid (27 mg, 0.23 mmol) to give target compound 41 (131 mg, 53%). MS m/z (ESI): 482.4 (M+1), 504.4 (M+Na). $^1$H NMR (CD$_3$OD, 600 MHz): δ 1.86 (m, 1H), 2.07 (m, 1H), 2.44 (d, 3H), 3.18 (m, 3H), 3.39-3.51 (m, 5H), 3.54 (m, 2H), 3.97 (m, 2H), 4.32 (m, 1H), 6.65 (s, 1H), 7.20-7.33 (m, 2H), 7.52 (d, 2H), 7.76 (d, 2H).

Example 42

DPP-IV-Inhibiting Activity of the Compound

Determination of DPP-IV-inhibiting activity could be performed by common methods. DPP-IV was pure enzyme expressed by using baculovirus expressing system and purified. Both K$_m$ and K$_{cat}$ of pure enzyme were consistent with references, suggested that DPP-IV pure enzyme obtained by expression and purification was totally normal in enzymic properties. The reaction system was carried out in buffer of pH7.5 and the substrate was alanine-proline-7-amino-4-methylcoumarin (Ala-Pro-AMC).

DPP-IV could degradate substrate Ala-Pro-AMC to give product AMC. AMC, excited by 355 nm of ultraviolet light, could generate emitted light at 460 nm. The DPP-IV activity could be determined by dynamic detecting the increasing speed of fluorescence value at 460 nm.

Thoroughly mixed test compounds, enzyme and reaction buffer, preincubated the mixture for 15 minutes at 37° C. and then primed reaction by adding substrate, successfully detecting fluorescence value at 460 nm for 5 minutes. At the same time, set the blank control group without substrate and solvent control group with DMSO replacing test compound, as well as positive control group of Vildagliptin (LAF-237) and Sitagliptin (MK-0431) [Bioorg. Med. Chem. Lett., 2005, 15, 4770-4773]. All final reaction volumes were 100 μL. Each concentration of each sample consisted of parallel wells in triplate.

Firstly, calculated the increment of fluorescence intensity per unit time during the initial speed of enzyme (unit: RFU/sec) which can be used to express initial speed, then calculated activity percentage of sample in each concentration group as follows:

$$\text{Activity \%} = v_{sample}/v_{DMSO} * 100\%$$

Wherein, $v_{sample}$ represents initial speed of sample in each concentration group, $v_{DMSO}$ represents initial speed of DMSO group.

Logarithm concentration was plotted versus activity percentage, and then calculated fitting curve by nonlinear regression from which IC$_{50}$ value was calculated.

The molecular structural formulas of representative compounds of the present invention and the results of bioactivity test of compounds were shown in table 2.

TABLE 2
| | DPP-IV-inhibiting activity of compounds of the present invention | |
|---|---|---|
| compound | Structural formula | IC$_{50}$ (nM) |
| Compound 1 | 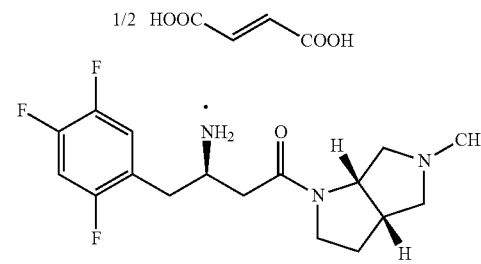 | 22.83 ± 1.99 |
| Compound 3 | 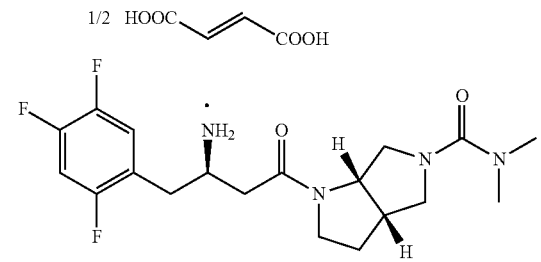 | 17.7 ± 3.77 |
| Compound 8 | 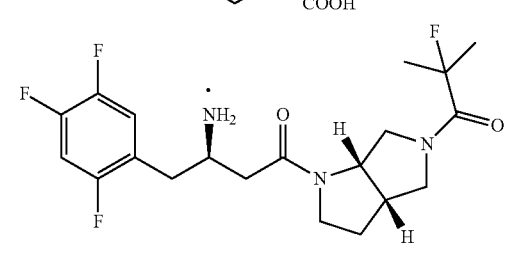 | 11.20 ± 3.76 |
| Compound 12 | 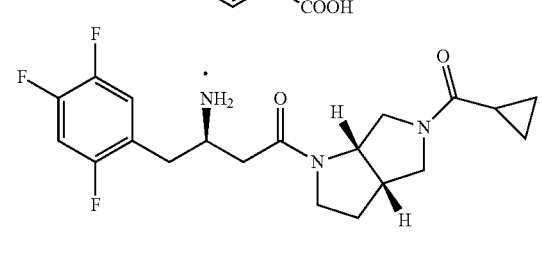 | 25.85 ± 3.91 |
| Compound 17 | 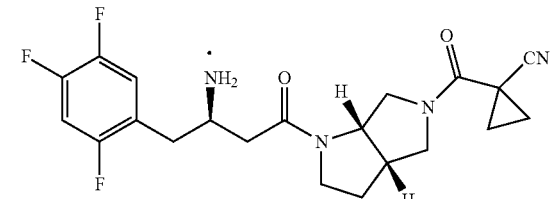 | 11.48 ± 0 |

TABLE 2-continued

DPP-IV-inhibiting activity of compounds of the present invention

| compound | Structural formula | IC$_{50}$ (nM) |
|---|---|---|
| Compound 20 | (structure: 1/2 HOOC-CH=CH-COOH salt with difluorophenyl amino amide pyrrolopyrrolidine pivaloyl) | 23.22 ± 2.24 |
| Compound 26 | (structure: 1/2 HOOC-CH=CH-COOH salt with difluorophenyl amino amide pyrrolopyrrolidine 3-methylsulfonylbenzoyl) | 2.61 ± 0.46 |
| Vildagliptin | (structure: adamantanol-NH-CH$_2$-CO-pyrrolidine-CN) | 80.10 ± 0.58 |
| Sitagliptin | (structure with H$_3$PO$_4$, difluorophenyl, NH$_2$, triazolopyrazine-CF$_3$) | 26.01 ± 3.96 |

The data in table 2 showed that the inhibiting activity against DPP-IV of compounds of the present invention was significantly stronger than that of Vidagliptin, in which the inhibiting activity of some compounds were superior than that of Sitagliptin. In particular, DPP-IV inhibiting activity of compound 26 was 30 times higher than that of Vildagliptin, 8 times higher than that of Sitagliptin. These results suggested that the compounds of the present invention had better bioactivity compared with existing drugs.

Example 43

The Selectivity of Compound for DPP-IV

Recent studies found that there were some proteins (DASH) which had activity and/or structure similar to DPP-IV, including DPP8, DPP9, FAP and the like. Preclinical studies showed that inhibition of the activity of these DASH members would lead to toxicity, even to death. So, for the treatment of diabetes, it's very important to screen DPP-IV inhibitor with high selectivity and efficacy.

The recombinant proteins of DPPIV, DPP8, DPP9 and FAP were expressed by using insect expression system (purchased from Shanghai Jinmai Biotechnology Co. Ltd). The activities of these 5 enzymes were detected by using fluorescence substrate. The inhibiting effect of compound was observed through detecting the inhibition of different compound against enzymatic activity. The employed positive reference drug was Vildagliptin (LAF237). The experimental method was according to the method disclosed in reference J. Med. Chem. 2006, 49, 3520-3535. The results were shown in table 3 and 4.

TABLE 3

IC$_{50}$ values of test compound and positive control against 5 kinds of dipeptidase (μM)

| compound | DPPIV | DPP8 | DPP9 | FAP |
|---|---|---|---|---|
| Compound 8 | 0.011 ± 0.00 | 17.63 ± 3.61 | 3.55 ± 1.02 | 13.48 ± 0.28 |
| Compound 20 | 0.023 ± 0.00 | 20.87 ± 5.63 | 5.55 ± 2.52 | 15.87 ± 4.72 |
| Compound 26 | 0.0026 ± 0.00 | 15.75 ± 7.65 | 3.45 ± 3.47 | 11.34 ± 4.02 |
| Valdagliptin | 0.080 ± 0.006 | 2.94 ± 0.39 | 0.18 ± 0.10 | 5.00 ± 0.17 |

TABLE 4

Selective ratios of test compound and positive control for dipeptidase-inhibiting activity

| compound | DPP8/DPPIV | DPP9/DPPIV | FAP/DPPIV |
| --- | --- | --- | --- |
| Compound 8 | 1602 | 322 | 1224 |
| Compound 20 | 907 | 241 | 690 |
| Compound 26 | 6057 | 1311 | 4361 |
| Valdagliptin | 37 | 2 | 63 |

The data in table 3 and 4 showed that the selective ratios of compound 8, 20 and 26 for DPP8, DPP9 and FAP were all higher than that of positive drug Valdagliptin, suggested that the compounds of the present invention had better safety than the existing positive control drugs, and were more suitable to be used to treat or prevent diseases associated with dipeptidyl peptidase IV than the existing drugs, such as diabetes.

Example 44

In Vivo Pharmacokinetic Study of Compound 8 and 20 in Rats

Experimental Methods 12 healthy, male SD rats with 200-220 g body weight were assigned randomly to 3 groups (4 in each group), particular assignment was shown in the table below:

Rats were fasted for 12 h before test with free access to water and uniformly fed at 2 h after administration.

Time points of blood collecting and samples treatment: 0.3 mL blood was drawn through mice post-glomus venous plexus at 0.25, 0.5, 1.0, 2.0, 3.0, 4.0, 5.0, 7.0, 9.0 and 24 hours post-administration, placed in heparinized test tube, centrifuged at 3000 rpm/min for 10 minutes, separated plasma, frozen in refrigerator at −20° C. Unchanged drug concentration in plasma was determined by liquid chromatography-tandem mass spectrometry method.

TABLE 5

Pharmacokinetics parameters of compound 8 and 20 after 20 mg/kg gavage administration in rats

| compound | $T_{max}$ (h) | $C_{max}$ (ng/mL) | $AUC_{0-t}$ (ngh/mL) | $T_{1/2}$ (h) |
| --- | --- | --- | --- | --- |
| Compound 8 | 1.00 | 933 | 2921 | 2.29 |
| Compound 20 | 0.81 | 917 | 2076 | 2.45 |
| Sitagliptin | 0.44 | 477 | 1655 | 2.11 |

Table 5 showed that compound 8 and 20 had larger in vivo exposure (AUC) and longer in vivo half-life ($t_{1/2}$) than positive control drug sitagliptin after gavages administration of 20 mg/k dose in rats, suggested the compound of the present invention had better in vivo pharmacokinetics properties than the currently marketed drug Sitagliptin.

Example 45

In Vivo Glucose-Decreasing Activity of Compound

Experimental Animal:

70 male clean-grade ICR mice with 20.0-24.0 g body weight were provided by Experimental Animal Center of Zhejiang University. Production license number of experimental animal: SCXK[zhe]2007-0039; Use license number of experimental animal: SYXK(zhe)2007-0098.

Feeding condition for animals: met the requirement for experimental facility of SPF grade animals, temperature at 20-25° C., humidity of 0-70%, illuminating condition was alternately 12 hours of brightness and 12 hours of darkness, ventilation rate was 10-20 times per hour, free access to water (city drinking water), illumination was 12 h/12 h of alternating light and dark at day and night respectively.

Experimental Methods:

50 male clean-grade mice passing quarantine with 20.0-24.0 g body weight were randomly divided into 5 groups which included solvent control group, model group, compound dose group (3.0 mg/kg) respectively, 10 per group.

Mice in each group were fasted for 12 hours and then 0.08 mL blood was drawn by cutting tail. Serum was collected and used to determinating fasting blood glucose value. After drawing blood, mice in each dose group were administrated by gavage with different drug solution of corresponding dose and mice in solvent control and model group were administrated with distilled water of equal volume, wherein administration volume was 0.2 mL/10 g. 0.08 mL blood was drawn from each group at 60 minutes post-administration to determine the blood glucose value at 60 minutes post-administration. After drawing blood, 5.0 mg/kg glucose was administrated by gavage to each group except for solvent control group, wherein administration volume was 0.2 mL/10 g, and then blood was drawn at 20 min, 40 min, 60 min, 120 min after administration of glucose respectively, blood was centrifugated at 6000 rpm for 10 min to separate serum for determining the blood glucose value at each time point, area under curve of blood glucose was calculated on the basis of blood glucose concentration.

TABLE 6

The influence of compound 13 and 20 on area under curve of blood glucose in normal mice (x ± s)

| group | Dose (mg/kg) | Number of animals | AUC (mmol · min/L) | inhibition rate (%) |
| --- | --- | --- | --- | --- |
| Control | — | 10 | 349 ± 65 | — |
| Model | — | 10 | 1047 ± 51 | — |
| Compound 8 | 3.0 | 10 | 129 ± 41*** | 63.0 |
| Compound 20 | 3.0 | 10 | 215 ± 44** | 38.3 |
| Sitagliptin | 3.0 | 10 | 240 ± 24** | 31.1 | t test, compared with CMC-Na solvent control group,
*$P < 0.05$,
**$P < 0.01$,
***$P < 0.001$ Table 6 showed that inhibition rate of compound 8 and 20 for blood glucose AUC of normal ICR rats at 3 mg/kg dose were 63.0% and 38.3 respectively, significantly superior to Sitagliptin, suggested that the compounds of the present invention had stronger in vivo glucose-decreasing activity than the currently marketed drug.

Example 46

Pharmaceutical Composition

| | |
| --- | --- |
| Compound 8 | 20 g |
| Starch | 140 g |
| microcrystalline cellulose | 60 g |

According to traditional method, various ingredients of pharmaceutical composition described above, after mixing, were loaded into conventional gelatine capsule to give 1000 capsules.

According to similar method, the capsules of compound 8 were produced respectively.

Example 47

Preparation of Capsules

| Compound 20 | 50 g |
|---|---|
| Starch | 400 g |
| microcrystalline cellulose | 200 g |

According to traditional method, various ingredients of pharmaceutical composition described above, after mixing, were loaded into conventional gelatin capsule to give 1000 capsules.

According to similar method, the capsules of compound 20 were produced respectively.

All the references mentioned in the invention are incorporated herein by reference, as if each reference was individually incorporated herein by reference. In addition, it should be understood that various changes or modifications can be made to the invention by those skilled in the art after reading foregoing teaching, these equivalents also fall within the scope defined by the appended claims.

We claimed:

1. A compound according to formula (I) or optical isomers, crystal forms, pharmaceutically acceptable inorganic or organic salts, hydrates or solvates thereof:

(I)

wherein,
X is selected from the group consisting of:
(1) —$C_1$-$C_3$ alkylidene;
(2) —C(O)—;
(3) —S(O)$_2$—;
(4) —C(O)O—; and
(5) —C(O)NR$^1$—;
R is selected from the group consisting of:
(1) H;
(2) $C_1$-$C_6$ alkyl, which is unsubstituted or substituted by one to three substituents selected from the following group: fluorine, chlorine or hydroxyl;
(3) $C_3$-$C_6$ cycloalkyl, which is unsubstituted or substituted by one to two substituents selected from the following group: $C_1$-$C_3$ alkyl, fluorine, chlorine, hydroxyl, cyano, C(O)NH$_2$;
(4) Phenyl, which is unsubstituted or substituted by one to three substituents selected from the followings: $C_1$-$C_3$ alkyl, fluorine, chlorine, cyano, S(O)$_2$R$^2$; and
(5) 6-membered heterocycle containing one to two atoms independently selected from N atom, above-mentioned 6-membered heterocycle is unsubstituted or substituted by one to three substituents selected from the followings: $C_1$-$C_3$ alkyl, fluorine, chlorine, cyano, S(O)$_2$R$^2$;
wherein, R$^1$ is H or $C_1$-$C_3$ alkyl;
R$^2$ is $C_1$-$C_3$ alkyl.

2. The compound of claim 1, wherein, said compound is a compound of formula (Ia):

(Ia)

wherein,
X is selected from the group consisting of:
(1) —$C_1$-$C_3$ alkylidene-;
(2) —C(O)—;
(3) —S(O)$_2$—;
(4) —C(O)O—; and
(5) —C(O)NR$^1$—;
R is selected from the group consisting of:
(1) H;
(2) $C_1$-$C_6$ alkyl, which is unsubstituted or substituted by one to three substituents selected from the following group: fluorine, chlorine or hydroxyl;
(3) $C_3$-$C_6$ cycloalkyl, which is unsubstituted or substituted by one to two substituents selected from the following group: $C_1$-$C_3$ alkyl, fluorine, chlorine, hydroxyl, cyano, C(O)NH$_2$;
(4) Phenyl, which is unsubstituted or substituted by one to three substituents selected from the followings: $C_1$-$C_3$ alkyl, fluorine, chlorine, cyano, S(O)$_2$R$^2$; and
(5) 6-membered heterocycle containing one to two N atoms, said 6-membered heterocycle is unsubstituted or substituted by one to three substituents selected from the followings: $C_1$-$C_3$ alkyl, fluorine, chlorine, cyano, S(O)$_2$R$^2$;
wherein, R$^1$ is H or $C_1$-$C_3$ alkyl;
R$^2$ is $C_1$-$C_3$ alkyl.

3. The compound of claim 2, wherein, said compound is the salt formed by the compound of formula (Ia) having general formula (Ib):

(Ib)

wherein, A is selected from acid radical of hydrochloric acid, hydrobromic acid, hydrofluoric acid, sulfuric acid, nitric acid, phosphoric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, benzenesulfonic acid, aspartic acid, or glutamic acid.

4. The compound of claim 1, wherein, X is selected from —C(O)—.

5. The compound of claim 1, wherein, said R is selected from: $C_1$-$C_6$alkyl, which is unsubstituted or substituted by one to three substituents selected from the group consisting of fluorine, chlorine and hydroxyl; and $C_3$-$C_6$ cycloalkayl, which is unsubstituted or substituted by one to two substituents selected from the group consisting of $C_1$-$C_3$ alkyl, fluorine, chlorine, hydroxyl, cyano, and $C(O)NH_2$.

6. The compound of claim 1, wherein, said compound is selected from the following compounds shown in the following table:

| compound | compound structure | compound name |
|---|---|---|
| 1 | 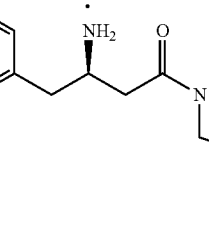 | (R)-3-amino-1-((3aS,6aS)-hexahydro-5-methylpyrrolo[3,4-b]pyrrol-1(2H)-yl)-4-(2,4,5-trifluorophenyl)but-1-anone fumarate |
| 2 | 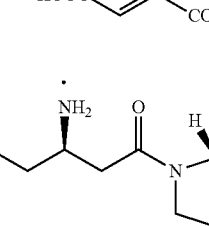 | (R)-3-amino-1-((3aS,6aS)-5-methoxycarbonylhexahydropyrrolo[3,4-b]pyrrol-1(2H)-yl)-4-(2,4,5-trifluorophenyl)but-1-anone fumarate |
| 3 | 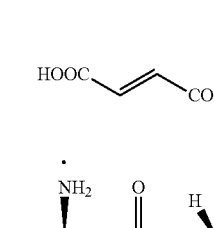 | (R)-3-amino-1-((3aS,6aS)-5-(N,N-dimethylaminoformyl)-hexahydropyrrolo[3,4-b]pyrrol-1(2H)-yl)-4-(2,4,5-trifluorophenyl)butane-1-one fumarate |
| 4 | 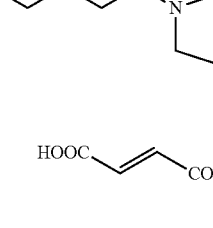 | (R)-3-amino-1-((3aS,6aS)-5-(N-methylaminoformyl)-hexahydropyrrolo[3,4-b]pyrrol-1(2H)-yl)-4-(2,4,5-trifluorophenyl)butane-1-one fumarate |
| 5 | 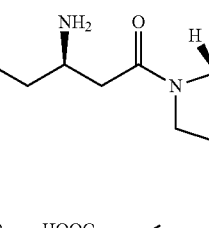 | (R)-3-amino-1-((3aS,6aS)-5-(methylaminoformyl)-hexahydropyrrolo[3,4-b]pyrrol-1(2H)-yl)-4-(2,4,5-trifluorophenyl)butane-1-one fumarate |

-continued

| compound | compound structure | compound name |
|---|---|---|
| 6 | 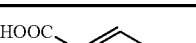 | (R)-3-amino-1-((3aS,6aS)-5-(cyclopropcarbonyl)-hexahydropyrrolo[3,4-b]pyrrol-1(2H)-yl)-4-(2,4,5-trifluorophenyl)butane-1-one fumarate |
| 7 | 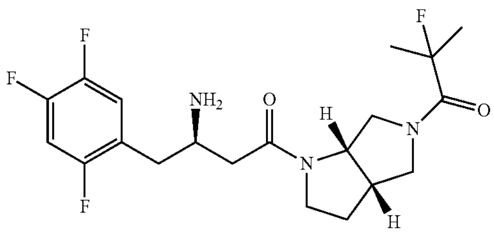 [SMILES: CC(C)(F)C(=O)N1C[C@@H]2CCN(C(=O)C[C@H](N)Cc3cc(F)c(F)cc3F)[C@@H]2C1] | (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butane-1-one |
| 8 | 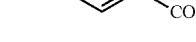 | (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butane-1-one fumarate |
| 9 | 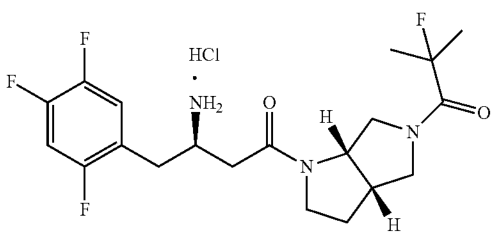 | (R)-3-amino-1-((3aS,6aS)-5-(2-fluoro-2-methylpropionyl)-hexapyrrolo[3,4-b]pyrrol-1(2H)-yl)-4-(2,4,5-trifluorophenyl)butane-1-one hydrochloride |
| 10 | 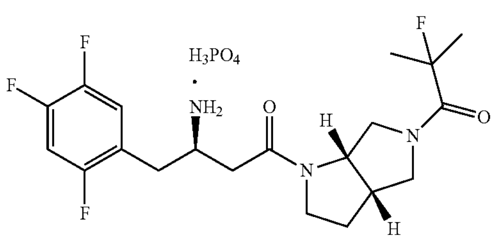 | (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butane-1-one phosphate |
| 11 | 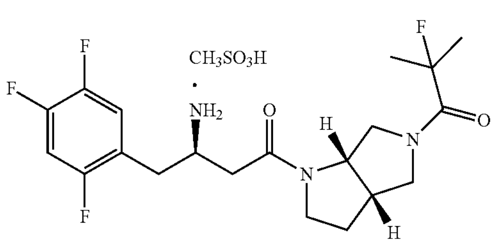 | (R)-3-amino-1-((3aS,6aS)-5-(2-fluoro-2-methylpropionyl)-hexahydropyrrolo[3,4-b]pyrrol-1(2H)-yl)-4-(2,4,5-trifluorophenyl)butane-1-one methane sulfonate |

-continued

| compound | compound structure | compound name |
|---|---|---|
| 12 |  1/2 HOOC—COOH | (R)-3-amino-1-((3aS,6aS)-5-(cyclopropcarbonyl)-hexahydropyrrolo[3,4-b]pyrrol-1(2H)-yl)-4-(2,4,5-trifluorophenyl)butane-1-one fumarate |
| 13 | 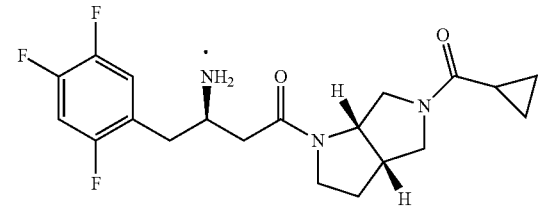 1/2 HOOC—COOH | (R)-3-amino-1-((3aS,6aS)-5-(1-fluorocyclopropylcarbonyl)-hexahydropyrrolo[3,4-b]pyrrol-1(2H)-yl)-4-(2,4,5-trifluorophenyl)butane-1-one fumarate |
| 14 |  1/2 HOOC—COOH | (R)-3-amino-1-((3aS,6aS)-5-(1-hydroxylcyclopropylcarbonyl)-hexahydropyrrolo[3,4-b]pyrrol-1(2H)-yl)-4-(2,4,5-trifluorophenyl)butane-1-one fumarate |
| 15 | 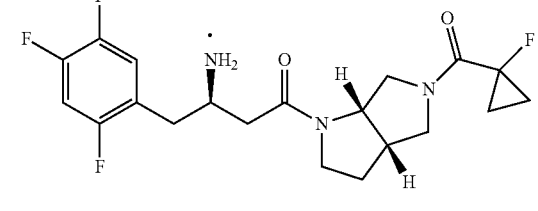 1/2 HOOC—COOH | (R)-3-amino-1-((3aS,6aS)-5-(1-methylcyclopropylcarbonyl)-hexahydropyrrolo[3,4-b]pyrrol-1(2H)-yl)-4-(2,4,5-trifluorophenyl)butane-1-one fumarate |
| 16 |  1/2 HOOC—COOH | (R)-3-amino-1-((3aS,6aS)-5-(cyclopropylmethylidenecarbonyl)-hexahydropyrrolo[3,4-b]pyrrol-1(2H)-yl)-4-(2,4,5-trifluorophenyl)butane-1-one fumarate |
| 17 | 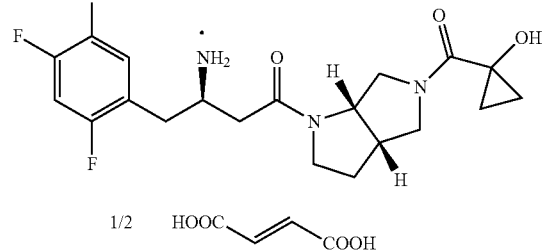 1/2 HOOC—COOH | (R)-3-amino-1-((3aS,6aS)-5-(1-cyanocyclopropylcarbonyl)-hexahydropyrrolo[3,4-b]pyrrol-1(2H)-yl)-4-(2,4,5-trifluorophenyl)butane-1-one fumarate |

| compound | compound structure | compound name |
| --- | --- | --- |
| 18 | 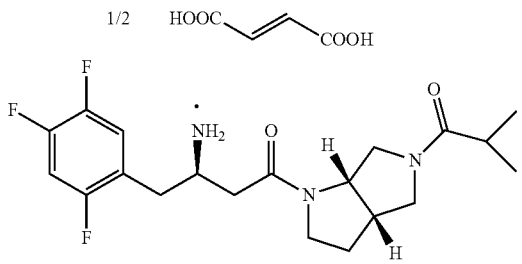 | (R)-3-amino-1-((3aS,6aS)-5-(isopropylcarbonyl)-hexahydropyrrolo[3,4-b]pyrrol-1(2H)-yl)-4-(2,4,5-trifluorophenyl)butane-1-one fumarate |
| 19 | 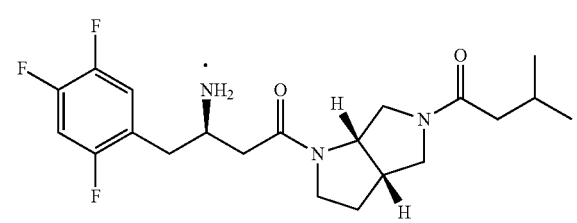 | (R)-3-amino-1-((3aS,6aS)-5-(3-methylbutyryl)-hexahydropyrrolo[3,4-b]pyrrol-1(2H)-yl)-4-(2,4,5-trifluorophenyl)butane-1-one fumarate |
| 20 | 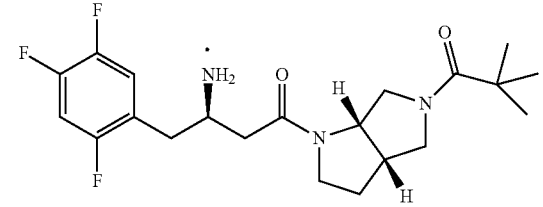 | (R)-3-amino-1-((3aS,6aS)-5-(tertvaleryl)-hexahydropyrrolo[3,4-b]pyrrol-1(2H)-yl)-4-(2,4,5-trifluorophenyl)butane-1-one fumarate |
| 21 | 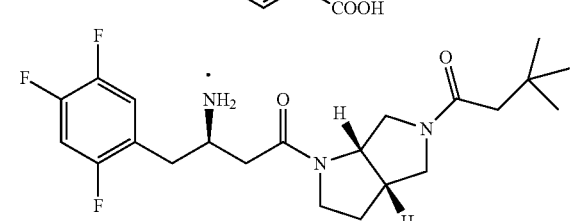 | (R)-3-amino-1-((3aS,6aS)-5-(3,3-dimethylbutyryl)-hexahydropyrrolo[3,4-b]pyrrol-1(2H)-yl)-4-(2,4,5-trifluorophenyl)butane-1-one fumarate |
| 22 | 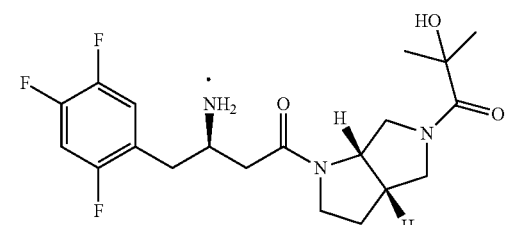 | (R)-3-amino-1-((3aS,6aS)-5-(2-hydroxyl-2-methylpropionyl)-hexahydropyrrolo[3,4-b]pyrrol-1(2H)-yl)-4-(2,4,5-trifluorophenyl)butane-1-one fumarate |

| compound | compound structure | compound name |
| --- | --- | --- |
| 23 | 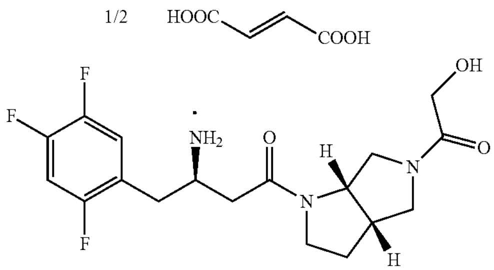 | (R)-3-amino-1-((3aS,6aS)-5-(hydroxylacetyl)-hexahydropyrrolo[3,4-b]pyrrol-1(2H)-yl)-4-(2,4,5-trifluorophenyl)butane-1-one fumarate |
| 24 | 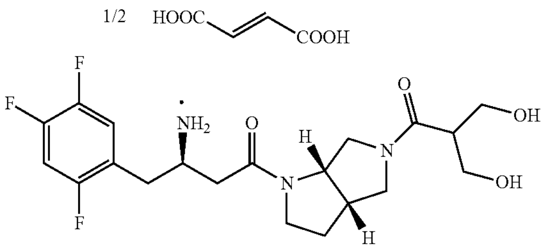 | (R)-3-amino-1-((3aS,6aS)-5-(1-hydroxymethyl2-hydroxypropionyl)-hexahydropyrrolo[3,4-b]pyrrol-1(2H)-yl)-4-(2,4,5-trifluorophenyl)butane-1-one fumarate |
| 25 | 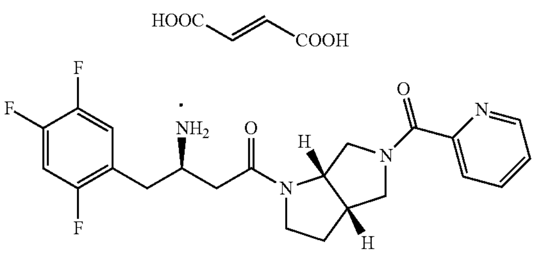 | (R)-3-amino-1-((3aS,6aS)-5-(pyrrol-2-yl)-hexahydropyrrolo[3,4-b]pyrrol-1(2H)-yl)-4-(2,4,5-trifluorophenyl)butane-1-one fumarate |
| 26 | 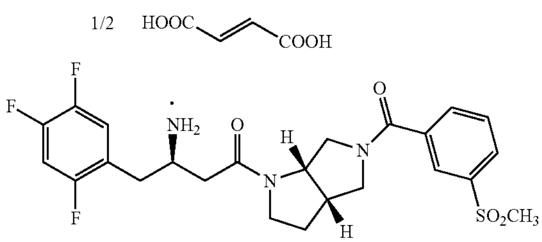 | (R)-3-amino-1-((3aS,6aS)-5-(3-mesylbenzoyl)-hexahydropyrrolo[3,4-b]pyrrol-1(2H)-yl)-4-(2,4,5-trifluorophenyl)butane-1-one fumarate |
| 27 | 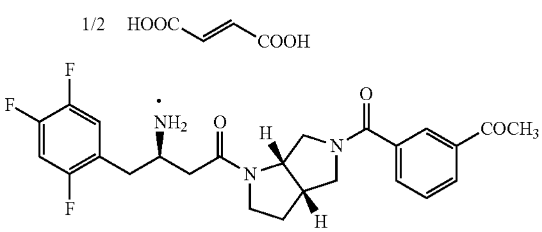 | (R)-3-amino-1-((3aS,6aS)-5-(3-acetylbenzoyl)-hexahydropyrrolo[3,4-b]pyrrol-1(2H)-yl)-4-(2,4,5-trifluorophenyl)butane-1-one fumarate |
| 28 | 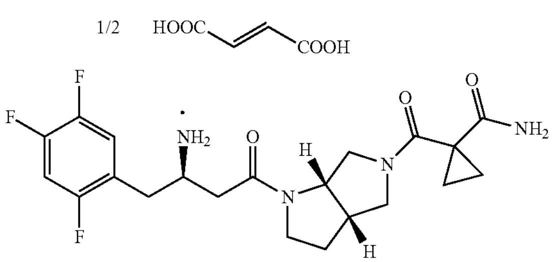 | (R)-3-amino-1-((3aS,6aS)-5-(1-aminocarbonylcyclopropylcarbonyl)-hexahydropyrrolo[3,4-b]pyrrol-1(2H)-yl)-4-(2,4,5-trifluorophenyl)butane-1-one fumarate |

-continued

| compound | compound structure | compound name |
|---|---|---|
| 29 | 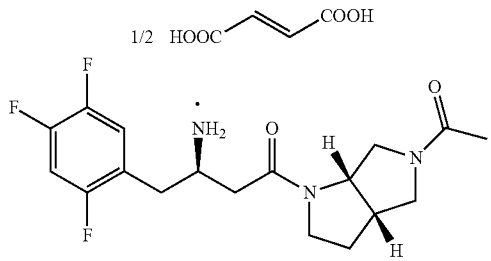 | (R)-3-amino-1-((3aS,6aS)-5-(acetyl)-hexahydropyrrolo[3,4-b]pyrrol-1(2H)-yl)-4-(2,4,5-trifluorophenyl)butane-1-one fumarate |
| 30 | 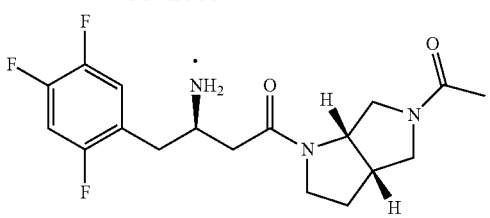 | (R)-3-amino-1-((3aS,6aS)-5-(trifluoroacetyl)-hexahydropyrrolo[3,4-b]pyrrol-1(2H)-yl)-4-(2,4,5-trifluorophenyl)butane-1-one fumarate |
| 31 | 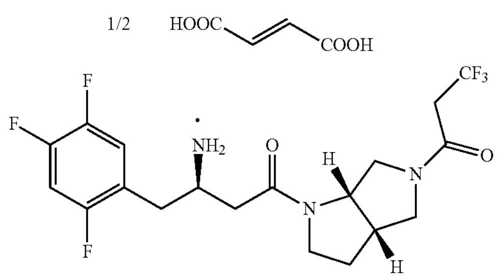 | (R)-3-amino-1-((3aS,6aS)-5-(3,3,3-trifluoropropionyl)-hexahydropyrrolo[3,4-b]pyrrol-1(2H)-yl)-4-(2,4,5-trifluorophenyl)butane-1-one fumarate |
| 32 | 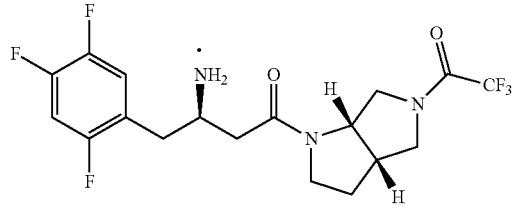 | (R)-3-amino-1-((3aS,6aS)-5-(benzoyl)-hexahydropyrrolo[3,4-b]pyrrol-1(2H)-yl)-4-(2,4,5-trifluorophenyl)butane-1-one fumarate |
| 33 | 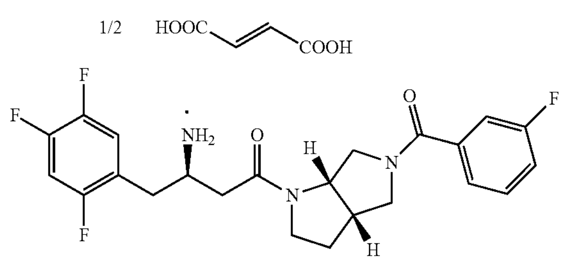 | (R)-3-amino-1-((3aS,6aS)-5-(3-fluorobenzoyl)-hexahydropyrrolo[3,4-b]pyrrol-1(2H)-yl)-4-(2,4,5-trifluorophenyl)butane-1-one fumarate |
| 34 | 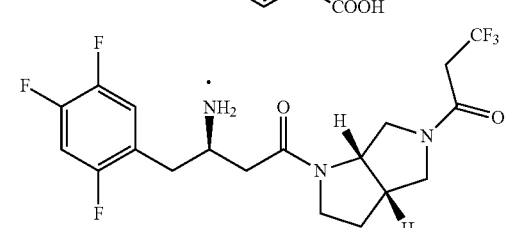 | (R)-3-amino-1-((3aS,6aS)-5-(3-chlorobenzoyl)-hexahydropyrrolo[3,4-b]pyrrol-1(2H)-yl)-4-(2,4,5-trifluorophenyl)butane-1-one fumarate |

| compound | compound structure | compound name |
|---|---|---|
| 35 | 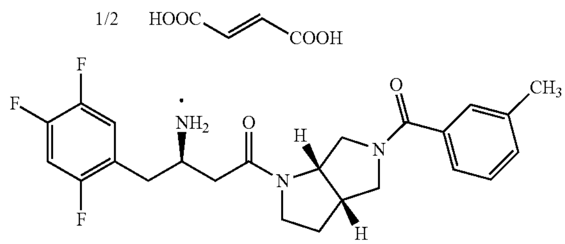 | (R)-3-amino-1-((3aS,6aS)-5-(3-methylbenzoyl)-hexahydropyrrolo[3,4-b]pyrrol-1(2H)-yl)-4-(2,4,5-trifluorophenyl)butane-1-one fumarate |
| 36 | 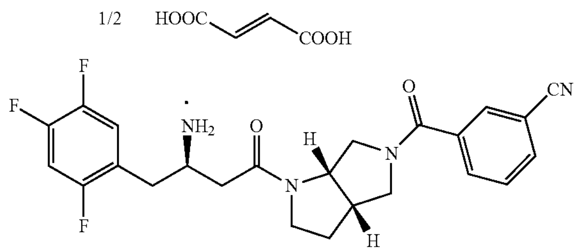 | (R)-3-amino-1-((3aS,6aS)-5-(3-cyanobenzoyl)-hexahydropyrrolo[3,4-b]pyrrol-1(2H)-yl)-4-(2,4,5-trifluorophenyl)butane-1-one fumarate |
| 37 | 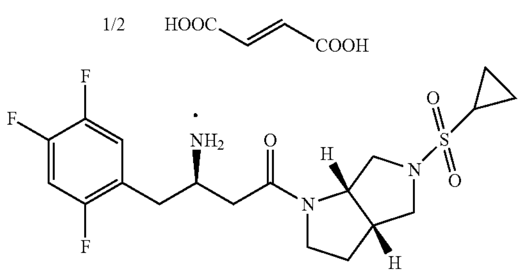 | (R)-3-amino-1-((3aS,6aS)-5-(cyclopropylsulfonyl)-hexahydropyrrolo[3,4-b]pyrrol-1(2H)-yl)-4-(2,4,5-trifluorophenyl)butane-1-one fumarate |
| 38 | 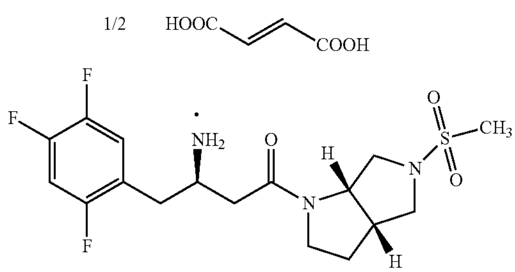 | (R)-3-amino-1-((3aS,6aS)-5-(mesyl)-hexahydropyrrolo[3,4-b]pyrrol-1(2H)-yl)-4-(2,4,5-trifluorophenyl)butane-1-one fumarate |
| 39 | 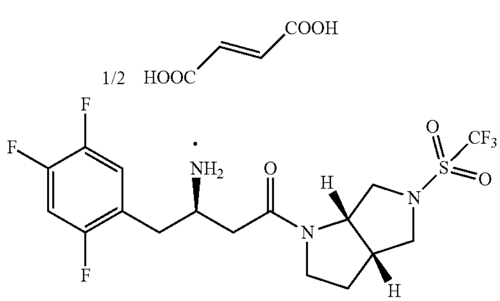 | (R)-3-amino-1-((3aS,6aS)-5-(trifluoromesyl)-hexahydropyrrolo[3,4-b]pyrrol-1(2H)-yl)-4-(2,4,5-trifluorophenyl)butane-1-one fumarate |

| compound | compound structure | compound name |
| --- | --- | --- |
| 40 | 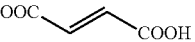 | (R)-3-amino-1-((3aS,6aS)-5-(benzenesulfonyl)-hexahydropyrrolo[3,4-b]pyrrol-1(2H)-yl)-4-(2,4,5-trifluorophenyl)butane-1-one fumarate |
| 41 | 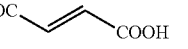 | (R)-3-amino-1-((3aS,6aS)-5-(p-tosyl)-hexahydropyrrolo[3,4-b]pyrrol-1(2H)-yl)-4-(2,4,5-trifluorophenyl)butane-1-one fumarate. |

7. A pharmaceutical composition comprising pharmaceutically acceptable excipients or carriers, and the compound of claim 1, or various optical isomers, various crystal forms, pharmaceutically acceptable inorganic or organic salts, hydrates or solvates thereof.

8. A method for preparing a compound according to formula (I), wherein, the method comprises the steps of:

(a) reacting a compound of formula (1c) with a compound of formula (1d) under a peptide coupling condition to produce a compound of formula (1e),

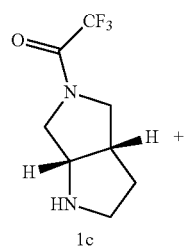

1c

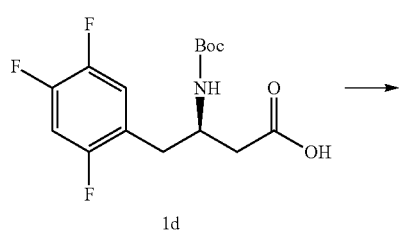

1d

-continued

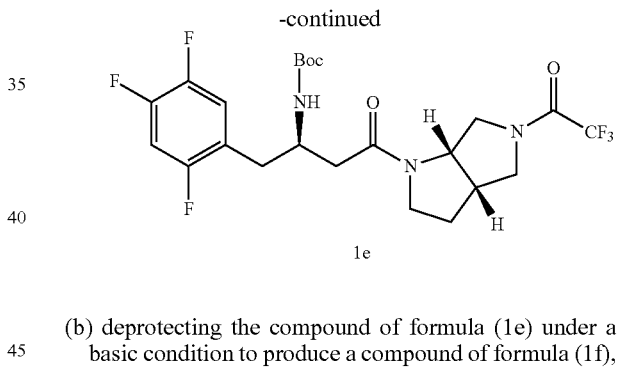

1e (b) deprotecting the compound of formula (1e) under a basic condition to produce a compound of formula (1f), 1e

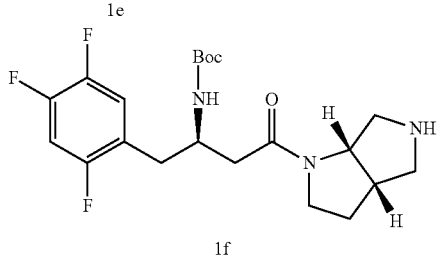

1f (c) converting the compound of formula (1f) to a compound of formula (1g) by a coupling reaction or acylation reaction, and

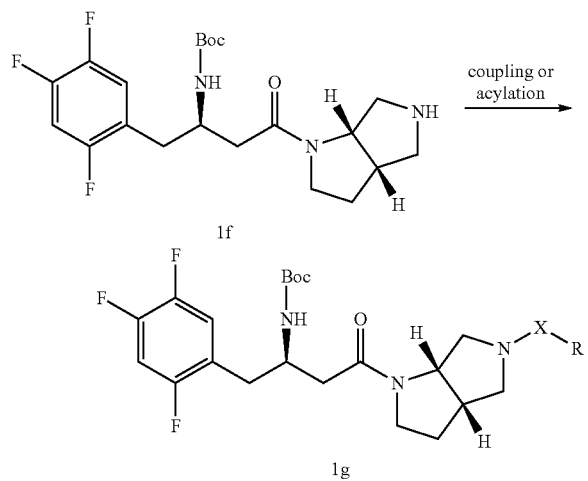

1f coupling or acylation →

1g (d) deprotecting the compound of formula (1 g) to a compound of formula (Ia) in the presence of an acid;

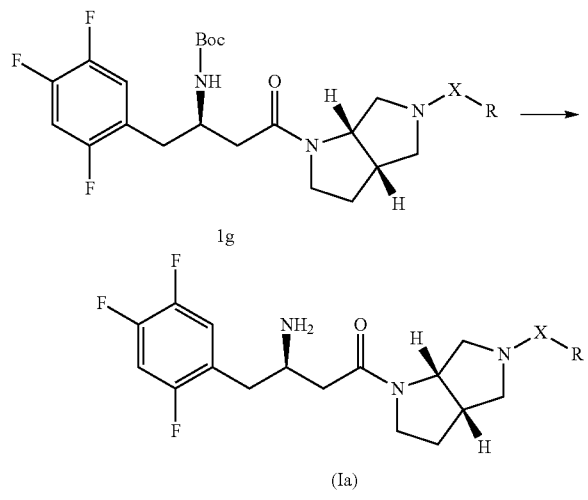

1g (Ia)

wherein,

X is selected from the group consisting of:

(1) —$C_1$-$C_3$ alkylidene-;

(2) —C(O)—;

(3) —S(O)$_2$—;

(4) —C(O)O—; and (5) —C(O)NR$^1$—;

R is selected from the group consisting of:

(1) H;

(2) $C_1$-$C_6$ alkyl, which is unsubstituted or substituted by one to three substituents selected from the following group: fluorine, chlorine or hydroxyl;

(3) $C_3$-$C_6$ cycloalkane, which is unsubstituted or substituted by one to two substituents selected from the following group: $C_1$-$C_3$ alkyl, fluorine, chlorine, hydroxyl, cyano, C(O)NH$_2$;

(4) Phenyl, which is unsubstituted or substituted by one to three substituents selected from the following: $C_1$-$C_3$ alkyl, fluorine, chlorine, cyano, S(O)$_2$R$^2$; and (5) 6-membered heterocycle containing one to two atoms independently selected from N atom, above-mentioned 6-membered heterocycle is unsubstituted or substituted by one to three substituents selected from the followings: $C_1$-$C_3$ alkyl, fluorine, chlorine, cyano, S(O)$_2$R$^2$;

Wherein, R$^1$ is H or $C_1$-$C_3$ alkyl;

R$^2$ is $C_1$-$C_3$ alkyl.

9. A method for the treatment of a disease associated with DPP-IV comprising the step of administering to a patient in need a pharmaceutical composition comprising the compound according to claim 1, or various optical isomers, various crystal forms, pharmaceutically acceptable inorganic or organic salts, hydrates or solvates thereof.

10. The method of claim 9, wherein the said disease is diabetes, obesity, or hyperlipemia.

11. The compound of claim 1, wherein

X is selected from the group consisting of:

(1) —C(O)—;

(2) —S(O)$_2$—;

(3) —C(O)O—; and (4) —C(O)NR$^1$.

* * * * *